US006284241B1

(12) United States Patent
Xu

(10) Patent No.: US 6,284,241 B1
(45) Date of Patent: Sep. 4, 2001

(54) COMPOUNDS FOR IMMUNOTHERAPY AND DIAGNOSIS OF COLON CANCER AND METHODS FOR THEIR USE

(75) Inventor: Jiangchun Xu, Bellevue, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/221,298

(22) Filed: Dec. 23, 1998

(51) Int. Cl.$^7$ .............................. C12N 15/00; C12N 5/00; C12P 21/06; C07H 21/04; A01N 63/00

(52) U.S. Cl. .................. 424/93.21; 435/69.1; 435/320.1; 435/325; 536/23.1; 536/23.5

(58) Field of Search ................................. 536/23.5, 23.1; 435/69.1, 320.1, 325; 424/93.21

(56) References Cited

FOREIGN PATENT DOCUMENTS

| | | |
|---|---|---|
| WO 98/53319 | 11/1998 | (WO) . |
| WO 99/01020 | 1/1999 | (WO) . |
| WO 99/60161 | 11/1999 | (WO) . |
| WO 99/63088 | 12/1999 | (WO) . |

OTHER PUBLICATIONS

Sheppard, PO (Zymogenetics, Inc.), WO 98/41627–A1, pp. 1–109, publication date Sep. 24, 1998.*

Behrens, et al., Science, vol. 280, pp. 596–599.*

Kennell, 1971. Prog. Nucl. Acid. Res. Mol. Biol., vol. 11, pp. 259–301.*

Chan et al., "Identification of novel genes that are differentially expressed in human colorectal carcinoma," *Biochimica et Biophysica Acta*, 1407 :200–204, 1998.

Frigerio et al., "Analysis of 2166 clones from a human colorectal cancer cDNA library by partial sequencing," *Human Molecular Genetics*, 4 (1):37–43, 1995.

Gelos et al., "Detection of genes differentially expressed in colorectal cancer: comparison of three methods," $2^{nd}$ *Congress of Molecular Medicine; Berlin, Germany,* 76 (6):B13, May, 1998.

Grimm and Johnson, "A modified screening method for pcDNA–1 expression libraries which is applicable to both surface and intracellular antigens Cloning of a colon carcinoma antigen," *Journal of Immunological Methods,* 186 : 305–312, 1995.

Tortola et al., "Analysis of differential gene expression in human colorectal tumor tissue by RNA arbitrarily primed–PCR: a technical assessment," *Laboratory Investigation,* 78 (3):309–317, Mar., 1998.

Yeatman and Mao, "Identifiaction of a differentially–expressed message associated with colon cancer liver metastasis using an improved method of differential display," *Nucleic Acid Research,* 23 (19):4007–4008, Mar., 1998.

GenBank Accession No. AA366895, "Initial assessment of human gene diversity and expression patterns based upon 83 million basepairs of cDNA sequence," located at http://www.ncbi.nlm.nih.gov.

GenBank Accession No. AF097021, "Identification and characterization of novel full–length cDNAs differentially expressed in human hematopoietic lineages," located at http://www.ncbi.nlm.nih.gov.

* cited by examiner

Primary Examiner—Deborah J. R. Clark
Assistant Examiner—Shin-Lin Chen
(74) Attorney, Agent, or Firm—Seed Intellectual Property Law Group PLLC

(57) ABSTRACT

Compounds and methods for the treatment and diagnosis of colon cancer are provided. The inventive compounds include polypeptides containing at least a portion of a colon tumor protein. Vaccines and pharmaceutical compositions for immunotherapy of colon cancer comprising such polypeptides, or polynucleotide molecules encoding such polypeptides, are also provided, together with DNA molecules for preparing the inventive polypeptides.

4 Claims, No Drawings

SEQUENCE LISTING

```
<160> NUMBER OF SEQ ID NOS: 112

<210> SEQ ID NO 1
<211> LENGTH: 458
<212> TYPE: DNA
<213> ORGANISM: Human
<220> FEATURE:
<221> NAME/KEY: modified_base
<222> LOCATION: (1)
<223> OTHER INFORMATION: Where n is a, c, g or t

<400> SEQUENCE: 1
ncaggtctgg cggcacctgt gcactcagcc gtcgatacac tggtcgattg ggacagggaa      60
gacgatgtgg ttttcaggga ggcccagaga tttggagaag cggatgaagt tctcctttag    120
ttccgaagtc agctccttgg ttctcccgta gagggtgatc ttgaagtact ccctgttttg    180
agaaactttc ttgaagaaca ccatagcatg ctggttgtag ttggtgctca ccactcggac    240
gaggtaactc gttaatccag ggtaactctt aatgttgccc agcgtgaact cgccgggctg    300
gcaacctgga acaaagtcc tgatccagta gtcacacttc tttttcctaa acaggacgga     360
ggtgacattg tagctcttgt cttctttcag ctcatagatg gtggcataca tcttttgcgg    420
gtctttgtct tctctgagaa ttgcattccc tgccagga                            458

<210> SEQ ID NO 2
<211> LENGTH: 423
<212> TYPE: DNA
<213> ORGANISM: Human

<400> SEQUENCE: 2
cagggtccat aggtgatccg caactctcga gcatttatat acaatagcaa atcatccagt     60
```

| | |
|---|---:|
| gtgttgtaca gtctataata ctccaacagt ctcccatctg tattcaatgg cgccacccaa | 120 |
| tacagtcctt tgtttggatg ctggggagag taatccctac cccaagcacc atatagataa | 180 |
| gaaaaccctc tccagttgag ctgaaccaca gacggtttgc tgatgttcac cacaccacca | 240 |
| tgaccacagc tccctggagt gggaggaggg tggacgacag gggtgttttg atctttagag | 300 |
| gcttcacact ctttcagctt ggtcttcaga gccacgattt tcggcgaat ggcaaggaca | 360 |
| ttgttttgt ctagtgtctc aagcttctct accaagagag tcatatttct tatctccacc | 420 |
| tcc | 423 |

<210> SEQ ID NO 3
<211> LENGTH: 538
<212> TYPE: DNA
<213> ORGANISM: Human

<400> SEQUENCE: 3

| | |
|---|---:|
| ggtctgtcca atggcaacag gaccctcact ctaytcartg tcacaagraa tgayrcagsa | 60 |
| msctayraat gtgaaaycca gaacccagtg agtgccarsc gcagtgayyc agtcatcctg | 120 |
| aatgtcctct atgcccrga tgmccccacc atttccccctc taaacacatm ttaccgwyca | 180 |
| ggggaaaatc tgaacctctc ctgccacgca gcctctaacc cacctgcaca gtactcttgg | 240 |
| tttrtcaatg ggactttcca gcaatccacm caagagctct ttatccccaa catcactgtg | 300 |
| aataatagyg gatcctatac gtgccaagcc cataactcag mcactggcct caataggacc | 360 |
| acagtcacga cgatcacagt ctatgcaaga gccacccaaa cccttcatca ccagcaacaa | 420 |
| ctccaacccc gtggaggatg aggatgctgt agccttaacc tgtgaacctg agattcagaa | 480 |
| cacaacctac ctgtggtggg taaataatca gagcctcccg gtcagtccca ggctgcag | 538 |

<210> SEQ ID NO 4
<211> LENGTH: 309
<212> TYPE: DNA
<213> ORGANISM: Human

<400> SEQUENCE: 4

| | |
|---|---:|
| tggtaascca aaaagatgct ggggcagatt gtggacaagt agaagaacct ccttcccctc | 60 |
| tgcgaacatt gaacggcgtg gattcaatag tgagcttggc agtggtgggc gggttccaga | 120 |
| aggttagaag tgaggctgtg agcaggagcc cctgccaggg gatvcacgca mtctgtgggg | 180 |
| aggggctgag rggdgwcycc atggtctctg ctgtctgctc tgtcctcctc tgtggagaag | 240 |
| agcttgagct ccaggaacgc tttgrtcavg gctgcctgtg acctytgctc tgbtctgcct | 300 |
| gcccgggcg | 309 |

<210> SEQ ID NO 5
<211> LENGTH: 412
<212> TYPE: DNA
<213> ORGANISM: Human

<400> SEQUENCE: 5

| | |
|---|---:|
| gtccaatggc aacaggaccc ctcacttcta ttcaatgtca caagaaatga cgcaagagcc | 60 |
| tatgtatgtg gaatccagaa ctkcagtgag tgcaaaccgc agtgacccag tcaccctgga | 120 |
| tgtcctctat gggccagaca sccccatca tttccccccc agactcgtct tacctttcgg | 180 |
| gagcgaacct caacctctcc tgccactcgg cctctaaccc atccccgcag tattcttggc | 240 |
| kgtatcaatg ggataccgca gcaacacaca caagttctct ttatcgccaa aatcacgcca | 300 |
| aataataacg ggacctatgc ctgttttgtc tctaacttgg ctactggccc gcaataattc | 360 |

```
catagtcaag agcatcacag tcttctgcat ctggaacttc tcctggtctt ct          412

<210> SEQ ID NO 6
<211> LENGTH: 332
<212> TYPE: DNA
<213> ORGANISM: Human

<400> SEQUENCE: 6
gtgcaagggc tttacaaaaa ctgtgccagt krcttctyca tgwsrcwrga tctgacttka   60
ttsaygttkt atgagsysya saatmctgaw gctcmttyts sakgrwsttc kgsatmrgca  120
gtsrattcsa catttgggrt akrtymtctc tsgaagysam tgtcakgcag tgrcayccwr  180
gkktcwgcwt gcwgtgrgtt amcakcmwtr ywtagkgsgm ayatrattta ramrgtayak  240
cymtctcmct cytycmccay wtgcwcaass mkcacacctc ggccgcgacc acgctaagcc  300
cgaattccag cacactggcg gccgttacta gt                                332

<210> SEQ ID NO 7
<211> LENGTH: 401
<212> TYPE: DNA
<213> ORGANISM: Human

<400> SEQUENCE: 7
tggtgttgtt ggcgccagtt ccctggacct ggaacagccg tgtggagggc ccggtctcca   60
agttgttagt tcgggaggtg cctccctggt agaccaccat gcgtcccttg aagatggaca  120
taagatgagg tggctccttg cccattggga cccggatctg gactggttca ccattgtact  180
tctggtccag gatgacggct tgataagctg atgctgtaat ttcatcttgg ctggcctggc  240
tgccctgcca aacgtagagc aggtaatgct gcttctcgcc gatgaaggta ggtgtaagag  300
cagcaggtaa gcaagttcgc ccccatagaa gtgggcctag ccacttggaa ttccagcaca  360
ctggcggccc gttactagtg ggatcccgag ctcggtacca a                      401

<210> SEQ ID NO 8
<211> LENGTH: 1151
<212> TYPE: DNA
<213> ORGANISM: Human

<400> SEQUENCE: 8
ctctctccat aaaactcagc actttacaga tgtagaatat ataagcatgc caaatttact   60
tatctgccac atacaaagca tcattccagg tgctagtgag gggaaaaaaa agttggagat  120
ttggtccctc gaggagctcc agatattaat ctacctaact aagtcccag gtttcttcca  180
ggcatgaag aattagtggt gctacatgga tgaggactag tcattgggca atatttcctg  240
tacaaagaat ccctagacgc catactgagt tttaagttcc ttaattccta atttaaggct  300
tctagtgaag cctcctcaca gtaggcttca ctaggcccac agtgccccta gacctctgac  360
aatcccaccc tagacagact ttattgcaaa atgcgcctga agaggcagat gattcccaag  420
agaactcacc aaatcaagac aaatgtccta gatctctagt gtggtagaac tatgcaccta  480
aacattgctg caaaatgaac acactttag acaccctgc agatatctaa gtaagtggag  540
aagactattt tttcaacaaa catttctct ttcacccctaa ctcctaaaca gcttactggg  600
gcttctgcaa gacagaaaga tcataattca gaaggtaacc atcgttatag acataaagtt  660
tctggtcaaa agggttatag ttaatgctct gcactttttc ctgcatctta tgcattacaa  720
tgtctagttt gccctctttc cctgtgtttg tgtcataata gtaaaaaatc tcttctgttc  780
```

| | |
|---|---|
| tggtgtttca tagtacgggt ggcatacaga acccccacata ccatgaaggc gttagaagca | 840 |
| gatggtttat actgcttggt ataccaagtg tttagcacct gaagtgtggt gtcattgagt | 900 |
| ttactaatca ccatgttacc agtgctggct tcagttgaat aaataaccca caatccattc | 960 |
| tcatccacag caaagtcaat atcttgccaa gcaacattag catatgaaaa gcggttatta | 1020 |
| taggcagcat tagggagagt ttgagtcaca gcaatcgtgt tggtggtcag gttaactctg | 1080 |
| gcaatattcc cggtgttgta catgttgacg tacatgttgt tgttgtaaac tgctgtacca | 1140 |
| ctaccttgga c | 1151 |

<210> SEQ ID NO 9
<211> LENGTH: 604
<212> TYPE: DNA
<213> ORGANISM: Human
<220> FEATURE:
<221> NAME/KEY: modified_base
<222> LOCATION: (410)
<223> OTHER INFORMATION: Where n is a, c, g or t
<220> FEATURE:
<221> NAME/KEY: modified_base
<222> LOCATION: (427)
<223> OTHER INFORMATION: Where n is a, c, g or t

<400> SEQUENCE: 9

| | |
|---|---|
| ctgtgcaagg gctttacaaa aactgtgcca ggacttccca tgaggctgga ttgcttgatt | 60 |
| catgttttat gagccccaca atactgaagc tccttttcca gggacttggc ataggcagtc | 120 |
| aattccacat ttgggatagg tcctctctgg aagtgaatgt caggcagtga catccaagtt | 180 |
| tctgcatgca gtgggttaac agccatgttt aggggaaca tgatttaaaa agtacatctc | 240 |
| tctccctcct cccccacatg cacaaggctc acatctcatt atggtgkcgg cccatgtcac | 300 |
| attaaagtgt gatacttkgg ttttgaaaac attcaaacag tctctgtgga aatctggaga | 360 |
| gaaattggcg gagagctgcc gtggtgcatt cctcctgtag tgcttcaagn taatgcttca | 420 |
| tcctttntta ataactttg atagacaggg gctagtcgca cagacctctg ggaagccctg | 480 |
| gaaaacgctg atgcttgttt gaagatctca agcgcagagt ctgcaagttc atccctctt | 540 |
| tcctgaggtc tgttggctgg aggctgcaga acattggtga tgacatggac cacgccattt | 600 |
| gtgg | 604 |

<210> SEQ ID NO 10
<211> LENGTH: 473
<212> TYPE: DNA
<213> ORGANISM: Human

<400> SEQUENCE: 10

| | |
|---|---|
| tcgagaagat ccctagtgag actttgaacc gtatcctggg cgacccagaa gccctgagag | 60 |
| acctgctgaa caaccacatc ttgaagtcag ctatgtgtgc tgaagccatc gttgcggggc | 120 |
| tgtctgtgga gaccctggag ggcacgacac tggaggtggg ctgcagcggg gacatgctca | 180 |
| ctatcaacgg gaaggcgatc atctccaata aagacatcct agccaccaac ggggtgatcc | 240 |
| actacattga tgagctactc atcccagact cagccaagac actatttgaa ttggctgcag | 300 |
| agtctgatgt gtccacagcc attgaccttt tcagacaagc cggcctcggc aatcatctct | 360 |
| ctggaagtga gcggttgacc ctcctgggct cccctgaatt ctgtattcaa agatggaacc | 420 |
| cctccaattg atgcccatac aaggaatttg cttcggaacc acataattaa aga | 473 |

<210> SEQ ID NO 11
<211> LENGTH: 411

```
<212> TYPE: DNA
<213> ORGANISM: Human
<220> FEATURE:
<221> NAME/KEY: modified_base
<222> LOCATION: (251)
<223> OTHER INFORMATION: Where n is a, c, g or t
<220> FEATURE:
<221> NAME/KEY: modified_base
<222> LOCATION: (276)
<223> OTHER INFORMATION: Where n is a, c, g or t
<220> FEATURE:
<221> NAME/KEY: modified_base
<222> LOCATION: (406)
<223> OTHER INFORMATION: Where n is a, c, g or t
<220> FEATURE:
<221> NAME/KEY: modified_base
<222> LOCATION: (409)
<223> OTHER INFORMATION: Where n is a, c, g or t

<400> SEQUENCE: 11
tcctcattgg tcggggccaa aagcgtgtac tggccgttac cttcaagcat cgtgttgagc      60
cctgatgcag ccacagcagc ccgaagggtc tcaaaggtgt cctcgatctc aatgatctgc     120
tggatgttgt tggtgatggt ggagatgacc ttatcgatga ggtgcaccac cccgttggtt     180
gcatggtggt cggctttyar carccgggca cagttcacag ttacaatccc attaggatag     240
tggtggatct nggatgttgg aattctggta catagnaggt gagggtcat gcccgtgttt      300 cagctcatca gtcaggactc gcctgcccac catatggtaa gcsgragggc atttgagcag     360
ctcaatgttt gacattgctg gaccagggga gttccagcac ttctangang a              411

<210> SEQ ID NO 12
<211> LENGTH: 560
<212> TYPE: DNA
<213> ORGANISM: Human

<400> SEQUENCE: 12
tacttgcctg gagatwgcyt tykckwtmtg ytcwrawgtc cgtggataca gaaatctctg      60
caggcaagtt gctccagagc atattgcagg acaagcctgt aacgaatagt taaattcacg     120
gcatctggat tcctaatcct tttccgaaat ggcaggtgtg agtgcctgta taaaatattc     180
tatgtttacc ttcaacttct tgttctggct atgtggtatc ttgatcctag cattagcaat     240
atgggtacga gtaagcaatg actctcaagc aatttttggt tctgaagatg taggctctag     300
ctcctacgtt gctgtggaca tattgattgc tgtaggtgcc atcatcatga ttctgggctt     360
cctgggatgc tgcggtgcta taaaagaaag tcgctgcatg cttctgttgt ttttcatagg     420
cttgcttctg atcctgctcc tgcaggtggg cgacaggtat cctaggagct gttttcaaat     480
ctaagtctga tcgcattgtg aatgaaactc tctatgaaaa cacaaagctt ttgagcgcca     540
caggggaaag tgaaaaacaa                                                560

<210> SEQ ID NO 13
<211> LENGTH: 150
<212> TYPE: DNA
<213> ORGANISM: Human

<400> SEQUENCE: 13
gggcaggctg tctttttaaa atgtctcggc tagctagacc acagatatct tctagacata      60
ttgaacacat ttaagatttg agggatataa gggaaaatga tatgaatgtg tattttact      120 caaaataaaa gtaactgttt acgttggtga                                     150

<210> SEQ ID NO 14
```

<211> LENGTH: 403
<212> TYPE: DNA
<213> ORGANISM: Human

<400> SEQUENCE: 14

```
ctgctgcctg tggcgtgtgt gggctggatc ccttgaaggc tgagttttg agggcagaaa      60
gctagctatg ggtagccagg tgttacaaag gtgctgctcc ttctccaacc cctacttggt    120
ttccctcacc ccaagcctca tgttcatacc agccagtggg ttcagcagaa cgcatgacac    180
cttatcacct ccctccttgg gtgagctctg aacaccagct ttggcccctc cacagtaagg    240
ctgctacatc aggggcaacc ctggctctat cattttcctt ttttgccaaa aggaccagta    300
gcataggtga gccctgagca ctaaaaggag gggtccctga agctttccca ctatagtgtg    360
gagttctgtc cctgaggtgg gtacagcagc cttggttcct ctg                      403
```

<210> SEQ ID NO 15
<211> LENGTH: 688
<212> TYPE: DNA
<213> ORGANISM: Human
<220> FEATURE:
<221> NAME/KEY: modified_base
<222> LOCATION: (638)
<223> OTHER INFORMATION: Where n is a, c, g or t
<220> FEATURE:
<221> NAME/KEY: modified_base
<222> LOCATION: (639)
<223> OTHER INFORMATION: Where n is a, c, g or t
<220> FEATURE:
<221> NAME/KEY: modified_base
<222> LOCATION: (649)
<223> OTHER INFORMATION: Where n is a, c, g or t
<220> FEATURE:
<221> NAME/KEY: modified_base
<222> LOCATION: (660)
<223> OTHER INFORMATION: Where n is a, c, g or t
<220> FEATURE:
<221> NAME/KEY: modified_base
<222> LOCATION: (666)
<223> OTHER INFORMATION: Where n is a, c, g or t
<220> FEATURE:
<221> NAME/KEY: modified_base
<222> LOCATION: (669)
<223> OTHER INFORMATION: Where n is a, c, g or t
<220> FEATURE:
<221> NAME/KEY: modified_base
<222> LOCATION: (671)
<223> OTHER INFORMATION: Where n is a, c, g or t
<220> FEATURE:
<221> NAME/KEY: modified_base
<222> LOCATION: (673)
<223> OTHER INFORMATION: Where n is a, c, g or t
<220> FEATURE:
<221> NAME/KEY: modified_base
<222> LOCATION: (674)
<223> OTHER INFORMATION: Where n is a, c, g or t
<220> FEATURE:
<221> NAME/KEY: modified_base
<222> LOCATION: (679)
<223> OTHER INFORMATION: Where n is a, c, g or t
<220> FEATURE:
<221> NAME/KEY: modified_base
<222> LOCATION: (684)
<223> OTHER INFORMATION: Where n is a, c, g or t

<400> SEQUENCE: 15

```
caaagcacat tttaatcatt tattttaaaa gggggagtaa agcatttaaa ctgccaatcc      60
tatagactag gacttgaaca tcaaaggaaa aatagacaaa gactagatga taaagtcatt    120
caaaagcaca gaagcacatc acatacacca gcaaggtttc caactactgc actgattaac    180
tagatactct caatagcttt tctatagctc gtcctagaaa aaaaaattaa attttcattt    240
```

```
tcttacaagt tccaggctta acaaaggca aaaattacat gcaacaactg atacactcat      300
aagttgcaca tatgctccaa ggtctttatt agataacaat aaatgctagc actttgtcac      360
tgccatcaga ttttccttat agtcttagag tcatgtaaat aaaagttcca taatgaaatt      420
aaagaaaatt aatttttcta atcttagatc agttccatag aaaactatta attttttttaa     480 agtaggcagt agaagggggt tggtgggggg tggaattggt tagtaagtct ggttctaatc      540
ttctgagctg cctttggaag gaagttatga ggtagaagat tctactgact tttagtaagg      600
tggacaatga gagaaaagaa aaagcaggtg cctcatcnnc agatccttnt ggtatttatn      660
tgccangtnc nanntaatnc atanaaag                                         688
```

```
<210> SEQ ID NO 16
<211> LENGTH: 408
<212> TYPE: DNA
<213> ORGANISM: Human

<400> SEQUENCE: 16
caggtcatca agatgactta caggatgtaa tagggagagc tgtcgagatt ggtgttaaaa       60
agtttatgat tacaggtgga aatctacaag acagtaaaga tgcactgcat ttggcacaaa      120
caaatggtat gttttttcagt acagttggat gtcgtcctac aagatgtggt gaatttgaaa     180
agaataaccc tgatctttac ttaaaggagt tgctaaatct tgctgaaaac aataaaggga     240
aagttgtggc aataggagaa tgcggacttg attttgaccc gactgcagtt ttgtcccaaa      300
gatactcaac tcaaatattt tgaaaaacag tttgaactgt cagaacaaac aaaattacca     360
atgtttcttc attgtccgaa actcacatgc tgaattttttg gacataat                  408
```

```
<210> SEQ ID NO 17
<211> LENGTH: 407
<212> TYPE: DNA
<213> ORGANISM: Human

<400> SEQUENCE: 17
ggtcctgggg aggccctagg ggagcaccgt gatggagagg acagagcagg ggctccagca       60
ccttctttct ggactggcgt tcacctccct gctcagtgct tgggctccac gggcaggggt      120
cagagcactc cctaatttat gtgctatata aatatgtcag atgtacatag agatctatttt     180 tttctaaaac attcccctyc ccactcctct cccacagagt gctggactgt tccaggccct    240
ccagtgggct gatgctggga cccttaggat ggggctccca gctccttttct cctgtgaatg     300 gaggcagaag acctccaata aagtgccttc tgggcttttt ctaacctttg tcttagctac      360
ctgtgtactg aaatttgggc ctttggatcg aatatggtca agaggtt                    407
```

```
<210> SEQ ID NO 18
<211> LENGTH: 405
<212> TYPE: DNA
<213> ORGANISM: Human

<400> SEQUENCE: 18
tgaagagtca acttgggcct ggaggactga taaagtttgt gattttgagg gcctctaaaa       60
gtattaaagc agcggcagcc gctgcacgca gacatgaggg ctaggttaaa acagtaagat      120
caagttgttt ggacagaaag gctacagagt gtggtcctgg ctcttgtgta agaattacga      180
ccacgctaac catgcctagg aaggaaagga gttattgttt tgtagaaagg tgctgggggtt     240 tgagagatca gtcggacacg attggcaggg agagcacgtg tgtttttatg agaattatgc      300
```

```
ccgagatagg taacagatga ggaagaaatt tgggcttgat tgaagtaatg ggggctgtct    360
gtgaagcttt gcagcagtac agcctaggta atttgctgag cctaa                   405

<210> SEQ ID NO 19
<211> LENGTH: 401
<212> TYPE: DNA
<213> ORGANISM: Human

<400> SEQUENCE: 19
tcctgacatt cctgccttct tatattaata agacaaataa aacaaaatag tgttgaagtg    60
ttggggcagc gaaaattttt gggggtggt atggagagat aatgggcgat gtttctcagg   120
gctgcttcaa gcgggattag gggcggcgtg ggagcctaga gtgggagaga ttaagctgaa   180
gggaggtctt gtggtaaggg gtgatatcat ggggatgtta aagaaacat ttgtcgtata    240 gaatgattgg tgatggcctg gatacggttt tggatgattt gagaagctaa atggaagata   300
caaggtccga ataaaaggag gagaaaaatg ggtattaaat gtctaagaat tgggaggacc   360
taggacatct gattagagag tgcctaagga gattcagcat a                       401

<210> SEQ ID NO 20
<211> LENGTH: 331
<212> TYPE: DNA
<213> ORGANISM: Human

<400> SEQUENCE: 20
aggtccagct ctgtctcata cttgactcta aagtcatcag cagcaagacg ggcattgtca    60
atctgcagaa cgatgcgggc attgtccaca gtatttgcga agatctgagc cctcaggtcc   120
tcgatgatct tgaagtaatg gctccagtct ctgacctggg gtcccttctt ctccaagtgc   180
tcccggattt tgctctccag cctccggttc tcggtctcca ggctcctcac tctgtccagg   240
taagaggcca ggcggtcgtt caggctttgc atggtctcct tctcgttctg gatgcctccc   300
attcctgcca gaccccggc tatcccggtg g                                   331

<210> SEQ ID NO 21
<211> LENGTH: 346
<212> TYPE: DNA
<213> ORGANISM: Human
<220> FEATURE:
<221> NAME/KEY: modified_base
<222> LOCATION: (257)
<223> OTHER INFORMATION: Where n is a, c, g or t

<400> SEQUENCE: 21
ggtccaccac ttgtacccga tatggacttc cggcttctct gtccaatgga gccacactaa    60
agatctcacc agtcacgtgg tcaattttaa gccaacctct tgtgtctccc ctcagtgaat   120
agcttatgtc cagaccttct ggatccttgg cagtcacatt gcccacttta gtgcctatag   180
ctacatcctc actgactttc gcttggaata cgtgttggga aaattgaggt gcttcattca   240
catctgtcac aataagncgt gaacttggca aaagaacttg cattgtactt cacaccaaac   300
actagaggct caggattttc tgctttgaac acaatgttgg aaacag                  346

<210> SEQ ID NO 22
<211> LENGTH: 360
<212> TYPE: DNA
<213> ORGANISM: Human
<220> FEATURE:
<221> NAME/KEY: modified_base
<222> LOCATION: (317)
<223> OTHER INFORMATION: Where n is a, c, g or t
```

<400> SEQUENCE: 22

```
gaagactccc tctctcggaa gccggatccc gagccgggca ggatggatca ccaccagccg      60
gggactgggc gctaccaggt gcttcttaat gaagaggata actcagaatc atcggctata     120
gagcagccac ctacttcaaa cccagcaccc gcagattgtg caggctgcgt cttcagcacc     180
agcacttgaa actgactctt cccctccacc atatagtagt attactggtg gaagtaccta     240
caacttcaga tacagaagtt tacggtgagt tttatcccgt gccacctccc tatagcgttg     300
ctacctctct tcctacnwta cgatgaaagc tgagaaggct aaagctgctg caatggcatg     360
```

<210> SEQ ID NO 23
<211> LENGTH: 251
<212> TYPE: DNA
<213> ORGANISM: Human

<400> SEQUENCE: 23

```
ggcggagctc cacgacgagc tggaaaagga acctttgag gatggctttg caaatgggga       60
agaaagtact ccaaccagag atgctgtggt cacgtatact gcagaaagta aaggagtcgt     120
gaagtttggc tggatcaagg gtgtattagt acgttgtatg ttaaacattt ggggtgtgat     180
gcttttcatt agattgtcat ggattgtggg tcaagctgga ataggtctat cagtccttgt     240
aataatgatg g                                                          251
```

<210> SEQ ID NO 24
<211> LENGTH: 421
<212> TYPE: DNA
<213> ORGANISM: Human
<220> FEATURE:
<221> NAME/KEY: modified_base
<222> LOCATION: (182)
<223> OTHER INFORMATION: Where n is a, c, g or t

<400> SEQUENCE: 24

```
caggtctttc ccaggtgttg actccagctc cagcttcagc tccagctcca ggtcgggctc      60
cagctccagc cgcagcttar gcagcgggag gttctgtgtc ccagttgttt tccaatttca     120
ccggctcccg tggatgamcg ygggacctgy caswgctcct gtktyccgc yagsacacca      180
cnytttyccg tggacacrar kggaacckct tggaattcac agctyatgtt ctttctcara     240
agtttgagaa agaactttct aaagtgaggg aatatgtcca attaattagt gtgtatgaaa     300
agaaactgtt aaacctaact gtccgaattg acatcatgga raaaggatac catttcttac     360
actgaactgg acttcgagct gatcaaggta gaagtgaagg agatggaaaa actggtcata     420
c                                                                      421
```

<210> SEQ ID NO 25
<211> LENGTH: 381
<212> TYPE: DNA
<213> ORGANISM: Human
<220> FEATURE:
<221> NAME/KEY: modified_base
<222> LOCATION: (81)
<223> OTHER INFORMATION: Where n is a, c, g or t
<220> FEATURE:
<221> NAME/KEY: modified_base
<222> LOCATION: (146)
<223> OTHER INFORMATION: Where n is a, c, g or t
<220> FEATURE:
<221> NAME/KEY: modified_base
<222> LOCATION: (291)
<223> OTHER INFORMATION: Where n is a, c, g or t
<220> FEATURE:

<221> NAME/KEY: modified_base
<222> LOCATION: (355)
<223> OTHER INFORMATION: Where n is a, c, g or t

<400> SEQUENCE: 25
gaactttttg tttctttatt ttcaatattt gtcttattaa tattttctt attttataat    60 gcaattacaa caatttagga nacaaaacaa tataaacaaa agaatgttaa atagtttttt   120
ttaaaaaata gcttgttgct tgcaanaaag tccatataat cttattcccc cccaaatata   180
attttatact ttgcactaaa ccaaaatagc ttatggaaaa ttagtattaa atagctaaac   240
acagaaaacc tacagctata aataacataa aatacagttt aactttaatg ngatgcttaa   300
acaaagcaaa ctatgatgca atatgaatca acttcattaa ttggacaagt ccagnggagg   360
cacaaattag ataagcacta a                                              381

<210> SEQ ID NO 26
<211> LENGTH: 401
<212> TYPE: DNA
<213> ORGANISM: Human
<220> FEATURE:
<221> NAME/KEY: modified_base
<222> LOCATION: (219)
<223> OTHER INFORMATION: Where n is a, c, g or t
<220> FEATURE:
<221> NAME/KEY: modified_base
<222> LOCATION: (236)
<223> OTHER INFORMATION: Where n is a, c, g or t
<220> FEATURE:
<221> NAME/KEY: modified_base
<222> LOCATION: (276)
<223> OTHER INFORMATION: Where n is a, c, g or t
<220> FEATURE:
<221> NAME/KEY: modified_base
<222> LOCATION: (300)
<223> OTHER INFORMATION: Where n is a, c, g or t
<220> FEATURE:
<221> NAME/KEY: modified_base
<222> LOCATION: (303)
<223> OTHER INFORMATION: Where n is a, c, g or t
<220> FEATURE:
<221> NAME/KEY: modified_base
<222> LOCATION: (310)
<223> OTHER INFORMATION: Where n is a, c, g or t
<220> FEATURE:
<221> NAME/KEY: modified_base
<222> LOCATION: (325)
<223> OTHER INFORMATION: Where n is a, c, g or t
<220> FEATURE:
<221> NAME/KEY: modified_base
<222> LOCATION: (330)
<223> OTHER INFORMATION: Where n is a, c, g or t
<220> FEATURE:
<221> NAME/KEY: modified_base
<222> LOCATION: (335)
<223> OTHER INFORMATION: Where n is a, c, g or t
<220> FEATURE:
<221> NAME/KEY: modified_base
<222> LOCATION: (359)
<223> OTHER INFORMATION: Where n is a, c, g or t
<220> FEATURE:
<221> NAME/KEY: modified_base
<222> LOCATION: (374)
<223> OTHER INFORMATION: Where n is a, c, g or t
<220> FEATURE:
<221> NAME/KEY: modified_base
<222> LOCATION: (380)
<223> OTHER INFORMATION: Where n is a, c, g or t
<220> FEATURE:
<221> NAME/KEY: modified_base
<222> LOCATION: (390)
<223> OTHER INFORMATION: Where n is a, c, g or t

<400> SEQUENCE: 26

```
ggaaaaggga ctggcctctc tgaagagtga gatgagggaa gtggaaggag agctggaaag      60
gaaggagctg gagtttgaca cgaatatgga tgcagtacag atggtgatta cagaagccca     120
gaaggttgat accagaagcc aagaacgctg gggttacaat ccaagacaca ctcaacacat     180
tagacgggct cctgcattct gatggaccaa cctttcang tggtaagatt gaagangggg      240
cctgggctta cctgggaagc aaaaactttt cccganccaa ggaacccagg attcaaccan     300
gcnacttgcn ggccaaggaa ggcanaactn ggaanaaaag gccccttaag caaaagggnc     360
accttcattt gctnggaaan cagcctttan ttggaatctt g                         401
```

<210> SEQ ID NO 27
<211> LENGTH: 383
<212> TYPE: DNA
<213> ORGANISM: Human
<220> FEATURE:
<221> NAME/KEY: modified_base
<222> LOCATION: (31)
<223> OTHER INFORMATION: Where n is a, c, g or t
<220> FEATURE:
<221> NAME/KEY: modified_base
<222> LOCATION: (38)
<223> OTHER INFORMATION: Where n is a, c, g or t
<220> FEATURE:
<221> NAME/KEY: modified_base
<222> LOCATION: (49)
<223> OTHER INFORMATION: Where n is a, c, g or t
<220> FEATURE:
<221> NAME/KEY: modified_base
<222> LOCATION: (100)
<223> OTHER INFORMATION: Where n is a, c, g or t
<220> FEATURE:
<221> NAME/KEY: modified_base
<222> LOCATION: (142)
<223> OTHER INFORMATION: Where n is a, c, g or t
<220> FEATURE:
<221> NAME/KEY: modified_base
<222> LOCATION: (147)
<223> OTHER INFORMATION: Where n is a, c, g or t
<220> FEATURE:
<221> NAME/KEY: modified_base
<222> LOCATION: (181)
<223> OTHER INFORMATION: Where n is a, c, g or t
<220> FEATURE:
<221> NAME/KEY: modified_base
<222> LOCATION: (250)
<223> OTHER INFORMATION: Where n is a, c, g or t
<220> FEATURE:
<221> NAME/KEY: modified_base
<222> LOCATION: (258)
<223> OTHER INFORMATION: Where n is a, c, g or t
<220> FEATURE:
<221> NAME/KEY: modified_base
<222> LOCATION: (272)
<223> OTHER INFORMATION: Where n is a, c, g or t
<220> FEATURE:
<221> NAME/KEY: modified_base
<222> LOCATION: (274)
<223> OTHER INFORMATION: Where n is a, c, g or t
<220> FEATURE:
<221> NAME/KEY: modified_base
<222> LOCATION: (297)
<223> OTHER INFORMATION: Where n is a, c, g or t
<220> FEATURE:
<221> NAME/KEY: modified_base
<222> LOCATION: (340)
<223> OTHER INFORMATION: Where n is a, c, g or t
<220> FEATURE:
<221> NAME/KEY: modified_base
<222> LOCATION: (341)
<223> OTHER INFORMATION: Where n is a, c, g or t
<220> FEATURE:
<221> NAME/KEY: modified_base
<222> LOCATION: (366)

```
<223> OTHER INFORMATION: Where n is a, c, g or t
<220> FEATURE:
<221> NAME/KEY: modified_base
<222> LOCATION: (368)
<223> OTHER INFORMATION: Where n is a, c, g or t
<220> FEATURE:
<221> NAME/KEY: modified_base
<222> LOCATION: (377)
<223> OTHER INFORMATION: Where n is a, c, g or t

<400> SEQUENCE: 27
aattgcaact ggactttat tgggcagtta cnacaacnaa tgttttcana aaaatatttg      60
gaaaaatat accacttcat agctaagtct tacagagaan aggatttgct aataaaactt    120
aagttttgaa aattaagatg cnggtanagc ttctgaacta atgcccacag ctccaaggaa    180
nacatgtcct atttagttat tcaaatacca gttgagggca ttgtgattaa gcaaacaata    240
tatttgttan aactttgntt ttaaattact gntncttgac attacttata aaggagnctc    300
taactttcga tttctaaaac tatgtaatac aaaagtatan ntttccccat tttgataaaa    360
gggccnanga tactgantag gaa                                            383

<210> SEQ ID NO 28
<211> LENGTH: 401
<212> TYPE: DNA
<213> ORGANISM: Human
<220> FEATURE:
<221> NAME/KEY: modified_base
<222> LOCATION: (212)
<223> OTHER INFORMATION: Where n is a, c, g or t

<400> SEQUENCE: 28
ggtcgcgttt ccctggctc acagtctgcc attatttgca tttttaaatg aagaaaagtt     60
taacgtggat ggatggacag tttacaatcc agtggaagaa tacaggaggc agggcttgcc   120
caatcaccat tggagaataa cttttattaa taagtgctat gagctctgcg acacttaccc   180
tgctcttttg gtggttccgt atcgtgcctc anatgatgac ctccggagag ttgcaacttt   240
taggtcccga aatcgaattc cagtgctgtc atggattcat ccagaaaata agacggtcat   300
tgtgcgttgc agtcagcctc ttgtcggtat gagtgggaaa cgaaataaag atgatgagaa   360
atatctcgat gttatcaggg agactaataa acaaatttct a                       401

<210> SEQ ID NO 29
<211> LENGTH: 401
<212> TYPE: DNA
<213> ORGANISM: Human

<400> SEQUENCE: 29
atatgagttt gccatctcca tggatgccat ttcaatgcct tcagggtaat cattctctcc     60
ccaaagactg cccacggggt catcactcct gtgacgaaat gagggctgga ttgaagatgt    120
tctgctgagc accccctgg tcatctttgg ggtctcagaa gagccataat catgaccatt    180
ctcagcatct gaataatcag gttctctcca agtgcttggc aagttctgat tgtcctcagc    240
actgggatag tctggctccc caaaaaaggg tggagagtta ggttgaatgt cagcgcctgg   300
ataatcaggc tttcccagag agtctgcgta tggattgatt ctaaaacttg tatgttccag   360
attctttctg gatcctggat ggttcaaatt ggctctgggt c                       401

<210> SEQ ID NO 30
<211> LENGTH: 401
<212> TYPE: DNA
<213> ORGANISM: Human
```

-continued

```
<400> SEQUENCE: 30
cctgaactat ttattaaaaa catgaccact cttggctatt gaagatgctg cctgtatttg      60
agagactgcc atacataata tatgacttcc tagggatctg aaatccataa actaagagaa     120
actgtgtata gcttacctga acaggaatcc ttactgatat ttatagaaca gttgatttcc     180
cccatcccca gtttatggat atgctgcttt aaacttggaa gggggagaca ggaagtttta     240
attgttctga ctaaacttag gagttgagct aggagtgcgt tcatggtttc ttcactaaca     300
gaggaattat gctttgcact acgtccctcc aagtgaagac agactgtttt agacagactt     360
tttaaaatgg tgccctacca ttgacacatg cagaaattgg t                         401

<210> SEQ ID NO 31
<211> LENGTH: 297
<212> TYPE: DNA
<213> ORGANISM: Human

<400> SEQUENCE: 31
acctccatta atgccaggtg ttcctcctct gatgccagga atgccaccag ttatgccagg      60
catgccacct ggattgcatc atcagagaaa atacacccag tcattttgcg gtgaaaacat     120
aatgatgcca atgggtggaa tgatgccacc tggaccagga ataccacctc tgatgcctgg     180
aatgccacca ggtatgcccc cacctgttcc acgtcctgga attcctccaa tgactcaagc     240
acaggctgtt tcagcgccag gtattcttaa tagaccacct gcaccaacag caactgt        297

<210> SEQ ID NO 32
<211> LENGTH: 401
<212> TYPE: DNA
<213> ORGANISM: Human

<400> SEQUENCE: 32
caaacctgga gccaaaaagg acacaaagga ctctcgaccc aaactgcccc agaccctctc      60
cagaggttgg ggtgaccaac tcatctggac tcagacatat gaagaagctc tatataaatc     120
caagacaagc aacaaaccct tgatgattat tcatcacttg ggtgagtgcc cacacagtca     180
agctttaaag aaagtgtttg ctgaaaataa agaaatccag aaattggcag agcagtttgt     240
cctcctcaat ctggtttatg aaacaactga caaacacctt tctcctgatg ccagtatgt      300
ccccaggatt atgtttgttg acccatctct gacagttaga gcccgatatc actggaagat     360
attcaaaccg tctctatgct tacgaacctg cagatacagc t                         401

<210> SEQ ID NO 33
<211> LENGTH: 401
<212> TYPE: DNA
<213> ORGANISM: Human

<400> SEQUENCE: 33
agcagaggga caggaatcat tcggccactg ttcagacggg agccacaccc ttctccaatc      60
caagcctggc cccagaagat cacaaagagc caaagaaact gcaggtgtc cacgcgctcc      120
aggccagtga gttggttgtc acttactttt tctgtgggga agaaattcca taccggagga    180
tgctgaaggc tcagagcttg accctgggcc actttaaaga gcagctcagc aaaaagggaa    240
attataggta ttacttcaaa aaagcaagcg atgagtttgc ctgtggagcg tgtttgagg     300
agatctgggg ggatgagacg gtgctcccga tgtatgaagg ccggattctg ggcaaagtgg   360
agcggatcga ttgagccctg gggtctggct ttggtgaact g                         401
```

<210> SEQ ID NO 34
<211> LENGTH: 401
<212> TYPE: DNA
<213> ORGANISM: Human

<400> SEQUENCE: 34
aacaatggct atgaaggcat tgtcgttgca atcgacccca atgtgccaga agatgaaaca      60
ctcattcaac aaataaagga catggtgacc caggcatctc tgtatctgtt tgaagctaca     120
ggaaagcgat tttatttcaa aaatgttgcc attttgattc ctgaaacatg gaagacaaag     180
gctgactatg tgagaccaaa acttgagacc tacaaaaatg ctgatgttct ggttgcttga     240
gtctactcct ccaggtaatg atgaaccctca cactgagcag atggggcaac tgtggagaga     300 agggtgaaa ggatcccacc tcactcctga tttcattgca ggaaaaaagt tagcttgaat     360
atggaccaca aggtaagggc atttgtccat gaatggggct c                          401

<210> SEQ ID NO 35
<211> LENGTH: 401
<212> TYPE: DNA
<213> ORGANISM: Human
<220> FEATURE:
<221> NAME/KEY: modified_base
<222> LOCATION: (184)
<223> OTHER INFORMATION: Where n is a, c, g or t
<220> FEATURE:
<221> NAME/KEY: modified_base
<222> LOCATION: (208)
<223> OTHER INFORMATION: Where n is a, c, g or t
<220> FEATURE:
<221> NAME/KEY: modified_base
<222> LOCATION: (251)
<223> OTHER INFORMATION: Where n is a, c, g or t
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (284)
<223> OTHER INFORMATION: Where n is a, c, g or t
<220> FEATURE:
<221> NAME/KEY: modified_base
<222> LOCATION: (293)
<223> OTHER INFORMATION: Where n is a, c, g or t
<220> FEATURE:
<221> NAME/KEY: modified_base
<222> LOCATION: (296)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (395)
<223> OTHER INFORMATION: Where n is a, c, g or t

<400> SEQUENCE: 35
catttcttcc tactagactg ccccttgat ccactggcag aaatgatggc accaccttgt      60
cttcaggtgg tgctccttca ttattccaag gatgcagcat ctctatggtg ccaggtatgg     120
gggtaaagcc tttggcgccc tttccgcaat ggcacatcag cagtaaaagt ggtaccaata     180
gcangaacag aaagggcaaa atcatgancg caattgctgc gggtcccaag cccacatagg     240
aatcatgctg ngcttccctg canccgctgc catgcaagac actnacaaac tgngantgta     300
aggacctgct tttcaggaca actaaaaccc tgattgnctg aaatcaggaa ctgaatttca     360
cttctcccaa gctttttctc actttggtgc aacancacac t                          401

<210> SEQ ID NO 36
<211> LENGTH: 401
<212> TYPE: DNA
<213> ORGANISM: Human

<400> SEQUENCE: 36

| | | | | | |
|---|---|---|---|---|---|
| cctgctagaa | tcactgccgc | tgtgctttcg | tggaaatgac | agttccttgt | ttttttttgtt | 60 |
| tctgtttttg | ttttacatta | gtcattggac | cacagccatt | caggaactac | cccctgcccc | 120 |
| acaaagaaat | gaacagttgt | agggagaccc | agcagcacct | ttcctccaca | caccttcatt | 180 |
| ttgaagttcg | ggttttttgtg | ttaagttaat | ctgtacattc | tgtttgccat | tgttacttgt | 240 |
| actatacatc | tgtatatagt | gtacggcaaa | agagtattaa | tccactatct | ctagtgcttg | 300 |
| actttaaatc | agtacagtac | ctgtacctgc | acggtcaccc | gctccgtgtg | tcgccctata | 360 |
| ttgagggctc | aagctttccc | ttgttttttg | aaagggggttt | a | | 401 |

<210> SEQ ID NO 37
<211> LENGTH: 401
<212> TYPE: DNA
<213> ORGANISM: Human
<220> FEATURE:
<221> NAME/KEY: modified_base
<222> LOCATION: (2)
<223> OTHER INFORMATION: Where n is a, c, g or t
<220> FEATURE:
<221> NAME/KEY: modified_base
<222> LOCATION: (3)
<223> OTHER INFORMATION: Where n is a, c, g or t
<220> FEATURE:
<221> NAME/KEY: modified_base
<222> LOCATION: (6)
<223> OTHER INFORMATION: Where n is a, c, g or t
<220> FEATURE:
<221> NAME/KEY: modified_base
<222> LOCATION: (9)
<223> OTHER INFORMATION: Where n is a, c, g or t
<220> FEATURE:
<221> NAME/KEY: modified_base
<222> LOCATION: (16)
<223> OTHER INFORMATION: Where n is a, c, g or t
<220> FEATURE:
<221> NAME/KEY: modified_base
<222> LOCATION: (18)
<223> OTHER INFORMATION: Where n is a, c, g or t
<220> FEATURE:
<221> NAME/KEY: modified_base
<222> LOCATION: (19)
<223> OTHER INFORMATION: Where n is a, c, g or t
<220> FEATURE:
<221> NAME/KEY: modified_base
<222> LOCATION: (23)
<223> OTHER INFORMATION: Where n is a, c, g or t
<220> FEATURE:
<221> NAME/KEY: modified_base
<222> LOCATION: (30)
<223> OTHER INFORMATION: Where n is a, c, g or t
<220> FEATURE:
<221> NAME/KEY: modified_base
<222> LOCATION: (33)
<223> OTHER INFORMATION: Where n is a, c, g or t
<220> FEATURE:
<221> NAME/KEY: modified_base
<222> LOCATION: (48)
<223> OTHER INFORMATION: Where n is a, c, g or t
<220> FEATURE:
<221> NAME/KEY: modified_base
<222> LOCATION: (56)
<223> OTHER INFORMATION: Where n is a, c, g or t
<220> FEATURE:
<221> NAME/KEY: modified_base
<222> LOCATION: (59)

```
<223> OTHER INFORMATION: Where n is a, c, g or t
<220> FEATURE:
<221> NAME/KEY: modified_base
<222> LOCATION: (62)
<223> OTHER INFORMATION: Where n is a, c, g or t
<220> FEATURE:
<221> NAME/KEY: modified_base
<222> LOCATION: (73)
<223> OTHER INFORMATION: Where n is a, c, g or t
<220> FEATURE:
<221> NAME/KEY: modified_base
<222> LOCATION: (75)
<223> OTHER INFORMATION: Where n is a, c, g or t
<220> FEATURE:
<221> NAME/KEY: modified_base
<222> LOCATION: (81)
<223> OTHER INFORMATION: Where n is a, c, g or t
<220> FEATURE:
<221> NAME/KEY: modified_base
<222> LOCATION: (85)
<223> OTHER INFORMATION: Where n is a, c, g or t
<220> FEATURE:
<221> NAME/KEY: modified_base
<222> LOCATION: (88)
<223> OTHER INFORMATION: Where n is a, c, g or t
<220> FEATURE:
<221> NAME/KEY: modified_base
<222> LOCATION: (89)
<223> OTHER INFORMATION: Where n is a, c, g or t
<220> FEATURE:
<221> NAME/KEY: modified_base
<222> LOCATION: (114)
<223> OTHER INFORMATION: Where n is a, c, g or t
<220> FEATURE:
<221> NAME/KEY: modified_base
<222> LOCATION: (116)
<223> OTHER INFORMATION: Where n is a, c, g or t
<220> FEATURE:
<221> NAME/KEY: modified_base
<222> LOCATION: (121)
<223> OTHER INFORMATION: Where n is a, c, g or t
<220> FEATURE:
<221> NAME/KEY: modified_base
<222> LOCATION: (137)
<223> OTHER INFORMATION: Where n is a, c, g or t
<220> FEATURE:
<221> NAME/KEY: modified_base
<222> LOCATION: (149)
<223> OTHER INFORMATION: Where n is a, c, g or t
<220> FEATURE:
<221> NAME/KEY: modified_base
<222> LOCATION: (158)
<223> OTHER INFORMATION: Where n is a, c, g or t
<220> FEATURE:
<221> NAME/KEY: modified_base
<222> LOCATION: (161)
<223> OTHER INFORMATION: Where n is a, c, g or t
<220> FEATURE:
<221> NAME/KEY: modified_base
<222> LOCATION: (168)
<223> OTHER INFORMATION: Where n is a, c, g or t
<220> FEATURE:
<221> NAME/KEY: modified_base
<222> LOCATION: (183)
<223> OTHER INFORMATION: Where n is a, c, g or t
<220> FEATURE:
<221> NAME/KEY: modified_base
<222> LOCATION: (192)
<223> OTHER INFORMATION: Where n is a, c, g or t
<220> FEATURE:
<221> NAME/KEY: modified_base
<222> LOCATION: (232)
<223> OTHER INFORMATION: Where n is a, c, g or t
<220> FEATURE:
<221> NAME/KEY: modified_base
<222> LOCATION: (251)
<223> OTHER INFORMATION: Where n is a, c, g or t
<220> FEATURE:
<221> NAME/KEY: modified_base
```

```
<222> LOCATION: (308)
<223> OTHER INFORMATION: Where n is a, c, g or t
<220> FEATURE:
<221> NAME/KEY: modified_base
<222> LOCATION: (345)
<223> OTHER INFORMATION: Where n is a, c, g or t
<220> FEATURE:
<221> NAME/KEY: modified_base
<222> LOCATION: (348)
<223> OTHER INFORMATION: Where n is a, c, g or t
<220> FEATURE:
<221> NAME/KEY: modified_base
<222> LOCATION: (354)
<223> OTHER INFORMATION: Where n is a, c, g or t
<220> FEATURE:
<221> NAME/KEY: modified_base
<222> LOCATION: (363)
<223> OTHER INFORMATION: Where n is a, c, g or t
<220> FEATURE:
<221> NAME/KEY: modified_base
<222> LOCATION: (369)
<223> OTHER INFORMATION: Where n is a, c, g or t
<220> FEATURE:
<221> NAME/KEY: modified_base
<222> LOCATION: (391)
<223> OTHER INFORMATION: Where n is a, c, g or t
<220> FEATURE:
<221> NAME/KEY: modified_base
<222> LOCATION: (397)
<223> OTHER INFORMATION: Where n is a, c, g or t
<220> FEATURE:
<221> NAME/KEY: modified_base
<222> LOCATION: (400)
<223> OTHER INFORMATION: Where n is a, c, g or t
<220> FEATURE:
<221> NAME/KEY: modified_base
<222> LOCATION: (401)
<223> OTHER INFORMATION: Where n is a, c, g or t

<400> SEQUENCE: 37
cnnctntgna atggantnnt tgnctaaaan ganttgatga tgatgaaanat ccctangang      60
antaagcatg gancntgatc ntttnctnng cactcccttta cgacacggaa acangnatca    120
ncatgatggt accaganacc ttatcaccna cgcgcacnga nctgactnat tccaaagagt    180
tgnggttacg gncatccggt cattgctcgt gcccattgct gcagggctga tnctactggt    240
gcttattatg ntggccctga ggatgctcca caatgaatat aagcatgctg catgatcagc    300
ggcaacanat gctctgccgt ttgcactaca tctttcacgg acacnatntc gaanacgggc    360
acnttgcana gttagacttg gaatgcatgg ngccggncan n                        401

<210> SEQ ID NO 38
<211> LENGTH: 401
<212> TYPE: DNA
<213> ORGANISM: Human

<400> SEQUENCE: 38
aattggctca ctctctcaag gcaagcactg tctcaaggca gtctcaaggc agagatgaca     60
cagcaaaaaa cagaggggga gaaaaagtc tattattggc ttgtgattta caaaagccaa    120
agtcctttag ataaaaggcc aggagtcgta ccaacataga taccaaatcc aggagaacac    180
agaccagcga taagagggac gcttccccat gacccagacc agcctaaagc ccctgtgggg    240
gcagccagtg gggagctgtc agaccttgga catggtggtc tttgagaatg ggtctgccct    300
tctctccctg accagttggg atagacacct gactggaatc cttgacactg gcaggtgttt    360
ctatgaacag agaggactgt gcctgtcttc ctgaatccca a                        401

<210> SEQ ID NO 39
```

<211> LENGTH: 401
<212> TYPE: DNA
<213> ORGANISM: Human
<220> FEATURE:
<221> NAME/KEY: modified_base
<222> LOCATION: (8)
<223> OTHER INFORMATION: Where n is a, c, g or t
<220> FEATURE:
<221> NAME/KEY: modified_base
<222> LOCATION: (209)
<223> OTHER INFORMATION: Where n is a, c, g or t

<400> SEQUENCE: 39

```
tctggtangg agcaattcta ttatttggca ttgcatggct gggttgaatt aaaacaggga      60
gtgagaacag gtgagtctag aagtccaact ctgaaaagga ccactgtaca tttgaacaca     120
cggctgtgtt aaagatgctg ctaatgtcag tcactgggtg cactaaagga tctcttattt     180
tatgtaaaac gttgggaatg acaagatana actgatactc tggtaagtta ccctctgaag     240
ctacttcttg tgaaatacta atgacagcat catcctgcca agcgaaagag gcaggcataa     300
gcaaggacaa attaaaaggg ggtaagagcc ttatcatgat gaggagtctt gttttgacat     360
cttgggaaaa gctgtccata gtgtgaagtc gtcaatttct c                         401
```

<210> SEQ ID NO 40
<211> LENGTH: 401
<212> TYPE: DNA
<213> ORGANISM: Human

<400> SEQUENCE: 40

```
tctggtcacc caactcttgt ggaagagggg aattgagatc gagtactgaa tatctggcag      60
agaggctgga atccttcagc cccagagccc agggaccact ccagtagatg cagagagggg     120
cctgcccagg ggtcagggca gtgggtatca ctggtgacat caagaatatc agggctgggg     180
aggcatcttt gtttcctggt gccctcctca aagttgctga cactttgggg acggaagggg     240
gtagaagtag ggctgctcct tttggagctg gagggaatag acctggagac agagttgagg     300
cagtcgggct gtccaggttc taagcatcac agcttctgca ctgggctctg aggagattct     360
cagccagagg atcccagcct cctcctccct caaatgtcaa g                         401
```

<210> SEQ ID NO 41
<211> LENGTH: 401
<212> TYPE: DNA
<213> ORGANISM: Human
<220> FEATURE:
<221> NAME/KEY: modified_base
<222> LOCATION: (170)
<223> OTHER INFORMATION: Where n is a, c, g or t
<220> FEATURE:
<221> NAME/KEY: modified_base
<222> LOCATION: (317)
<223> OTHER INFORMATION: Where n is a, c, g or t
<220> FEATURE:
<221> NAME/KEY: modified_base
<222> LOCATION: (334)
<223> OTHER INFORMATION: Where n is a, c, g or t
<220> FEATURE:
<221> NAME/KEY: modified_base
<222> LOCATION: (364)
<223> OTHER INFORMATION: Where n is a, c, g or t

<400> SEQUENCE: 41

```
ctggactaaa aatgtccact atggggtgca ctctacagtt tttgaaatgc taggaggcag      60
aaggggcaga gagtaaaaaa catgacctgg tagaaggaag agaggcaaag gaaactaggt     120
ggggaggatc aattagagag gaggcacctg ggatccacct tcttccttan gtccctcct     180
```

```
ccatcagcaa aggagcactt ctctaatcat gccctcccga agactggctg ggagaaggtt      240
taaaaacaaa aaatccagga gtaagagcct taggtcagtt tgaaattgga gacaaactgt      300
ctggcaaagg gtgcganagg gagcttgtgc tcangagtcc agcccgtcca gcctcggggt      360
gtangtttct gaagtgtgcc attggggcct caccttctct g                         401
```

<210> SEQ ID NO 42
<211> LENGTH: 310
<212> TYPE: DNA
<213> ORGANISM: Human

<400> SEQUENCE: 42

```
ggttcgacaa atccccaaaa atggcaaatt aagccctgtg acaaaataag ttattggatc      60
atacagaaat agcccaaatc tggaaatttt gaattaaaat tgtaatcctg taaaacaagt      120
tttggggtga atggatttct ttaataccaa taatattttt aattcccacc acagatggat      180
ttgctgaata tgctaatgct gtgaatgaga aacaattttt ggggtaggta tacccacaag      240
taatctgatg acaaaataaa ccacagactg atgtcaaatg acaaaaaac tgaaaatatg      300
ctgtgagaaa                                                            310
```

<210> SEQ ID NO 43
<211> LENGTH: 401
<212> TYPE: DNA
<213> ORGANISM: Human

<400> SEQUENCE: 43

```
aggtcactta cacttgtgac cagtgtgggg cagagaccta ccagccgatc cagtctccca      60
ctttcatgcc tctgatcatg tgcccaagcc aggagtgcca aaccaaccgc tcaggagggc      120
ggctgtatct gcagacacgg ggctccagat tcatcaaatt ccaggagatg aagatgcaag      180
aacatagtga tcaggtgcct gtgggaaata tccctcgtag tatcacggtg ctggtagaag      240
gagagaacac aaggattgcc cagcctggag accacgtcag cgtcactggt atttttcttgc      300
caatcctgcg cactgggttc cgacaggtgg tacagggttt actctcagaa acctacctgg      360
aagcccatcg gattgtgaag atgaacaaga gtgaggatga t                         401
```

<210> SEQ ID NO 44
<211> LENGTH: 401
<212> TYPE: DNA
<213> ORGANISM: Human

<400> SEQUENCE: 44

```
atccctgtaa gtctattaaa tgtaaataat acatacttta caacttctct tagtcggccc      60
ttggcagatt aaatctttgc aaaattccat atgtgctatt gaaaatgaa ataaaacctc       120
agatgtctga attcttattt caaatacagt tatataatta ttttaaatta caatatacaa      180
tttctgttaa atacaactgt taagggattc tgagaacaat tataagatta taataatata      240
tacaaactaa cttctgaaat gacatggggtt gtttccttcc caccctccta ccctctcaaa    300
gagttttttgc atttgctgtt cctggttgca aaaggcaaaa gaaaatctaa aaatagtctg    360
tgtgtgtcca cgacatgctc gctcctttga gaatctcaaa c                         401
```

<210> SEQ ID NO 45
<211> LENGTH: 401
<212> TYPE: DNA
<213> ORGANISM: Human
<220> FEATURE:

<221> NAME/KEY: modified_base
<222> LOCATION: (212)
<223> OTHER INFORMATION: Where n is a, c, g or t
<220> FEATURE:
<221> NAME/KEY: modified_base
<222> LOCATION: (224)
<223> OTHER INFORMATION: Where n is a, c, g or t

<400> SEQUENCE: 45

```
gtgcctgctg cctggcagcc tggccctgcc gctgcctcag gaggcgggag gcatgagtga      60
gctacagtgg gaacaggctc aggactatct caagagattt tatctctatg actcagaaac     120
aaaaaatgcc aacagtttag aagccaaact caaggagatg caaaaaattc tttggcctac     180
ctatactgga atggtaaact cccgcgtcat anaaataatg caanaagccc agatgtggag     240
tgccagatgt tgcagaatac tcactatttc caaatagccc aaaatggact tccaaagtgg     300
tcacctacag gatcgtatca tatactcgag acttaccgca tattacagtg gatcgattag     360
tgtcaaaggc tttaaacatg tggggcaaag agatccccct g                         401
```

<210> SEQ ID NO 46
<211> LENGTH: 401
<212> TYPE: DNA
<213> ORGANISM: Human
<220> FEATURE:
<221> NAME/KEY: modified_base
<222> LOCATION: (70)
<223> OTHER INFORMATION: Where n is a, c, g or t
<220> FEATURE:
<221> NAME/KEY: modified_base
<222> LOCATION: (182)
<223> OTHER INFORMATION: Where n is a, c, g or t

<400> SEQUENCE: 46

```
gtcagaattg tctttctgaa aggaagcact cggaatcctt ccgaactttc caagtccatc      60
catgattcan agatactgcc ttctctctct ctgggatttt atgtgtttct gatagtgaat     120
tgttgatgta tttgctactt tgcttctttt ctctttcaag acttgatcat tttatatgct     180
gnttggagaa aaaagaaact tttggtagca aggaggtttc aagaaatgat tttggatttt     240
ctgctgcgga atttctcggc acctacctgt agtatggggc acttggtttg ttgcagagt      300
aagaaggtgg aagaatgagc tgtacttggt taagcagttg aaacctttt tgagcaggat     360
ctgtaaaagc ataattgaat ttgtttcacc cccgtggatt c                         401
```

<210> SEQ ID NO 47
<211> LENGTH: 401
<212> TYPE: DNA
<213> ORGANISM: Human

<400> SEQUENCE: 47

```
ggtctgcagc aatgcacttc aaccatacat actgcttcca ctagctaata ccaaatgcag      60
gttctcagat ccagacaaat ggaggaaaag aacatttatg cttccgtttc agaaagccaa     120
gtcgtagttt tggcccttcc tttctctaaa gtttattccc aaaaacaggt agcattcctg     180
attgggcaga gaagaggata ttttcagccc acatctgctg caggtatgtc attttctccc     240
atcttcactg tgactagtaa agatctcacc acttctcttt ggaatttcca actttgcttg     300
tgattgaatg tcacttcgtg aatttgtatt atgtcagatc acttggcatt gctcttccat     360
atgcatcaag ttgccaggca ctaaacccaa tgttcatgaa c                         401
```

<210> SEQ ID NO 48
<211> LENGTH: 430

<212> TYPE: DNA
<213> ORGANISM: Human

<400> SEQUENCE: 48
acataacttg taaactttt ctgcttgggg gctgtaacag acagaagagt aaagactaca      60
aggattttct gaagatgctt caatgaaaat catcatttcc tctttagtca tcccaagtct    120
tggtttgaaa acttgggca tggacttata cagaccttga accaccactg acttatcatt    180
gggtggcaga ccttgaaacc aagctctctg tgttacttct gaaagtgcat caattctgat    240
ttggctaaga acagaagaca aatactggga tcgtgattct gtgttatact ctagccacag    300
catagcagct tctcgaacgg tttcttcctt ttctacattt aaattgtcac tactgagaat    360
atctatcagt aggtcatgtg acagacctgc cccggggccg gcccgctcga tgcttgccga    420
atatcatggt                                                           430

<210> SEQ ID NO 49
<211> LENGTH: 57
<212> TYPE: DNA
<213> ORGANISM: Human
<220> FEATURE:
<221> NAME/KEY: modified_base
<222> LOCATION: (17)
<223> OTHER INFORMATION: Where n is a, c, g or t
<220> FEATURE:
<221> NAME/KEY: modified_base
<222> LOCATION: (44)
<223> OTHER INFORMATION: Where n is a, c, g or t
<220> FEATURE:
<221> NAME/KEY: modified_base
<222> LOCATION: (49)
<223> OTHER INFORMATION: Where n is a, c, g or t

<400> SEQUENCE: 49
ggtattaaca atatcangca ctcattcttc ccctcttatg aaanggatna attttta        57

<210> SEQ ID NO 50
<211> LENGTH: 327
<212> TYPE: DNA
<213> ORGANISM: Human
<220> FEATURE:
<221> NAME/KEY: modified_base
<222> LOCATION: (6)
<223> OTHER INFORMATION: Where n is a, c, g or t
<220> FEATURE:
<221> NAME/KEY: modified_base
<222> LOCATION: (10)
<223> OTHER INFORMATION: Where n is a, c, g or t
<220> FEATURE:
<221> NAME/KEY: modified_base
<222> LOCATION: (20)
<223> OTHER INFORMATION: Where n is a, c, g or t
<220> FEATURE:
<221> NAME/KEY: modified_base
<222> LOCATION: (22)
<223> OTHER INFORMATION: Where n is a, c, g or t
<220> FEATURE:
<221> NAME/KEY: modified_base
<222> LOCATION: (25)
<223> OTHER INFORMATION: Where n is a, c, g or t
<220> FEATURE:
<221> NAME/KEY: modified_base
<222> LOCATION: (28)
<223> OTHER INFORMATION: Where n is a, c, g or t
<220> FEATURE:
<221> NAME/KEY: modified_base
<222> LOCATION: (30)
<223> OTHER INFORMATION: Where n is a, c, g or t
<220> FEATURE:
<221> NAME/KEY: modified_base
<222> LOCATION: (37)

-continued

```
<223> OTHER INFORMATION: Where n is a, c, g or t
<220> FEATURE:
<221> NAME/KEY: modified_base
<222> LOCATION: (40)
<223> OTHER INFORMATION: Where n is a, c, g or t
<220> FEATURE:
<221> NAME/KEY: modified_base
<222> LOCATION: (41)
<223> OTHER INFORMATION: Where n is a, c, g or t
<220> FEATURE:
<221> NAME/KEY: modified_base
<222> LOCATION: (42)
<223> OTHER INFORMATION: Where n is a, c, g or t
<220> FEATURE:
<221> NAME/KEY: modified_base
<222> LOCATION: (51)
<223> OTHER INFORMATION: Where n is a, c, g or t
<220> FEATURE:
<221> NAME/KEY: modified_base
<222> LOCATION: (58)
<223> OTHER INFORMATION: Where n is a, c, g or t
<220> FEATURE:
<221> NAME/KEY: modified_base
<222> LOCATION: (59)
<223> OTHER INFORMATION: Where n is a, c, g or t
<220> FEATURE:
<221> NAME/KEY: modified_base
<222> LOCATION: (68)
<223> OTHER INFORMATION: Where n is a, c, g or t
<220> FEATURE:
<221> NAME/KEY: modified_base
<222> LOCATION: (69)
<223> OTHER INFORMATION: Where n is a, c, g or t
<220> FEATURE:
<221> NAME/KEY: modified_base
<222> LOCATION: (70)
<223> OTHER INFORMATION: Where n is a, c, g or t
<220> FEATURE:
<221> NAME/KEY: modified_base
<222> LOCATION: (75)
<223> OTHER INFORMATION: Where n is a, c, g or t
<220> FEATURE:
<221> NAME/KEY: modified_base
<222> LOCATION: (76)
<223> OTHER INFORMATION: Where n is a, c, g or t
<220> FEATURE:
<221> NAME/KEY: modified_base
<222> LOCATION: (79)
<223> OTHER INFORMATION: Where n is a, c, g or t
<220> FEATURE:
<221> NAME/KEY: modified_base
<222> LOCATION: (91)
<223> OTHER INFORMATION: Where n is a, c, g or t
<220> FEATURE:
<221> NAME/KEY: modified_base
<222> LOCATION: (95)
<223> OTHER INFORMATION: Where n is a, c, g or t
<220> FEATURE:
<221> NAME/KEY: modified_base
<222> LOCATION: (108)
<223> OTHER INFORMATION: Where n is a, c, g or t
<220> FEATURE:
<221> NAME/KEY: modified_base
<222> LOCATION: (109)
<223> OTHER INFORMATION: Where n is a, c, g or t
<220> FEATURE:
<221> NAME/KEY: modified_base
<222> LOCATION: (111)
<223> OTHER INFORMATION: Where n is a, c, g or t
<220> FEATURE:
<221> NAME/KEY: modified_base
<222> LOCATION: (142)
<223> OTHER INFORMATION: Where n is a, c, g or t
<220> FEATURE:
<221> NAME/KEY: modified_base
<222> LOCATION: (146)
<223> OTHER INFORMATION: Where n is a, c, g or t
<220> FEATURE:
<221> NAME/KEY: modified_base
```

<222> LOCATION: (180)
<223> OTHER INFORMATION: Where n is a, c, g or t
<220> FEATURE:
<221> NAME/KEY: modified_base
<222> LOCATION: (200)
<223> OTHER INFORMATION: Where n is a, c, g or t
<220> FEATURE:
<221> NAME/KEY: modified_base
<222> LOCATION: (201)
<223> OTHER INFORMATION: Where n is a, c, g or t
<220> FEATURE:
<221> NAME/KEY: modified_base
<222> LOCATION: (213)
<223> OTHER INFORMATION: Where n is a, c, g or t
<220> FEATURE:
<221> NAME/KEY: modified_base
<222> LOCATION: (218)
<223> OTHER INFORMATION: Where n is a, c, g or t
<220> FEATURE:
<221> NAME/KEY: modified_base
<222> LOCATION: (233)
<223> OTHER INFORMATION: Where n is a, c, g or t
<220> FEATURE:
<221> NAME/KEY: modified_base
<222> LOCATION: (235)
<223> OTHER INFORMATION: Where n is a, c, g or t
<220> FEATURE:
<221> NAME/KEY: modified_base
<222> LOCATION: (247)
<223> OTHER INFORMATION: Where n is a, c, g or t
<220> FEATURE:
<221> NAME/KEY: modified_base
<222> LOCATION: (265)
<223> OTHER INFORMATION: Where n is a, c, g or t
<220> FEATURE:
<221> NAME/KEY: modified_base
<222> LOCATION: (290)
<223> OTHER INFORMATION: Where n is a, c, g or t
<220> FEATURE:
<221> NAME/KEY: modified_base
<222> LOCATION: (299)
<223> OTHER INFORMATION: Where n is a, c, g or t
<220> FEATURE:
<221> NAME/KEY: modified_base
<222> LOCATION: (306)
<223> OTHER INFORMATION: Where n is a, c, g or t

<400> SEQUENCE: 50
gatggnggtn tccacaagan tnaangtncn tattaantan nncttgtaga nccacttnna      60
ttaattgnnn tatgnntgnc cttctggtgg ntgtngaagc ttcatatnnt nttttggacat    120 cattacacgt cttagctctt tnaagnacaa ctttaatgct atatgaattt tgccattttn    180
gctaacactg gtatgctccn ngcatccacc atnccacntg gaattattta ttncnttcat    240
attaatnttt tgtttaccaa atctnacttg acccgaacga aactttctgn gtattttang    300
gccccnccat tcttactttt caagcct                                         327

<210> SEQ ID NO 51
<211> LENGTH: 236
<212> TYPE: DNA
<213> ORGANISM: Human

<400> SEQUENCE: 51
cgtctcgaag aagcgctgca ggccgatgat ggactgcacg tctgccttgt cctcagttaa     60
cttgttgaat tgcttgaaca tgcggcccac atcctgggca aactcctgtg gggagctgta    120
gggaggtgac aacttctcct ggaggcgggc acggatcagg gtcagatcca ggtgccacc    180 gggctggtcc aggagaagg tggagtcgta gccagacctg cccgggcggc cgctcg         236

<210> SEQ ID NO 52

```
<211> LENGTH: 291
<212> TYPE: DNA
<213> ORGANISM: Human
<220> FEATURE:
<221> NAME/KEY: modified_base
<222> LOCATION: (168)
<223> OTHER INFORMATION: Where n is a, c, g or t
<220> FEATURE:
<221> NAME/KEY: modified_base
<222> LOCATION: (197)
<223> OTHER INFORMATION: Where n is a, c, g or t
<220> FEATURE:
<221> NAME/KEY: modified_base
<222> LOCATION: (202)
<223> OTHER INFORMATION: Where n is a, c, g or t
<220> FEATURE:
<221> NAME/KEY: modified_base
<222> LOCATION: (209)
<223> OTHER INFORMATION: Where n is a, c, g or t
<220> FEATURE:
<221> NAME/KEY: modified_base
<222> LOCATION: (218)
<223> OTHER INFORMATION: Where n is a, c, g or t
<220> FEATURE:
<221> NAME/KEY: modified_base
<222> LOCATION: (257)
<223> OTHER INFORMATION: Where n is a, c, g or t
<220> FEATURE:
<221> NAME/KEY: modified_base
<222> LOCATION: (271)
<223> OTHER INFORMATION: Where n is a, c, g or t
<220> FEATURE:
<221> NAME/KEY: modified_base
<222> LOCATION: (287)
<223> OTHER INFORMATION: Where n is a, c, g or t

<400> SEQUENCE: 52
ctcacatcct gggtccggct gtagagctgc accatggtgc tgagcgcccc ctccagctcc      60
ttgtagatgt aaaggacggc gaaggagctg tagtctgtgt ccacgatgcg cacgtccagg     120
tagcccaagg ccgggactct gaagttgtcc ctcggagccc accttcangt actcgggcat    180
ccacctggtt acagccnttc gncctcggna actccatntg gactttacag gccgccctcc    240
tctgtgggcc tgatggncct tgcaggacat nggaacacgg gagctcnctt t             291

<210> SEQ ID NO 53
<211> LENGTH: 95
<212> TYPE: DNA
<213> ORGANISM: Human
<220> FEATURE:
<221> NAME/KEY: modified_base
<222> LOCATION: (37)
<223> OTHER INFORMATION: Where n is a, c, g or t
<220> FEATURE:
<221> NAME/KEY: modified_base
<222> LOCATION: (60)
<223> OTHER INFORMATION: Where n is a, c, g or t
<220> FEATURE:
<221> NAME/KEY: modified_base
<222> LOCATION: (73)
<223> OTHER INFORMATION: Where n is a, c, g or t
<220> FEATURE:
<221> NAME/KEY: modified_base
<222> LOCATION: (76)
<223> OTHER INFORMATION: Where n is a, c, g or t
<220> FEATURE:
<221> NAME/KEY: modified_base
<222> LOCATION: (92)
<223> OTHER INFORMATION: Where n is a, c, g or t

<400> SEQUENCE: 53
gtctgtgcag tttctgacac ttgttgttga acatggntaa atacaatggg tatcgctgan     60
cactaagttg tanaanttaa caaatgtgct gnttg                                95
```

<210> SEQ ID NO 54
<211> LENGTH: 66
<212> TYPE: DNA
<213> ORGANISM: Human
<220> FEATURE:
<221> NAME/KEY: modified_base
<222> LOCATION: (4)
<223> OTHER INFORMATION: Where n is a, c, g or t
<220> FEATURE:
<221> NAME/KEY: modified_base
<222> LOCATION: (8)
<223> OTHER INFORMATION: Where n is a, c, g or t
<220> FEATURE:
<221> NAME/KEY: modified_base
<222> LOCATION: (11)
<223> OTHER INFORMATION: Where n is a, c, g or t
<220> FEATURE:
<221> NAME/KEY: modified_base
<222> LOCATION: (13)
<223> OTHER INFORMATION: Where n is a, c, g or t
<220> FEATURE:
<221> NAME/KEY: modified_base
<222> LOCATION: (26)
<223> OTHER INFORMATION: Where n is a, c, g or t
<220> FEATURE:
<221> NAME/KEY: modified_base
<222> LOCATION: (27)
<223> OTHER INFORMATION: Where n is a, c, g or t
<220> FEATURE:
<221> NAME/KEY: modified_base
<222> LOCATION: (35)
<223> OTHER INFORMATION: Where n is a, c, g or t
<220> FEATURE:
<221> NAME/KEY: modified_base
<222> LOCATION: (38)
<223> OTHER INFORMATION: Where n is a, c, g or t
<220> FEATURE:
<221> NAME/KEY: modified_base
<222> LOCATION: (43)
<223> OTHER INFORMATION: Where n is a, c, g or t
<220> FEATURE:
<221> NAME/KEY: modified_base
<222> LOCATION: (47)
<223> OTHER INFORMATION: Where n is a, c, g or t
<220> FEATURE:
<221> NAME/KEY: modified_base
<222> LOCATION: (57)
<223> OTHER INFORMATION: Where n is a, c, g or t

<400> SEQUENCE: 54
cctnaatnat ntnaatggta tcaatnnccc tgaangangg gancggngga agccggnttt    60
gtccgg                                                              66

<210> SEQ ID NO 55
<211> LENGTH: 265
<212> TYPE: DNA
<213> ORGANISM: Human
<220> FEATURE:
<221> NAME/KEY: modified_base
<222> LOCATION: (25)
<223> OTHER INFORMATION: Where n is a, c, g or t
<220> FEATURE:
<221> NAME/KEY: modified_base
<222> LOCATION: (223)
<223> OTHER INFORMATION: Where n is a, c, g or t
<220> FEATURE:
<221> NAME/KEY: modified_base
<222> LOCATION: (241)
<223> OTHER INFORMATION: Where n is a, c, g or t
<220> FEATURE:
<221> NAME/KEY: modified_base
<222> LOCATION: (254)
<223> OTHER INFORMATION: Where n is a, c, g or t
<220> FEATURE:

<221> NAME/KEY: modified_base
<222> LOCATION: (259)
<223> OTHER INFORMATION: Where n is a, c, g or t

<400> SEQUENCE: 55

```
atctttcttc tcagtgcctt ggccntgttg agtctatctg gtaacactgg agctgactcc      60
ctgggaagag aggccaaatg ttacaatgaa cttaatggat gcaccaagat atatgaccct     120
gtctgtggga ctgatggaaa tacttatccc aatgaatgcc gtgttatgtt tttgaaaatc     180
ggaaacgcca gacttctatc ctcattcaaa aatctgggcc ttnctgaaaa ccagggtttt     240
naaaatccca ttcnggtcnc cggcg                                           265
```

<210> SEQ ID NO 56
<211> LENGTH: 420
<212> TYPE: DNA
<213> ORGANISM: Human
<220> FEATURE:
<221> NAME/KEY: modified_base
<222> LOCATION: (85)
<223> OTHER INFORMATION: Where n is a, c, g or t
<220> FEATURE:
<221> NAME/KEY: modified_base
<222> LOCATION: (164)
<223> OTHER INFORMATION: Where n is a, c, g or t
<220> FEATURE:
<221> NAME/KEY: modified_base
<222> LOCATION: (198)
<223> OTHER INFORMATION: Where n is a, c, g or t
<220> FEATURE:
<221> NAME/KEY: modified_base
<222> LOCATION: (228)
<223> OTHER INFORMATION: Where n is a, c, g or t
<220> FEATURE:
<221> NAME/KEY: modified_base
<222> LOCATION: (257)
<223> OTHER INFORMATION: Where n is a, c, g or t
<220> FEATURE:
<221> NAME/KEY: modified_base
<222> LOCATION: (261)
<223> OTHER INFORMATION: Where n is a, c, g or t
<220> FEATURE:
<221> NAME/KEY: modified_base
<222> LOCATION: (283)
<223> OTHER INFORMATION: Where n is a, c, g or t
<220> FEATURE:
<221> NAME/KEY: modified_base
<222> LOCATION: (298)
<223> OTHER INFORMATION: Where n is a, c, g or t
<220> FEATURE:
<221> NAME/KEY: modified_base
<222> LOCATION: (326)
<223> OTHER INFORMATION: Where n is a, c, g or t
<220> FEATURE:
<221> NAME/KEY: modified_base
<222> LOCATION: (385)
<223> OTHER INFORMATION: Where n is a, c, g or t
<220> FEATURE:
<221> NAME/KEY: modified_base
<222> LOCATION: (390)
<223> OTHER INFORMATION: Where n is a, c, g or t

<400> SEQUENCE: 56

```
gagcggccgc ccgggcaggt cctcgcggtg acctgatggg atttcaaaac cttggttctc      60
agcaaggccc agatttttga atgangatag aagtctggcg tttccgattt tcaaaacata     120
acacgcattc attgggataa gtatttccat cagtcccaca gacngggtca tatatcttgg     180
gtgcatccat taagttcntt tgttaacatt tgggcctctc tttcccangg gaattcagct     240
cccagttgtt taccaanatt naactccacc ggggccaaag gcnctgaaa aaaaaaanaa      300
ttccttgttt accttccttg ggcttnaagt tctggcgtcc aaaagttcaa tttgaaaact     360
```

```
gcaccgcact taccacgtct cttcnagaan cctggggaca cctcggccgc gaccacgcta      420

<210> SEQ ID NO 57
<211> LENGTH: 170
<212> TYPE: DNA
<213> ORGANISM: Human

<400> SEQUENCE: 57
gaagcggagt tgcagcgcct ggtggccgcc gagcagcaga aggcgcagtt tactgcacag      60
gtgcatcact tcatggagtt atgttgggat aaatgtgtgg agaagccagg gaatcgccta     120
gactctcgca ctgaaaattg tctctccaga cctcggccgc gaccacgcta               170

<210> SEQ ID NO 58
<211> LENGTH: 193
<212> TYPE: DNA
<213> ORGANISM: Human

<400> SEQUENCE: 58
attttcagtg cgagagtcta ggcgattccc tggcttctcc acacatttat cccaacataa      60
ctccatgaag tgatgcacct gtgcagtaaa ctgcgccttc tgctgctcgg cggccaccag     120
gcgctgcaac tccgcttcat cggcttcgcc cagctccgcc attgttcgcc acctgcccgg     180
gcggccgctc gaa                                                        193

<210> SEQ ID NO 59
<211> LENGTH: 229
<212> TYPE: DNA
<213> ORGANISM: Human

<400> SEQUENCE: 59
cgcaactctc gagcatttat atacaatagc aaatcatcca gtgtgttgta cagtctataa      60
tactccaaca gtctcccatc tgtattcaat ggcgccaccc aatacagtcc tttgtttgga     120
tgctggggag agtaatccct accccaagca ccatatagat aagaaaaccc tctccagttg     180
agctgaacca cagacggttt gctgatacct gcccgggcgg ccgctcgaa                229

<210> SEQ ID NO 60
<211> LENGTH: 340
<212> TYPE: DNA
<213> ORGANISM: Human

<400> SEQUENCE: 60
tcgagcggcc gcccgggcag gtcctctaaa gatcaaaaca ccctgtcgt ccaccctcct       60 cccactccag ggaagctgtg gtcatggtgg tgtggtgaac atcagcaaac cgtctgtggt     120
tcagctcaac tggagagggt tttcttatct atatggtgct tggggtaggg attactctcc     180
ccagcatcca aacaaaggac tgtattgggt ggcgccattg aatacagatg ggaaactgtt     240
ggagtattat aaactggtac aacacactgg atgatttgct attgtatata aatgctcgag     300
aattgcggat cacctatgga cctcggccgc gaccacgctg                           340

<210> SEQ ID NO 61
<211> LENGTH: 179
<212> TYPE: DNA
<213> ORGANISM: Human
<220> FEATURE:
<221> NAME/KEY: modified_base
<222> LOCATION: (16)
<223> OTHER INFORMATION: Where n is a, c, g or t
<220> FEATURE:
```

```
<221> NAME/KEY: modified_base
<222> LOCATION: (176)
<223> OTHER INFORMATION: Where n is a, c, g or t
<220> FEATURE:
<221> NAME/KEY: modified_base
<222> LOCATION: (96)
<223> OTHER INFORMATION: Where n is a, c, g or t
<220> FEATURE:
<221> NAME/KEY: modified_base
<222> LOCATION: (110)
<223> OTHER INFORMATION: Where n is a, c, g or t
<220> FEATURE:
<221> NAME/KEY: modified_base
<222> LOCATION: (112)
<223> OTHER INFORMATION: Where n is a, c, g or t
<220> FEATURE:
<221> NAME/KEY: modified_base
<222> LOCATION: (122)
<223> OTHER INFORMATION: Where n is a, c, g or t
<220> FEATURE:
<221> NAME/KEY: modified_base
<222> LOCATION: (138)
<223> OTHER INFORMATION: Where n is a, c, g or t
<220> FEATURE:
<221> NAME/KEY: modified_base
<222> LOCATION: (140)
<223> OTHER INFORMATION: Where n is a, c, g or t
<220> FEATURE:
<221> NAME/KEY: modified_base
<222> LOCATION: (143)
<223> OTHER INFORMATION: Where n is a, c, g or t
<220> FEATURE:
<221> NAME/KEY: modified_base
<222> LOCATION: (155)
<223> OTHER INFORMATION: Where n is a, c, g or t
<220> FEATURE:
<221> NAME/KEY: modified_base
<222> LOCATION: (161)
<223> OTHER INFORMATION: Where n is a, c, g or t
<220> FEATURE:
<221> NAME/KEY: modified_base
<222> LOCATION: (163)
<223> OTHER INFORMATION: Where n is a, c, g or t
<220> FEATURE:
<221> NAME/KEY: modified_base
<222> LOCATION: (175)
<223> OTHER INFORMATION: Where n is a, c, g or t
<220> FEATURE:
<221> NAME/KEY: modified_base
<222> LOCATION: (178)
<223> OTHER INFORMATION: Where n is a, c, g or t

<400> SEQUENCE: 61
tttttgtgac ggacgnttgg agtacatgtc ccaggatcac atccagcagc tagagtggct      60
gggacaagct ggcggnggcc aagcactgtt gaaacnatag gggtctgggn gnactcgggt     120
tnaagtggtt ggtccgantn ttnataacct tgtcngaacc nancatctcg gttgncang     179

<210> SEQ ID NO 62
<211> LENGTH: 78
<212> TYPE: DNA
<213> ORGANISM: Human
<220> FEATURE:
<221> NAME/KEY: modified_base
<222> LOCATION: (51)
<223> OTHER INFORMATION: Where n is a, c, g or t
<220> FEATURE:
<221> NAME/KEY: modified_base
<222> LOCATION: (72)
<223> OTHER INFORMATION: Where n is a, c, g or t

<400> SEQUENCE: 62
agggcgttcg taacgggaat gccgaagcgt gggaaaaagg gagcggtggc nggaagacgg      60
ggatgagctt angacaga                                                   78
```

<210> SEQ ID NO 63
<211> LENGTH: 410
<212> TYPE: DNA
<213> ORGANISM: Human
<220> FEATURE:
<221> NAME/KEY: modified_base
<222> LOCATION: (48)
<223> OTHER INFORMATION: Where n is a, c, g or t
<220> FEATURE:
<221> NAME/KEY: modified_base
<222> LOCATION: (95)
<223> OTHER INFORMATION: Where n is a, c, g or t
<220> FEATURE:
<221> NAME/KEY: modified_base
<222> LOCATION: (182)
<223> OTHER INFORMATION: Where n is a, c, g or t
<220> FEATURE:
<221> NAME/KEY: modified_base
<222> LOCATION: (290)
<223> OTHER INFORMATION: Where n is a, c, g or t
<220> FEATURE:
<221> NAME/KEY: modified_base
<222> LOCATION: (314)
<223> OTHER INFORMATION: Where n is a, c, g or t
<220> FEATURE:
<221> NAME/KEY: modified_base
<222> LOCATION: (350)
<223> OTHER INFORMATION: Where n is a, c, g or t
<220> FEATURE:
<221> NAME/KEY: modified_base
<222> LOCATION: (365)
<223> OTHER INFORMATION: Where n is a, c, g or t
<220> FEATURE:
<221> NAME/KEY: modified_base
<222> LOCATION: (380)
<223> OTHER INFORMATION: Where n is a, c, g or t

<400> SEQUENCE: 63

```
cccagttact tggggaggct gaggcaggga gaatcctttg aacccggngg gtgggaggtt      60
gcagtgagcc cgagatagca ccattgcact tccancatgg ggtggacaga gtgagactct     120
atctcaaaaa aaaagaaaag aaaaggaaag agattagatt aagattaagt acctacttcc     180
tntcccattt caagtcctga aaatagagga tcagaaatgt tgaggaattc tttaggatag     240
aaagggagat gggattttac ttatggggaa agaccgcaaa taaagactgn aacttaacca     300
cattccccaa gtgnaaggtg ttacccaaga agtaggaacc cttttggctn ttaccttacc     360
ttccngaaaa aaacttattn cttaaaatgg aaacccttaa agcccgggca               410
```

<210> SEQ ID NO 64
<211> LENGTH: 199
<212> TYPE: DNA
<213> ORGANISM: Human
<220> FEATURE:
<221> NAME/KEY: modified_base
<222> LOCATION: (153)
<223> OTHER INFORMATION: Where n is a, c, g or t
<220> FEATURE:
<221> NAME/KEY: modified_base
<222> LOCATION: (156)
<223> OTHER INFORMATION: Where n is a, c, g or t
<220> FEATURE:
<221> NAME/KEY: modified_base
<222> LOCATION: (158)
<223> OTHER INFORMATION: Where n is a, c, g or t
<220> FEATURE:
<221> NAME/KEY: modified_base
<222> LOCATION: (162)
<223> OTHER INFORMATION: Where n is a, c, g or t
<220> FEATURE:
<221> NAME/KEY: modified_base
<222> LOCATION: (170)

```
<223> OTHER INFORMATION: Where n is a, c, g or t
<220> FEATURE:
<221> NAME/KEY: modified_base
<222> LOCATION: (171)
<223> OTHER INFORMATION: Where n is a, c, g or t
<220> FEATURE:
<221> NAME/KEY: modified_base
<222> LOCATION: (184)
<223> OTHER INFORMATION: Where n is a, c, g or t
<220> FEATURE:
<221> NAME/KEY: modified_base
<222> LOCATION: (192)
<223> OTHER INFORMATION: Where n is a, c, g or t

<400> SEQUENCE: 64
cttgttctca aaaggtcaa agggagcccg acgaggaata aatagcaatg ccctgaattc     60
caactgacct tctacagaaa agtgcttgac tgccaagtgg tcttcccagt cattagtgag    120
gctcttgtag aattctccat actcctcttg ggngangnca tnagggtttn nggcccaaat   180
aggntgggcc tngttaagt                                                 199

<210> SEQ ID NO 65
<211> LENGTH: 125
<212> TYPE: DNA
<213> ORGANISM: Human
<220> FEATURE:
<221> NAME/KEY: modified_base
<222> LOCATION: (115)
<223> OTHER INFORMATION: Where n is a, c, g or t
<220> FEATURE:
<221> NAME/KEY: modified_base
<222> LOCATION: (118)
<223> OTHER INFORMATION: Where n is a, c, g or t
<220> FEATURE:
<221> NAME/KEY: modified_base
<222> LOCATION: (120)
<223> OTHER INFORMATION: Where n is a, c, g or t

<400> SEQUENCE: 65
agcggtacag ttctgtcctg gcatcatcat tcattgtagt atggtcaata ggtgccatga    60
aactcagtag cttgctaagg acatgaaacc gaagtttcct gcctttgctg gcctngtngn   120
gggta                                                                125

<210> SEQ ID NO 66
<211> LENGTH: 204
<212> TYPE: DNA
<213> ORGANISM: Human

<400> SEQUENCE: 66
attcagaatt ctggcatcgg tatttctata aagtccatca gttagagcag gagcaggccc    60
ggagggacgc cctgaagcag cgggcggaac agagcatctc tgaagagccc ggctgggagg   120
aggaggaaga ggagctcatg ggcatttcac ccatatctcc aaaagaggca aaggttcctg   180
tggacctcgg ccgcgaccac gcta                                           204

<210> SEQ ID NO 67
<211> LENGTH: 383
<212> TYPE: DNA
<213> ORGANISM: Human
<220> FEATURE:
<221> NAME/KEY: modified_base
<222> LOCATION: (32)
<223> OTHER INFORMATION: Where n is a, c, g or t
<220> FEATURE:
<221> NAME/KEY: modified_base
<222> LOCATION: (46)
<223> OTHER INFORMATION: Where n is a, c, g or t
```

<220> FEATURE:
<221> NAME/KEY: modified_base
<222> LOCATION: (59)
<223> OTHER INFORMATION: Where n is a, c, g or t
<220> FEATURE:
<221> NAME/KEY: modified_base
<222> LOCATION: (132)
<223> OTHER INFORMATION: Where n is a, c, g or t
<220> FEATURE:
<221> NAME/KEY: modified_base
<222> LOCATION: (190)
<223> OTHER INFORMATION: Where n is a, c, g or t
<220> FEATURE:
<221> NAME/KEY: modified_base
<222> LOCATION: (234)
<223> OTHER INFORMATION: Where n is a, c, g or t
<220> FEATURE:
<221> NAME/KEY: modified_base
<222> LOCATION: (264)
<223> OTHER INFORMATION: Where n is a, c, g or t
<220> FEATURE:
<221> NAME/KEY: modified_base
<222> LOCATION: (272)
<223> OTHER INFORMATION: Where n is a, c, g or t

<400> SEQUENCE: 67
tcagggcctc caggcagcca gttttgcagg anattcagca cctagngtct tcctgcctna      60
cgctcccaag aacctgctcc tgcaggggga acatcagaac tcgtccttga tgtcaaaatg     120
gggctggtct tnaggcttga agtccaggtt agggctgcca tcctcattga gaattctccg     180
ggcagtgtan ccgacgatgg ggtatttggc tttgtacact ttggtgaaaa cctnatccag     240
ggcctccagt tccttggccg tganacccgt antgtcatgg gtgaggtctg caggatccaa     300
ggacatcttg gctacccctc tagtggagtc cttccccgtc aaggcattgt aagggctcc      360 tcgtccataa aactccttttt cgg                                            383

<210> SEQ ID NO 68
<211> LENGTH: 99
<212> TYPE: DNA
<213> ORGANISM: Human

<400> SEQUENCE: 68
tcacatctcc ttttttttt aacttttca aattttgtg ttaaatagaa ggctaaaggg      60
ttagatttaa gtttctgcta cattgaccct atttaccta                            99

<210> SEQ ID NO 69
<211> LENGTH: 37
<212> TYPE: DNA
<213> ORGANISM: Human
<220> FEATURE:
<221> NAME/KEY: modified_base
<222> LOCATION: (10)
<223> OTHER INFORMATION: Where n is a, c, g or t
<220> FEATURE:
<221> NAME/KEY: modified_base
<222> LOCATION: (16)
<223> OTHER INFORMATION: Where n is a, c, g or t
<220> FEATURE:
<221> NAME/KEY: modified_base
<222> LOCATION: (21)
<223> OTHER INFORMATION: Where n is a, c, g or t
<220> FEATURE:
<221> NAME/KEY: modified_base
<222> LOCATION: (24)
<223> OTHER INFORMATION: Where n is a, c, g or t
<220> FEATURE:
<221> NAME/KEY: modified_base
<222> LOCATION: (27)
<223> OTHER INFORMATION: Where n is a, c, g or t
<220> FEATURE:

<221> NAME/KEY: modified_base
<222> LOCATION: (29)
<223> OTHER INFORMATION: Where n is a, c, g or t

<400> SEQUENCE: 69
gagaaggacn tacggncctg ntantanang aatctcc    37

<210> SEQ ID NO 70
<211> LENGTH: 222
<212> TYPE: DNA
<213> ORGANISM: Human
<220> FEATURE:
<221> NAME/KEY: modified_base
<222> LOCATION: (196)
<223> OTHER INFORMATION: Where n is a, c, g or t

<400> SEQUENCE: 70
gtgggtcatt tttgctgtca ccagcaacgt tgccacgacg aacatccttg acagacacat    60
tcttgacatt gaagcccaca ttgtccccag gaagagcttc actcaaagct tcatggcgca   120
tttcgacaga ttttacttcc gttgtaacgt tgactggagc aaaggtgacc accataccgg   180
gtttgagaac acccantcac ctgccccggg cggccgctcg aa                      222

<210> SEQ ID NO 71
<211> LENGTH: 428
<212> TYPE: DNA
<213> ORGANISM: Human
<220> FEATURE:
<221> NAME/KEY: modified_base
<222> LOCATION: (281)
<223> OTHER INFORMATION: Where n is a, c, g or t
<220> FEATURE:
<221> NAME/KEY: modified_base
<222> LOCATION: (308)
<223> OTHER INFORMATION: Where n is a, c, g or t
<220> FEATURE:
<221> NAME/KEY: modified_base
<222> LOCATION: (364)
<223> OTHER INFORMATION: Where n is a, c, g or t
<220> FEATURE:
<221> NAME/KEY: modified_base
<222> LOCATION: (376)
<223> OTHER INFORMATION: Where n is a, c, g or t
<220> FEATURE:
<221> NAME/KEY: modified_base
<222> LOCATION: (383)
<223> OTHER INFORMATION: Where n is a, c, g or t
<220> FEATURE:
<221> NAME/KEY: modified_base
<222> LOCATION: (397)
<223> OTHER INFORMATION: Where n is a, c, g or t
<220> FEATURE:
<221> NAME/KEY: modified_base
<222> LOCATION: (403)
<223> OTHER INFORMATION: Where n is a, c, g or t
<220> FEATURE:
<221> NAME/KEY: modified_base
<222> LOCATION: (420)
<223> OTHER INFORMATION: Where n is a, c, g or t

<400> SEQUENCE: 71
caggagtatt ttgtagaaaa gccagaagag cattagtaga tgtatggaaa tatacggtag    60
ggcacacgct gacagtactt ttcccaagcc acgccgtatt tcttcttaca gtggtactcg   120
tcacgagctt ctcggtggac aagcaacatg gtgaaataaa ttatgtagaa ataaggcaga   180
atgtggttaa aaccacatgg gagggaccac gccaaggcca tgatgagatc acccaagtaa   240
ttggggtggc gaacaaagcc ccaccatcca gaaactagaa naattttcc cgttgaaata    300 tgaatggntt ttaaatgtgc aagctttgga tcactgggaa ttttcccgaa tgccttttc    360

```
tganaattgc accttnggaa gantccttac cccaagnttc agaccattat ttnaaaagcn    420
ttggaact                                                            428
```

<210> SEQ ID NO 72
<211> LENGTH: 264
<212> TYPE: DNA
<213> ORGANISM: Human
<220> FEATURE:
<221> NAME/KEY: modified_base
<222> LOCATION: (218)
<223> OTHER INFORMATION: Where n is a, c, g or t
<220> FEATURE:
<221> NAME/KEY: modified_base
<222> LOCATION: (236)
<223> OTHER INFORMATION: Where n is a, c, g or t
<220> FEATURE:
<221> NAME/KEY: modified_base
<222> LOCATION: (247)
<223> OTHER INFORMATION: Where n is a, c, g or t
<220> FEATURE:
<221> NAME/KEY: modified_base
<222> LOCATION: (256)
<223> OTHER INFORMATION: Where n is a, c, g or t

<400> SEQUENCE: 72

```
gaataaagag cttactggaa tccagcaggg ttttctgccc aaggatttgc aagctgaagc    60
tctctgcaaa cttgatagga gagtaaaaag ccacaataga gcagtttatg aagatcttgg   120
aggagattga cacacttgat cctgccagaa aatttcaaag acagtagatt gaaaaggaaa   180
ggctttggta aaaaaaggtt caggcattcc tagccgantg tgacacagtg gagcanaaca   240
tctgcangag actgancggc tgca                                          264
```

<210> SEQ ID NO 73
<211> LENGTH: 442
<212> TYPE: DNA
<213> ORGANISM: Human
<220> FEATURE:
<221> NAME/KEY: modified_base
<222> LOCATION: (249)
<223> OTHER INFORMATION: Where n is a, c, g or t
<220> FEATURE:
<221> NAME/KEY: modified_base
<222> LOCATION: (283)
<223> OTHER INFORMATION: Where n is a, c, g or t
<220> FEATURE:
<221> NAME/KEY: modified_base
<222> LOCATION: (313)
<223> OTHER INFORMATION: Where n is a, c, g or t
<220> FEATURE:
<221> NAME/KEY: modified_base
<222> LOCATION: (385)
<223> OTHER INFORMATION: Where n is a, c, g or t
<220> FEATURE:
<221> NAME/KEY: modified_base
<222> LOCATION: (390)
<223> OTHER INFORMATION: Where n is a, c, g or t
<220> FEATURE:
<221> NAME/KEY: modified_base
<222> LOCATION: (407)
<223> OTHER INFORMATION: Where n is a, c, g or t

<400> SEQUENCE: 73

```
ggcgaatccg gcgggtatca gagccatcag aaccgccacc atgacggtgg gcaagagcag    60
caagatgctg cagcatattg attacaggat gaggtgcatc ctgcaggacg gccggatctt   120
cattggcacc ttcaaggctt ttgacaagca catgaatttg atcctctgtg actgtgatga   180
gttcagaaag atcaagccaa agaacttcaa acaagcagaa agggaagaga agcgagtcct   240
```

-continued

| | |
|---|---|
| cggtctggng ctgctgccaa gggagaatct ggtctcaatg acngtagaag gaccttcttc | 300 |
| caaagatact ggnattgctc gagttccact tgctggaact tcccgggggcc caaggatcgc | 360 |
| aaggcttctg gcaaaagaaa tccanacttn ggccgggacc acctaancca attcacacac | 420 |
| tggcggccgt actagtggat cc | 442 |

<210> SEQ ID NO 74
<211> LENGTH: 337
<212> TYPE: DNA
<213> ORGANISM: Human
<220> FEATURE:
<221> NAME/KEY: modified_base
<222> LOCATION: (167)
<223> OTHER INFORMATION: Where n is a, c, g or t
<220> FEATURE:
<221> NAME/KEY: modified_base
<222> LOCATION: (268)
<223> OTHER INFORMATION: Where n is a, c, g or t

<400> SEQUENCE: 74

| | |
|---|---|
| ggtagcagcg tctccagagc ctgatctggg gtcccagata cccaggcagc agcagccctg | 60 |
| gaggtaaagg gcaagctccc caatgtgagg ggagacccca ttcctggtca gccaggcttt | 120 |
| cagaggagat agcaggtcga gggagccaac gaagaagaga ctgccancag gggaaggact | 180 |
| gtcccgccaa ggacagaact gattcagggg ggtcaatgct cctctagaga agagccacac | 240 |
| agaactgggg ggtccaggaa ccatgaanct tggctgtggt ctaaggagcc aggaatctgg | 300 |
| acagtgttct gggtcatacc aggattctgg aattgta | 337 |

<210> SEQ ID NO 75
<211> LENGTH: 588
<212> TYPE: DNA
<213> ORGANISM: Human
<220> FEATURE:
<221> NAME/KEY: modified_base
<222> LOCATION: (444)
<223> OTHER INFORMATION: Where n is a, c, g or t
<220> FEATURE:
<221> NAME/KEY: modified_base
<222> LOCATION: (495)
<223> OTHER INFORMATION: Where n is a, c, g or t
<220> FEATURE:
<221> NAME/KEY: modified_base
<222> LOCATION: (531)
<223> OTHER INFORMATION: Where n is a, c, g or t
<220> FEATURE:
<221> NAME/KEY: modified_base
<222> LOCATION: (562)
<223> OTHER INFORMATION: Where n is a, c, g or t

<400> SEQUENCE: 75

| | |
|---|---|
| catgatgagt tctgagctac ggaggaaccc tcatttcctc aaaagtaatt tattttttaca | 60 |
| gcttctggtt tcacatgaaa ttgtttgcgc tactgagact gttactacaa acttttttaag | 120 |
| acatgaaaag gcgtaatgaa aaccatcccg tccccattcc tcctcctctc tgagggactg | 180 |
| gagggaagcc gtgcttctga ggaacaactc taattagtac acttgtgttt gtagatttac | 240 |
| actttgtatt atgtattaac atggcgtgtt tatttttgta tttttctctg gttgggagta | 300 |
| tgatatgaag gatcaagatc ctcaactcac acatgtagac aaacattagc tctttactct | 360 |
| ttctcaaccc cttttatgat tttaataatt ctcacttaac taattttgta agcctgagat | 420 |
| caataagaaa tgttcaggag agangaaaga aaaaaaatat atgttcccca tttatattta | 480 |
| gagagagacc cttantcttg cctgcaaaaa gtccacctttt catagtagta ngggccacat | 540 |
| attacattca gttgctatag gncagcactg aactgcatta cctgggca | 588 |

<210> SEQ ID NO 76
<211> LENGTH: 196
<212> TYPE: DNA
<213> ORGANISM: Human

<400> SEQUENCE: 76

```
gcggtatcac agcctggccc ccatgtacta tcgggggggcc caggctgcca tcgtggtcta      60
tgacatcacc aacacagata catttgcacg ggccaagaac tgggtgaagg agctacagag     120
gcaggccagc cccaacatcg tcattgcact cgcgggtaac aaggcagacc tggacctgcc     180
cgggcggccg ctcgaa                                                     196
```

<210> SEQ ID NO 77
<211> LENGTH: 458
<212> TYPE: DNA
<213> ORGANISM: Human
<220> FEATURE:
<221> NAME/KEY: modified_base
<222> LOCATION: (196)
<223> OTHER INFORMATION: Where n is a, c, g or t
<220> FEATURE:
<221> NAME/KEY: modified_base
<222> LOCATION: (335)
<223> OTHER INFORMATION: Where n is a, c, g or t
<220> FEATURE:
<221> NAME/KEY: modified_base
<222> LOCATION: (409)
<223> OTHER INFORMATION: Where n is a, c, g or t
<220> FEATURE:
<221> NAME/KEY: modified_base
<222> LOCATION: (410)
<223> OTHER INFORMATION: Where n is a, c, g or t
<220> FEATURE:
<221> NAME/KEY: modified_base
<222> LOCATION: (417)
<223> OTHER INFORMATION: Where n is a, c, g or t
<220> FEATURE:
<221> NAME/KEY: modified_base
<222> LOCATION: (442)
<223> OTHER INFORMATION: Where n is a, c, g or t
<220> FEATURE:
<221> NAME/KEY: modified_base
<222> LOCATION: (447)
<223> OTHER INFORMATION: Where n is a, c, g or t
<220> FEATURE:
<221> NAME/KEY: modified_base
<222> LOCATION: (450)
<223> OTHER INFORMATION: Where n is a, c, g or t

<400> SEQUENCE: 77

```
agtagagatg gggtttcact gtgttaacca ggatggtctt gatctcctgg cctcgtgatc      60
tgcccgcctc ggcctcccaa agtgttggga ttacaggcgt gaaccaccgc acccggccag     120
aaatgttagt ttttccctat tctctctcct ttttcctatt atatacttgg tcaaccagac     180
agccatccta ccccanaatg gtaatgcctc ttcattcctc atatgaggga ataaaagaga     240
aaaaagcttt tggaaaacat ccacttatct aatcatccca aatatgtaat caaaagtata     300
caactcatgt gaagaataca ctggtaaaat gttantatag gccaaggtat cttgaattcc     360
tatatagaaa gctggtaaat gccctttttgg ctggaaccgc catcttccnn taattcnccc     420
aaaatgacca aacacaaagg gnaagangan aagccccc                             458
```

<210> SEQ ID NO 78
<211> LENGTH: 464
<212> TYPE: DNA
<213> ORGANISM: Human
<220> FEATURE:

```
<221> NAME/KEY: modified_base
<222> LOCATION: (376)
<223> OTHER INFORMATION: Where n is a, c, g or t
<220> FEATURE:
<221> NAME/KEY: modified_base
<222> LOCATION: (397)
<223> OTHER INFORMATION: Where n is a, c, g or t
<220> FEATURE:
<221> NAME/KEY: modified_base
<222> LOCATION: (442)
<223> OTHER INFORMATION: Where n is a, c, g or t
<220> FEATURE:
<221> NAME/KEY: modified_base
<222> LOCATION: (454)
<223> OTHER INFORMATION: Where n is a, c, g or t

<400> SEQUENCE: 78
tccgcaaatt tcctgccggc aaggtcccag catttgaggg tgatgatgga ttctgtgtgt      60
ttgagagcaa cgccattgcc tactatgtga gcaatgagga gctgcgggga agtactccag     120
aggcagcagc ccaggtggtg cagtgggtga gctttgctga ttccgatata gtgccccag     180 ccagtacctg ggtgttcccc accttgggca tcatgcacca caacaaacag gccactgaga     240
atgcaaagga ggaagtgagg cgaattctgg ggctgctgga tgcttacttg aagacgagga     300
cttttctggt gggcgaacga gtgacattgg ctgacatcac agttgtctgc accctgttgt     360
ggctctataa gcaggntcta gaaccttctt ttcgcangac cttcggccgg accacgctta     420
acccaaattc cacacacttg cnggccgtac taanggaatc ccac                      464

<210> SEQ ID NO 79
<211> LENGTH: 380
<212> TYPE: DNA
<213> ORGANISM: Human
<220> FEATURE:
<221> NAME/KEY: modified_base
<222> LOCATION: (164)
<223> OTHER INFORMATION: Where n is a, c, g or t
<220> FEATURE:
<221> NAME/KEY: modified_base
<222> LOCATION: (188)
<223> OTHER INFORMATION: Where n is a, c, g or t
<220> FEATURE:
<221> NAME/KEY: modified_base
<222> LOCATION: (350)
<223> OTHER INFORMATION: Where n is a, c, g or t

<400> SEQUENCE: 79
ctgtatgacc agtttttcca tctccttcac ttctaccttg atcagctcga agtccagttc      60
agtgtaagaa atggtatcct tctccatgat gtcaattcgg acagttaggt ttaacagttt     120
cttttcatac acactaatta attggacata ttccctcact ttanaaagtt cttttctcaaa    180 cttctganaa aagaacatga actgtgaatt ccaagcgttc ccactctgtc cacgggaaaa     240
ggtggtgtct ggcagggaaa cagaacactg gcaggtccac ggtcatccac ggagccggtg     300
aaattgggaa aacaactggg acacagaacc tccgctgcct aagctgcggn tgggagcttg     360
gaacccgacc tggaactgga                                                 380

<210> SEQ ID NO 80
<211> LENGTH: 360
<212> TYPE: DNA
<213> ORGANISM: Human
<220> FEATURE:
<221> NAME/KEY: modified_base
<222> LOCATION: (42)
<223> OTHER INFORMATION: Where n is a, c, g or t
<220> FEATURE:
<221> NAME/KEY: modified_base
```

<222> LOCATION: (130)
<223> OTHER INFORMATION: Where n is a, c, g or t
<220> FEATURE:
<221> NAME/KEY: modified_base
<222> LOCATION: (131)
<223> OTHER INFORMATION: Where n is a, c, g or t
<220> FEATURE:
<221> NAME/KEY: modified_base
<222> LOCATION: (134)
<223> OTHER INFORMATION: Where n is a, c, g or t
<220> FEATURE:
<221> NAME/KEY: modified_base
<222> LOCATION: (200)
<223> OTHER INFORMATION: Where n is a, c, g or t
<220> FEATURE:
<221> NAME/KEY: modified_base
<222> LOCATION: (210)
<223> OTHER INFORMATION: Where n is a, c, g or t
<220> FEATURE:
<221> NAME/KEY: modified_base
<222> LOCATION: (226)
<223> OTHER INFORMATION: Where n is a, c, g or t
<220> FEATURE:
<221> NAME/KEY: modified_base
<222> LOCATION: (243)
<223> OTHER INFORMATION: Where n is a, c, g or t
<220> FEATURE:
<221> NAME/KEY: modified_base
<222> LOCATION: (257)
<223> OTHER INFORMATION: Where n is a, c, g or t
<220> FEATURE:
<221> NAME/KEY: modified_base
<222> LOCATION: (273)
<223> OTHER INFORMATION: Where n is a, c, g or t
<220> FEATURE:
<221> NAME/KEY: modified_base
<222> LOCATION: (278)
<223> OTHER INFORMATION: Where n is a, c, g or t
<220> FEATURE:
<221> NAME/KEY: modified_base
<222> LOCATION: (295)
<223> OTHER INFORMATION: Where n is a, c, g or t
<220> FEATURE:
<221> NAME/KEY: modified_base
<222> LOCATION: (303)
<223> OTHER INFORMATION: Where n is a, c, g or t
<220> FEATURE:
<221> NAME/KEY: modified_base
<222> LOCATION: (316)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t
<220> FEATURE:
<221> NAME/KEY: modified_base
<222> LOCATION: (344)
<223> OTHER INFORMATION: Where n is a, c, g or t
<220> FEATURE:
<221> NAME/KEY: modified_base
<222> LOCATION: (357)
<223> OTHER INFORMATION: Where n is a, c, g or t
<220> FEATURE:
<221> NAME/KEY: modified_base
<222> LOCATION: (360)
<223> OTHER INFORMATION: Where n is a, c, g or t

<400> SEQUENCE: 80
tcgagcggcc gcccgggcag gtcctcagag agctgtttgt tncgcttctt caaaaactcc    60
tattctccac ttctgctaaa ggactggatg acatcaattg tgatagcaat atttgtgggt   120
gttctgtcan ncancatcgc actcctgaac aaagtagatg ttggattgga tcagtctctt   180
tccacccaga tgactcctan atggtggatn atttcaaatc catcantcag tacctgcatg   240
cgnggtccgc ctgtgtnctt tgtcctgcag ganggqcnct actacacttc ttccnagggg   300
canaacatgg tgtgcngcgg ccatgggctg gcaacantga ttcnctgctg cacccanatn    360

```
<210> SEQ ID NO 81
<211> LENGTH: 440
<212> TYPE: DNA
<213> ORGANISM: Human
<220> FEATURE:
<221> NAME/KEY: modified_base
<222> LOCATION: (121)
<223> OTHER INFORMATION: Where n is a, c, g or t
<220> FEATURE:
<221> NAME/KEY: modified_base
<222> LOCATION: (132)
<223> OTHER INFORMATION: Where n is a, c, g or t
<220> FEATURE:
<221> NAME/KEY: modified_base
<222> LOCATION: (191)
<223> OTHER INFORMATION: Where n is a, c, g or t
<220> FEATURE:
<221> NAME/KEY: modified_base
<222> LOCATION: (211)
<223> OTHER INFORMATION: Where n is a, c, g or t
<220> FEATURE:
<221> NAME/KEY: modified_base
<222> LOCATION: (224)
<223> OTHER INFORMATION: Where n is a, c, g or t
<220> FEATURE:
<221> NAME/KEY: modified_base
<222> LOCATION: (312)
<223> OTHER INFORMATION: Where n is a, c, g or t
<220> FEATURE:
<221> NAME/KEY: modified_base
<222> LOCATION: (342)
<223> OTHER INFORMATION: Where n is a, c, g or t
<220> FEATURE:
<221> NAME/KEY: modified_base
<222> LOCATION: (354)
<223> OTHER INFORMATION: Where n is a, c, g or t
<220> FEATURE:
<221> NAME/KEY: modified_base
<222> LOCATION: (360)
<223> OTHER INFORMATION: Where n is a, c, g or t
<220> FEATURE:
<221> NAME/KEY: modified_base
<222> LOCATION: (407)
<223> OTHER INFORMATION: Where n is a, c, g or t
<220> FEATURE:
<221> NAME/KEY: modified_base
<222> LOCATION: (412)
<223> OTHER INFORMATION: Where n is a, c, g or t
<220> FEATURE:
<221> NAME/KEY: modified_base
<222> LOCATION: (427)
<223> OTHER INFORMATION: Where n is a, c, g or t

<400> SEQUENCE: 81
```
acgtggtccg gcgagtctga cctgcagata tgaactcctt gggaaaccta cattctgcct     60
cagacatact gggggcaaat ggctttaaaa gtctggctca gggagccaag attacagaaa    120
nccgttgagt cnccatacat ggacactgac aaaggaactg aagatatcca acaagccct    180 cctggtcccg ngcctgcata agatcggga ncggaacggt accngacgtc tgtggtcagg    240
ggttgtggaa aattggaaaa aaccagtcct gcccacattg acagggaagc ctcaacggaa    300
attgaacaga tngtcttatc accagtctcc cctcctggat cntgtctcgg ctcnggggan    360
tcagtgatca gtcctttcag gtggaagaag caaagaagat caacaanaag cngatcctct    420
cacctgntac cagcatatgg                                                440

```
<210> SEQ ID NO 82
<211> LENGTH: 264
<212> TYPE: DNA
<213> ORGANISM: Human
```

```
<220> FEATURE:
<221> NAME/KEY: modified_base
<222> LOCATION: (18)
<223> OTHER INFORMATION: Where n is a, c, g or t
<220> FEATURE:
<221> NAME/KEY: modified_base
<222> LOCATION: (54)
<223> OTHER INFORMATION: Where n is a, c, g or t
<220> FEATURE:
<221> NAME/KEY: modified_base
<222> LOCATION: (130)
<223> OTHER INFORMATION: Where n is a, c, g or t
<220> FEATURE:
<221> NAME/KEY: modified_base
<222> LOCATION: (137)
<223> OTHER INFORMATION: Where n is a, c, g or t
<220> FEATURE:
<221> NAME/KEY: modified_base
<222> LOCATION: (162)
<223> OTHER INFORMATION: Where n is a, c, g or t
<220> FEATURE:
<221> NAME/KEY: modified_base
<222> LOCATION: (175)
<223> OTHER INFORMATION: Where n is a, c, g or t
<220> FEATURE:
<221> NAME/KEY: modified_base
<222> LOCATION: (184)
<223> OTHER INFORMATION: Where n is a, c, g or t
<220> FEATURE:
<221> NAME/KEY: modified_base
<222> LOCATION: (190)
<223> OTHER INFORMATION: Where n is a, c, g or t
<220> FEATURE:
<221> NAME/KEY: modified_base
<222> LOCATION: (192)
<223> OTHER INFORMATION: Where n is a, c, g or t
<220> FEATURE:
<221> NAME/KEY: modified_base
<222> LOCATION: (202)
<223> OTHER INFORMATION: Where n is a, c, g or t
<220> FEATURE:
<221> NAME/KEY: modified_base
<222> LOCATION: (206)
<223> OTHER INFORMATION: Where n is a, c, g or t
<220> FEATURE:
<221> NAME/KEY: modified_base
<222> LOCATION: (213)
<223> OTHER INFORMATION: Where n is a, c, g or t
<220> FEATURE:
<221> NAME/KEY: modified_base
<222> LOCATION: (218)
<223> OTHER INFORMATION: Where n is a, c, g or t
<220> FEATURE:
<221> NAME/KEY: modified_base
<222> LOCATION: (241)
<223> OTHER INFORMATION: Where n is a, c, g or t
<220> FEATURE:
<221> NAME/KEY: modified_base
<222> LOCATION: (260)
<223> OTHER INFORMATION: Where n is a, c, g or t

<400> SEQUENCE: 82
agcgtggtcg cggccgangt cctgacattc ctgccttctt atattaatta tacnaataaa      60
acaaaatagt gttgaagtgt tggagcggcg aaaattttg ggggtggta tggacagaga      120 atgggcgatn ttctcanggc tgcttcaagt gggattgggg cngcgtggga tcatncagtg      180
gganagattn cnctgaccgg antctnttgg tanggatnat cttgtgggga tgtgcaagag      240
ncattcgtct cctgaatgan tggt                                             264

<210> SEQ ID NO 83
<211> LENGTH: 410
<212> TYPE: DNA
<213> ORGANISM: Human
<220> FEATURE:
```

```
<221> NAME/KEY: modified_base
<222> LOCATION: (2)
<223> OTHER INFORMATION: Where n is a, c, g or t
<220> FEATURE:
<221> NAME/KEY: modified_base
<222> LOCATION: (18)
<223> OTHER INFORMATION: Where n is a, c, g or t
<220> FEATURE:
<221> NAME/KEY: modified_base
<222> LOCATION: (169)
<223> OTHER INFORMATION: Where n is a, c, g or t
<220> FEATURE:
<221> NAME/KEY: modified_base
<222> LOCATION: (209)
<223> OTHER INFORMATION: Where n is a, c, g or t
<220> FEATURE:
<221> NAME/KEY: modified_base
<222> LOCATION: (245)
<223> OTHER INFORMATION: Where n is a, c, g or t
<220> FEATURE:
<221> NAME/KEY: modified_base
<222> LOCATION: (263)
<223> OTHER INFORMATION: Where n is a, c, g or t
<220> FEATURE:
<221> NAME/KEY: modified_base
<222> LOCATION: (265)
<223> OTHER INFORMATION: Where n is a, c, g or t
<220> FEATURE:
<221> NAME/KEY: modified_base
<222> LOCATION: (284)
<223> OTHER INFORMATION: Where n is a, c, g or t
<220> FEATURE:
<221> NAME/KEY: modified_base
<222> LOCATION: (378)
<223> OTHER INFORMATION: Where n is a, c, g or t

<400> SEQUENCE: 83
ancgtggtcg cggccgangt ccacagttgt gggagagcca gccattgtgg gggcagctcc     60
acaggtaaga ctcgtgtcct gagcagcgca catcatccag acaatgggt cctgagccct    120
gaccaaaccg ggcatttcct ggggctgaca tggcccagcc acagcccant tgcctgcaga   180
cgaaattggc atcattggtg tcccagtant catcacacac ggtgcccccag gaacctccgg   240
tatangaact ccactcggcc tcnanacctg tcgcctccat tccncagcct caggggggcaa   300
actgggattc agatccttct gtgggtacag gtggtgatat cctgacaggc caactttctg   360
gcctgagtgt tgactgangc tgggcagacc tgcccgggcg ccgctcgaa              410

<210> SEQ ID NO 84
<211> LENGTH: 320
<212> TYPE: DNA
<213> ORGANISM: Human
<220> FEATURE:
<221> NAME/KEY: modified_base
<222> LOCATION: (61)
<223> OTHER INFORMATION: Where n is a, c, g or t
<220> FEATURE:
<221> NAME/KEY: modified_base
<222> LOCATION: (81)
<223> OTHER INFORMATION: Where n is a, c, g or t
<220> FEATURE:
<221> NAME/KEY: modified_base
<222> LOCATION: (82)
<223> OTHER INFORMATION: Where n is a, c, g or t
<220> FEATURE:
<221> NAME/KEY: modified_base
<222> LOCATION: (90)
<223> OTHER INFORMATION: Where n is a, c, g or t
<220> FEATURE:
<221> NAME/KEY: modified_base
<222> LOCATION: (98)
<223> OTHER INFORMATION: Where n is a, c, g or t
<220> FEATURE:
<221> NAME/KEY: modified_base
```

```
<222> LOCATION: (111)
<223> OTHER INFORMATION: Where n is a, c, g or t
<220> FEATURE:
<221> NAME/KEY: modified_base
<222> LOCATION: (153)
<223> OTHER INFORMATION: Where n is a, c, g or t
<220> FEATURE:
<221> NAME/KEY: modified_base
<222> LOCATION: (182)
<223> OTHER INFORMATION: Where n is a, c, g or t
<220> FEATURE:
<221> NAME/KEY: modified_base
<222> LOCATION: (184)
<223> OTHER INFORMATION: Where n is a, c, g or t
<220> FEATURE:
<221> NAME/KEY: modified_base
<222> LOCATION: (187)
<223> OTHER INFORMATION: Where n is a, c, g or t
<220> FEATURE:
<221> NAME/KEY: modified_base
<222> LOCATION: (189)
<223> OTHER INFORMATION: Where n is a, c, g or t
<220> FEATURE:
<221> NAME/KEY: modified_base
<222> LOCATION: (198)
<223> OTHER INFORMATION: Where n is a, c, g or t
<220> FEATURE:
<221> NAME/KEY: modified_base
<222> LOCATION: (210)
<223> OTHER INFORMATION: Where n is a, c, g or t
<220> FEATURE:
<221> NAME/KEY: modified_base
<222> LOCATION: (211)
<223> OTHER INFORMATION: Where n is a, c, g or t
<220> FEATURE:
<221> NAME/KEY: modified_base
<222> LOCATION: (212)
<223> OTHER INFORMATION: Where n is a, c, g or t
<220> FEATURE:
<221> NAME/KEY: modified_base
<222> LOCATION: (238)
<223> OTHER INFORMATION: Where n is a, c, g or t
<220> FEATURE:
<221> NAME/KEY: modified_base
<222> LOCATION: (262)
<223> OTHER INFORMATION: Where n is a, c, g or t
<220> FEATURE:
<221> NAME/KEY: modified_base
<222> LOCATION: (277)
<223> OTHER INFORMATION: Where n is a, c, g or t
<220> FEATURE:
<221> NAME/KEY: modified_base
<222> LOCATION: (279)
<223> OTHER INFORMATION: Where n is a, c, g or t
<220> FEATURE:
<221> NAME/KEY: modified_base
<222> LOCATION: (289)
<223> OTHER INFORMATION: Where n is a, c, g or t
<220> FEATURE:
<221> NAME/KEY: modified_base
<222> LOCATION: (295)
<223> OTHER INFORMATION: Where n is a, c, g or t
<220> FEATURE:
<221> NAME/KEY: modified_base
<222> LOCATION: (299)
<223> OTHER INFORMATION: Where n is a, c, g or t
<220> FEATURE:
<221> NAME/KEY: modified_base
<222> LOCATION: (318)
<223> OTHER INFORMATION: Where n is a, c, g or t
<220> FEATURE:
<221> NAME/KEY: modified_base
<222> LOCATION: (320)
<223> OTHER INFORMATION: Where n is a, c, g or t

<400> SEQUENCE: 84
tcgaacggcc gcccgggcag gtctgcccca ggtgtatcca tttgccgccg atctctatca     60
```

```
naaggagctg gctaccctgc nncgacgaan tcctgaanat aatctcaccc ncccagatct    120
ctctgtcgca atggagatgt cgtcatcggt ggncctgatc acagggcatt ggactcagag    180
anangtnanc acagtgtnga agcgattgan nnagttcagt tgctggtctt acccgatntt    240
ggaaggaagg aaaacgtgtt angacgtatc tcgatgnant tgaccaaanc tgaangctnc    300 aggggcatc gcaaaganan                                                 320
```

<210> SEQ ID NO 85
<211> LENGTH: 218
<212> TYPE: DNA
<213> ORGANISM: Human
<220> FEATURE:
<221> NAME/KEY: modified_base
<222> LOCATION: (117)
<223> OTHER INFORMATION: Where n is a, c, g or t
<220> FEATURE:
<221> NAME/KEY: modified_base
<222> LOCATION: (120)
<223> OTHER INFORMATION: Where n is a, c, g or t
<220> FEATURE:
<221> NAME/KEY: modified_base
<222> LOCATION: (152)
<223> OTHER INFORMATION: Where n is a, c, g or t
<220> FEATURE:
<221> NAME/KEY: modified_base
<222> LOCATION: (155)
<223> OTHER INFORMATION: Where n is a, c, g or t
<220> FEATURE:
<221> NAME/KEY: modified_base
<222> LOCATION: (193)
<223> OTHER INFORMATION: Where n is a, c, g or t
<220> FEATURE:
<221> NAME/KEY: modified_base
<222> LOCATION: (194)
<223> OTHER INFORMATION: Where n is a, c, g or t

<400> SEQUENCE: 85

```
tcgagcggcc gcccgggcag gtctgctgcc cgtgctggtg ccattgcccc atgtgaagtc    60
actgtgccag cccagaacac tggtctcggg cccgagaaga ctcctttctc caggctntan    120
gtatcaccac taaaatctcc aggggcacca tnganatcct gggtgtccgc aatgttgcca    180
atgtctgtcc gcnnattggc tacccaactg ttgcatca                            218
```

<210> SEQ ID NO 86
<211> LENGTH: 283
<212> TYPE: DNA
<213> ORGANISM: Human
<220> FEATURE:
<221> NAME/KEY: modified_base
<222> LOCATION: (25)
<223> OTHER INFORMATION: Where n is a, c, g or t
<220> FEATURE:
<221> NAME/KEY: modified_base
<222> LOCATION: (183)
<223> OTHER INFORMATION: Where n is a, c, g or t
<220> FEATURE:
<221> NAME/KEY: modified_base
<222> LOCATION: (193)
<223> OTHER INFORMATION: Where n is a, c, g or t
<220> FEATURE:
<221> NAME/KEY: modified_base
<222> LOCATION: (204)
<223> OTHER INFORMATION: Where n is a, c, g or t
<220> FEATURE:
<221> NAME/KEY: modified_base
<222> LOCATION: (225)
<223> OTHER INFORMATION: Where n is a, c, g or t
<220> FEATURE:
<221> NAME/KEY: modified_base
<222> LOCATION: (240)
<223> OTHER INFORMATION: Where n is a, c, g or t

<400> SEQUENCE: 86

```
tcgacttctt gtgaaggttt tgganaaata tgtatcagtt cgttttattt gggtattcaa      60
taatatcctt ggtgataatg ctgactccat ggcttctgac cccaaaaatt gaccctgctg     120
ccactggttg tagccctgag attgattttt gtagccacga ttgtttcctc gtcctctgaa     180
gtnctggttg tanttccctc tgtngggcat tcccctctgt tgtanttccc tctgtttgan     240
taactaccac ggccaggaaa aacaggggca cgaaggtatg gat                       283
```

<210> SEQ ID NO 87
<211> LENGTH: 179
<212> TYPE: DNA
<213> ORGANISM: Human
<220> FEATURE:
<221> NAME/KEY: modified_base
<222> LOCATION: (66)
<223> OTHER INFORMATION: Where n is a, c, g or t
<220> FEATURE:
<221> NAME/KEY: modified_base
<222> LOCATION: (81)
<223> OTHER INFORMATION: Where n is a, c, g or t
<220> FEATURE:
<221> NAME/KEY: modified_base
<222> LOCATION: (89)
<223> OTHER INFORMATION: Where n is a, c, g or t
<220> FEATURE:
<221> NAME/KEY: modified_base
<222> LOCATION: (113)
<223> OTHER INFORMATION: Where n is a, c, g or t
<220> FEATURE:
<221> NAME/KEY: modified_base
<222> LOCATION: (120)
<223> OTHER INFORMATION: Where n is a, c, g or t
<220> FEATURE:
<221> NAME/KEY: modified_base
<222> LOCATION: (135)
<223> OTHER INFORMATION: Where n is a, c, g or t
<220> FEATURE:
<221> NAME/KEY: modified_base
<222> LOCATION: (148)
<223> OTHER INFORMATION: Where n is a, c, g or t
<220> FEATURE:
<221> NAME/KEY: modified_base
<222> LOCATION: (161)
<223> OTHER INFORMATION: Where n is a, c, g or t

<400> SEQUENCE: 87

```
agcgtggtcc cggccgatgt ctttctgtgt aagtgcataa cactccacat acttgacatc      60
cttcangtca cgggccagct nttcagcant ctctggagtg ataggctact gtntgttctn     120
ggcaagtgtc tcaanaatac agggtcntc tctgagatga ntttcagtcc cgaaccctc      179
```

<210> SEQ ID NO 88
<211> LENGTH: 512
<212> TYPE: DNA
<213> ORGANISM: Human
<220> FEATURE:
<221> NAME/KEY: modified_base
<222> LOCATION: (27)
<223> OTHER INFORMATION: Where n is a, c, g or t
<220> FEATURE:
<221> NAME/KEY: modified_base
<222> LOCATION: (30)
<223> OTHER INFORMATION: Where n is a, c, g or t
<220> FEATURE:
<221> NAME/KEY: modified_base
<222> LOCATION: (75)
<223> OTHER INFORMATION: Where n is a, c, g or t
<220> FEATURE:
<221> NAME/KEY: modified_base
<222> LOCATION: (106)

```
<223> OTHER INFORMATION: Where n is a, c, g or t
<220> FEATURE:
<221> NAME/KEY: modified_base
<222> LOCATION: (198)
<223> OTHER INFORMATION: Where n is a, c, g or t
<220> FEATURE:
<221> NAME/KEY: modified_base
<222> LOCATION: (216)
<223> OTHER INFORMATION: Where n is a, c, g or t
<220> FEATURE:
<221> NAME/KEY: modified_base
<222> LOCATION: (294)
<223> OTHER INFORMATION: Where n is a, c, g or t
<220> FEATURE:
<221> NAME/KEY: modified_base
<222> LOCATION: (349)
<223> OTHER INFORMATION: Where n is a, c, g or t

<400> SEQUENCE: 88
tcgagcggcc gcccgggcag gtcctancan agaatcacca aatttatgga gagttaacag      60
gggtttaaca ggaangaagt gcctttagta agttctcaag ccagangctg gaggcagcag    120
ctaaatcaga ggacaggatc ctcagtgaaa gtgagccatt cggggtggca tgtcactcca    180
ggaataagca caacttanaa acaaatgatt tcgtangata gcacagtgac attggtgcac    240
ttgtgaacct gaggccactg tgtcaaactg tgcactggtt gtgaataggg aganccaaaa    300
attatgtcct actgggtaat gagctttcaa tgggctcgat cctctcacnc tgaaagctct    360
gtagagcagc tcagaaccac aaccactccc aacattgacc cttctggggg tactgtctgt    420
ggcacccaca ggaaggagct ggagatcccc attaggactg tccacccaca cttgaagcca    480
caaaactgca cctcggccgc gaccaccgct ta                                  512

<210> SEQ ID NO 89
<211> LENGTH: 358
<212> TYPE: DNA
<213> ORGANISM: Human
<220> FEATURE:
<221> NAME/KEY: modified_base
<222> LOCATION: (65)
<223> OTHER INFORMATION: Where n is a, c, g or t
<220> FEATURE:
<221> NAME/KEY: modified_base
<222> LOCATION: (207)
<223> OTHER INFORMATION: Where n is a, c, g or t
<220> FEATURE:
<221> NAME/KEY: modified_base
<222> LOCATION: (214)
<223> OTHER INFORMATION: Where n is a, c, g or t
<220> FEATURE:
<221> NAME/KEY: modified_base
<222> LOCATION: (221)
<223> OTHER INFORMATION: Where n is a, c, g or t
<220> FEATURE:
<221> NAME/KEY: modified_base
<222> LOCATION: (257)
<223> OTHER INFORMATION: Where n is a, c, g or t
<220> FEATURE:
<221> NAME/KEY: modified_base
<222> LOCATION: (258)
<223> OTHER INFORMATION: Where n is a, c, g or t
<220> FEATURE:
<221> NAME/KEY: modified_base
<222> LOCATION: (266)
<223> OTHER INFORMATION: Where n is a, c, g or t
<220> FEATURE:
<221> NAME/KEY: modified_base
<222> LOCATION: (271)
<223> OTHER INFORMATION: Where n is a, c, g or t
<220> FEATURE:
<221> NAME/KEY: modified_base
<222> LOCATION: (287)
<223> OTHER INFORMATION: Where n is a, c, g or t
```

<220> FEATURE:
<221> NAME/KEY: modified_base
<222> LOCATION: (297)
<223> OTHER INFORMATION: Where n is a, c, g or t
<220> FEATURE:
<221> NAME/KEY: modified_base
<222> LOCATION: (307)
<223> OTHER INFORMATION: Where n is a, c, g or t
<220> FEATURE:
<221> NAME/KEY: modified_base
<222> LOCATION: (308)
<223> OTHER INFORMATION: Where n is a, c, g or t
<220> FEATURE:
<221> NAME/KEY: modified_base
<222> LOCATION: (325)
<223> OTHER INFORMATION: Where n is a, c, g or t

<400> SEQUENCE: 89

```
tcgagcgggc cgcccgggca ggtctgccag tccccatccc agacattctt tgcatctaag      60
ctgangtctg aactgagtgg ggtgggctgg tgtttccatc ctcacaactc cagtgagccg     120
ggtgtggccg tggcctgcgt ctctctggcg gttagtgatg ttggcatcat ccacctttt     180 caaaacaaaa gcactggact gaagaanaat cccnccctgt ntccacccag tccatggttt     240
ttaataaaag ggttatnnaa gttgancaag ncatcaccac acacaancct aagaacnttt     300
ttcatcnntc cccaaaacaa acccncaccc tgggaactcc gggcgcgaac cacgccta      358
```

<210> SEQ ID NO 90
<211> LENGTH: 250
<212> TYPE: DNA
<213> ORGANISM: Human
<220> FEATURE:
<221> NAME/KEY: modified_base
<222> LOCATION: (125)
<223> OTHER INFORMATION: Where n is a, c, g or t
<220> FEATURE:
<221> NAME/KEY: modified_base
<222> LOCATION: (163)
<223> OTHER INFORMATION: Where n is a, c, g or t
<220> FEATURE:
<221> NAME/KEY: modified_base
<222> LOCATION: (172)
<223> OTHER INFORMATION: Where n is a, c, g or t
<220> FEATURE:
<221> NAME/KEY: modified_base
<222> LOCATION: (199)
<223> OTHER INFORMATION: Where n is a, c, g or t
<220> FEATURE:
<221> NAME/KEY: modified_base
<222> LOCATION: (244)
<223> OTHER INFORMATION: Where n is a, c, g or t

<400> SEQUENCE: 90

```
cgagcggccg cccgggcagg tctggatggg gagacggact ggaactgcgg cttcccgtgg      60
cctgcacgca caaggctccc cacggccgcc gaccttcttc agattcgatc gtatgtgtac     120
gcacnaagag ccaaatattg acattcacaa cttcgtggga atnttacccc anaagactgc     180 gacccccga tcaggcgana gcctgagcat agaagaacac cgctgtgggc ttggcactgt     240 gggncccatc                                                          250
```

<210> SEQ ID NO 91
<211> LENGTH: 133
<212> TYPE: DNA
<213> ORGANISM: Human
<220> FEATURE:
<221> NAME/KEY: modified_base
<222> LOCATION: (12)
<223> OTHER INFORMATION: Where n is a, c, g or t
<220> FEATURE:

```
<221> NAME/KEY: modified_base
<222> LOCATION: (56)
<223> OTHER INFORMATION: Where n is a, c, g or t
<220> FEATURE:
<221> NAME/KEY: modified_base
<222> LOCATION: (58)
<223> OTHER INFORMATION: Where n is a, c, g or t
<220> FEATURE:
<221> NAME/KEY: modified_base
<222> LOCATION: (61)
<223> OTHER INFORMATION: Where n is a, c, g or t
<220> FEATURE:
<221> NAME/KEY: modified_base
<222> LOCATION: (78)
<223> OTHER INFORMATION: Where n is a, c, g or t
<220> FEATURE:
<221> NAME/KEY: modified_base
<222> LOCATION: (82)
<223> OTHER INFORMATION: Where n is a, c, g or t
<220> FEATURE:
<221> NAME/KEY: modified_base
<222> LOCATION: (107)
<223> OTHER INFORMATION: Where n is a, c, g or t
<220> FEATURE:
<221> NAME/KEY: modified_base
<222> LOCATION: (116)
<223> OTHER INFORMATION: Where n is a, c, g or t
<220> FEATURE:
<221> NAME/KEY: modified_base
<222> LOCATION: (123)
<223> OTHER INFORMATION: Where n is a, c, g or t
<220> FEATURE:
<221> NAME/KEY: modified_base
<222> LOCATION: (126)
<223> OTHER INFORMATION: Where n is a, c, g or t

<400> SEQUENCE: 91
tcgagcggcc gnccgggcag gtcccgggtg gttgtttgcc gaaatgggca agttcntnaa      60
ncctgggaag gtggtgcntg tnctggctgg acgctactcc ggacgcnaag ctgtcntcgt     120
gangancatt gat                                                       133

<210> SEQ ID NO 92
<211> LENGTH: 232
<212> TYPE: DNA
<213> ORGANISM: Human
<220> FEATURE:
<221> NAME/KEY: modified_base
<222> LOCATION: (18)
<223> OTHER INFORMATION: Where n is a, c, g or t
<220> FEATURE:
<221> NAME/KEY: modified_base
<222> LOCATION: (168)
<223> OTHER INFORMATION: Where n is a, c, g or t
<220> FEATURE:
<221> NAME/KEY: modified_base
<222> LOCATION: (173)
<223> OTHER INFORMATION: Where n is a, c, g or t
<220> FEATURE:
<221> NAME/KEY: modified_base
<222> LOCATION: (179)
<223> OTHER INFORMATION: Where n is a, c, g or t
<220> FEATURE:
<221> NAME/KEY: modified_base
<222> LOCATION: (219)
<223> OTHER INFORMATION: Where n is a, c, g or t

<400> SEQUENCE: 92
agcgtggtcg cggccgangt ctgtcacttt gcggggtag cggtcaattc cagccaccag       60
agcatggctg tagggcgat ctgaggtgcc atcatcaatg ttcttcacga tgacaagctt     120
tgcgtccgga gtagcgtcca gccaggacaa gcaccacctt cccacgtntt cangaactng   180
cccatttcgg cataaccacc cgggacctgc ccgggcggnc gctcgaaaag cc            232
```

<210> SEQ ID NO 93
<211> LENGTH: 480
<212> TYPE: DNA
<213> ORGANISM: Human
<220> FEATURE:
<221> NAME/KEY: modified_base
<222> LOCATION: (19)
<223> OTHER INFORMATION: Where n is a, c, g or t
<220> FEATURE:
<221> NAME/KEY: modified_base
<222> LOCATION: (27)
<223> OTHER INFORMATION: Where n is a, c, g or t
<220> FEATURE:
<221> NAME/KEY: modified_base
<222> LOCATION: (221)
<223> OTHER INFORMATION: Where n is a, c, g or t
<220> FEATURE:
<221> NAME/KEY: modified_base
<222> LOCATION: (406)
<223> OTHER INFORMATION: Where n is a, c, g or t
<220> FEATURE:
<221> NAME/KEY: modified_base
<222> LOCATION: (439)
<223> OTHER INFORMATION: Where n is a, c, g or t

<400> SEQUENCE: 93

```
agcgtgggtc gcggccgang tctgtangct caccggccag agaagaccac tgtgagcatt      60
ttgccgtata tcctgccctg ccatttgttc acttttttaaa ctaaaatagg aacatccgac    120
acacaccgtt tgcatcgtct tctcccttga tattttaagc attttcccat gtcgtgagtt    180
tctcagaaac atgtttttaa caattgtact atttagtcat ngtccattta ctataattta    240
tctgaccatt tccctactgt taaaatactt aagacggttt ctgatttttc cactatttaa    300
ataatgctgt gatgaatatc tttaaaatct tctgatttct tacttttttc cccttagat    360
gcctggaagt ggtattttga ggtgaaagag tttgttcatt ttgaanatat ttctgtctct    420
ctctcgacct gatgtgtana cgctcacttc cagttagcag aaccacctta gtttgtgtct    480
```

<210> SEQ ID NO 94
<211> LENGTH: 472
<212> TYPE: DNA
<213> ORGANISM: Human
<220> FEATURE:
<221> NAME/KEY: modified_base
<222> LOCATION: (9)
<223> OTHER INFORMATION: Where n is a, c, g or t
<220> FEATURE:
<221> NAME/KEY: modified_base
<222> LOCATION: (33)
<223> OTHER INFORMATION: Where n is a, c, g or t
<220> FEATURE:
<221> NAME/KEY: modified_base
<222> LOCATION: (70)
<223> OTHER INFORMATION: Where n is a, c, g or t
<220> FEATURE:
<221> NAME/KEY: modified_base
<222> LOCATION: (105)
<223> OTHER INFORMATION: Where n is a, c, g or t
<220> FEATURE:
<221> NAME/KEY: modified_base
<222> LOCATION: (129)
<223> OTHER INFORMATION: Where n is a, c, g or t
<220> FEATURE:
<221> NAME/KEY: modified_base
<222> LOCATION: (135)
<223> OTHER INFORMATION: Where n is a, c, g or t
<220> FEATURE:
<221> NAME/KEY: modified_base
<222> LOCATION: (136)
<223> OTHER INFORMATION: Where n is a, c, g or t
<220> FEATURE:

```
<221> NAME/KEY: modified_base
<222> LOCATION: (154)
<223> OTHER INFORMATION: Where n is a, c, g or t
<220> FEATURE:
<221> NAME/KEY: modified_base
<222> LOCATION: (180)
<223> OTHER INFORMATION: Where n is a, c, g or t
<220> FEATURE:
<221> NAME/KEY: modified_base
<222> LOCATION: (190)
<223> OTHER INFORMATION: Where n is a, c, g or t
<220> FEATURE:
<221> NAME/KEY: modified_base
<222> LOCATION: (213)
<223> OTHER INFORMATION: Where n is a, c, g or t
<220> FEATURE:
<221> NAME/KEY: modified_base
<222> LOCATION: (232)
<223> OTHER INFORMATION: Where n is a, c, g or t
<220> FEATURE:
<221> NAME/KEY: modified_base
<222> LOCATION: (235)
<223> OTHER INFORMATION: Where n is a, c, g or t
<220> FEATURE:
<221> NAME/KEY: modified_base
<222> LOCATION: (286)
<223> OTHER INFORMATION: Where n is a, c, g or t
<220> FEATURE:
<221> NAME/KEY: modified_base
<222> LOCATION: (292)
<223> OTHER INFORMATION: Where n is a, c, g or t
<220> FEATURE:
<221> NAME/KEY: modified_base
<222> LOCATION: (293)
<223> OTHER INFORMATION: Where n is a, c, g or t
<220> FEATURE:
<221> NAME/KEY: modified_base
<222> LOCATION: (305)
<223> OTHER INFORMATION: Where n is a, c, g or t
<220> FEATURE:
<221> NAME/KEY: modified_base
<222> LOCATION: (335)
<223> OTHER INFORMATION: Where n is a, c, g or t
<220> FEATURE:
<221> NAME/KEY: modified_base
<222> LOCATION: (341)
<223> OTHER INFORMATION: Where n is a, c, g or t
<220> FEATURE:
<221> NAME/KEY: modified_base
<222> LOCATION: (363)
<223> OTHER INFORMATION: Where n is a, c, g or t
<220> FEATURE:
<221> NAME/KEY: modified_base
<222> LOCATION: (372)
<223> OTHER INFORMATION: Where n is a, c, g or t
<220> FEATURE:
<221> NAME/KEY: modified_base
<222> LOCATION: (400)
<223> OTHER INFORMATION: Where n is a, c, g or t
<220> FEATURE:
<221> NAME/KEY: modified_base
<222> LOCATION: (418)
<223> OTHER INFORMATION: Where n is a, c, g or t
<220> FEATURE:
<221> NAME/KEY: modified_base
<222> LOCATION: (422)
<223> OTHER INFORMATION: Where n is a, c, g or t
<220> FEATURE:
<221> NAME/KEY: modified_base
<222> LOCATION: (425)
<223> OTHER INFORMATION: Where n is a, c, g or t
<220> FEATURE:
<221> NAME/KEY: modified_base
<222> LOCATION: (472)
<223> OTHER INFORMATION: Where n is a, c, g or t

<400> SEQUENCE: 94
tcgagcggnc gcccgggcag ggtctgatgt cantcacaac ttgaagggat gccaatgatg    60
```

```
taccaatccn atgtgaaatc tctcctctta tctcctatgc tgganaaggg attacaaagt    120
tatgtggcng ataannaatt ccatgcacct ctantcatcg atgagaatgg agttcatgan    180
ctggtgaacn atggtatctg aacccgatac cangttttgt ttgccacgat angantagct    240
tttatttttg atagaccaac tgtgaaccta ccacacgtct tggacnactg anntctaact    300
atccncaggg ttttattttg cttgttgaac tcttncagct nttgcaaact tcccaagatc    360
canatgactg antttcagat agcattttta tgattcccan ctcattgaag gtcttatnta    420 tntcntttt tccaagccaa ggagaccatt ggacctcggc cgcgaccacc tn             472
```

<210> SEQ ID NO 95
<211> LENGTH: 309
<212> TYPE: DNA
<213> ORGANISM: Human
<220> FEATURE:
<221> NAME/KEY: modified_base
<222> LOCATION: (97)
<223> OTHER INFORMATION: Where n is a, c, g or t
<220> FEATURE:
<221> NAME/KEY: modified_base
<222> LOCATION: (117)
<223> OTHER INFORMATION: Where n is a, c, g or t
<220> FEATURE:
<221> NAME/KEY: modified_base
<222> LOCATION: (139)
<223> OTHER INFORMATION: Where n is a, c, g or t
<220> FEATURE:
<221> NAME/KEY: modified_base
<222> LOCATION: (173)
<223> OTHER INFORMATION: Where n is a, c, g or t
<220> FEATURE:
<221> NAME/KEY: modified_base
<222> LOCATION: (184)
<223> OTHER INFORMATION: Where n is a, c, g or t
<220> FEATURE:
<221> NAME/KEY: modified_base
<222> LOCATION: (193)
<223> OTHER INFORMATION: Where n is a, c, g or t
<220> FEATURE:
<221> NAME/KEY: modified_base
<222> LOCATION: (206)
<223> OTHER INFORMATION: Where n is a, c, g or t
<220> FEATURE:
<221> NAME/KEY: modified_base
<222> LOCATION: (230)
<223> OTHER INFORMATION: Where n is a, c, g or t
<220> FEATURE:
<221> NAME/KEY: modified_base
<222> LOCATION: (236)
<223> OTHER INFORMATION: Where n is a, c, g or t
<220> FEATURE:
<221> NAME/KEY: modified_base
<222> LOCATION: (239)
<223> OTHER INFORMATION: Where n is a, c, g or t
<220> FEATURE:
<221> NAME/KEY: modified_base
<222> LOCATION: (242)
<223> OTHER INFORMATION: Where n is a, c, g or t
<220> FEATURE:
<221> NAME/KEY: modified_base
<222> LOCATION: (265)
<223> OTHER INFORMATION: Where n is a, c, g or t
<220> FEATURE:
<221> NAME/KEY: modified_base
<222> LOCATION: (280)
<223> OTHER INFORMATION: Where n is a, c, g or t
<220> FEATURE:
<221> NAME/KEY: modified_base
<222> LOCATION: (299)
<223> OTHER INFORMATION: Where n is a, c, g or t

<400> SEQUENCE: 95

```
tcgagcggcc gcccgggcag agtgtcgagc cagcgtcgcc gcgatggtgt tgttggagag      60
cgagcagttc ctgacggaac tgaccagact tttccanaag tgccggacgt cgggcancgt     120
ctatatcacc ttgaagaant atgacggtcg aaccaaaccc attccaaaga aangtactgt     180
gganggcttt gancccgcag acaacnagtg tctgttaaga actaccgatn ggaaanaana     240
anatcagcac tgtgggtgag ctccnaggga agttaataan tttcggatgg gcttattcna     300
acctcctta                                                              309

<210> SEQ ID NO 96
<211> LENGTH: 371
<212> TYPE: DNA
<213> ORGANISM: Human
<220> FEATURE:
<221> NAME/KEY: modified_base
<222> LOCATION: (327)
<223> OTHER INFORMATION: Where n is a, c, g or t

<400> SEQUENCE: 96
tcgagcggcc gcccgggcag gtccaccact cacctactcc ccgtctctat agatttgcct      60
gttctgggca gttctcagca atggaatcct actgtgtatc tttttgtgac tggttctta     120 actcagcatc acattttcaa ggttcatcca tgctgcagcc tggctccgta ctggtgacag     180
tacttcattt ctctctccct tttgttcaga ccaaggtctc cctctgtccc caaggctaaa     240
gtgcagttgg tgtgatcatg gctcactgca gcctcaaact cctggactca aacagtcctc     300
ccatctcagc ctcccaaagt gctgatntta taagttgcaa gccctgcacc cagcctgtat     360
ctccagtttg t                                                           371

<210> SEQ ID NO 97
<211> LENGTH: 430
<212> TYPE: DNA
<213> ORGANISM: Human
<220> FEATURE:
<221> NAME/KEY: modified_base
<222> LOCATION: (5)
<223> OTHER INFORMATION: Where n is a, c, g or t
<220> FEATURE:
<221> NAME/KEY: modified_base
<222> LOCATION: (25)
<223> OTHER INFORMATION: Where n is a, c, g or t
<220> FEATURE:
<221> NAME/KEY: modified_base
<222> LOCATION: (30)
<223> OTHER INFORMATION: Where n is a, c, g or t
<220> FEATURE:
<221> NAME/KEY: modified_base
<222> LOCATION: (34)
<223> OTHER INFORMATION: Where n is a, c, g or t
<220> FEATURE:
<221> NAME/KEY: modified_base
<222> LOCATION: (41)
<223> OTHER INFORMATION: Where n is a, c, g or t
<220> FEATURE:
<221> NAME/KEY: modified_base
<222> LOCATION: (42)
<223> OTHER INFORMATION: Where n is a, c, g or t
<220> FEATURE:
<221> NAME/KEY: modified_base
<222> LOCATION: (43)
<223> OTHER INFORMATION: Where n is a, c, g or t
<220> FEATURE:
<221> NAME/KEY: modified_base
<222> LOCATION: (44)
<223> OTHER INFORMATION: Where n is a, c, g or t
<220> FEATURE:
<221> NAME/KEY: modified_base
<222> LOCATION: (46)
<223> OTHER INFORMATION: Where n is a, c, g or t
```

```
<220> FEATURE:
<221> NAME/KEY: modified_base
<222> LOCATION: (60)
<223> OTHER INFORMATION: Where n is a, c, g or t
<220> FEATURE:
<221> NAME/KEY: modified_base
<222> LOCATION: (97)
<223> OTHER INFORMATION: Where n is a, c, g or t
<220> FEATURE:
<221> NAME/KEY: modified_base
<222> LOCATION: (116)
<223> OTHER INFORMATION: Where n is a, c, g or t
<220> FEATURE:
<221> NAME/KEY: modified_base
<222> LOCATION: (141)
<223> OTHER INFORMATION: Where n is a, c, g or t
<220> FEATURE:
<221> NAME/KEY: modified_base
<222> LOCATION: (145)
<223> OTHER INFORMATION: Where n is a, c, g or t
<220> FEATURE:
<221> NAME/KEY: modified_base
<222> LOCATION: (158)
<223> OTHER INFORMATION: Where n is a, c, g or t
<220> FEATURE:
<221> NAME/KEY: modified_base
<222> LOCATION: (183)
<223> OTHER INFORMATION: Where n is a, c, g or t
<220> FEATURE:
<221> NAME/KEY: modified_base
<222> LOCATION: (184)
<223> OTHER INFORMATION: Where n is a, c, g or t
<220> FEATURE:
<221> NAME/KEY: modified_base
<222> LOCATION: (226)
<223> OTHER INFORMATION: Where n is a, c, g or t
<220> FEATURE:
<221> NAME/KEY: modified_base
<222> LOCATION: (232)
<223> OTHER INFORMATION: Where n is a, c, g or t
<220> FEATURE:
<221> NAME/KEY: modified_base
<222> LOCATION: (243)
<223> OTHER INFORMATION: Where n is a, c, g or t
<220> FEATURE:
<221> NAME/KEY: modified_base
<222> LOCATION: (245)
<223> OTHER INFORMATION: Where n is a, c, g or t
<220> FEATURE:
<221> NAME/KEY: modified_base
<222> LOCATION: (257)
<223> OTHER INFORMATION: Where n is a, c, g or t
<220> FEATURE:
<221> NAME/KEY: modified_base
<222> LOCATION: (271)
<223> OTHER INFORMATION: Where n is a, c, g or t
<220> FEATURE:
<221> NAME/KEY: modified_base
<222> LOCATION: (288)
<223> OTHER INFORMATION: Where n is a, c, g or t
<220> FEATURE:
<221> NAME/KEY: modified_base
<222> LOCATION: (298)
<223> OTHER INFORMATION: Where n is a, c, g or t
<220> FEATURE:
<221> NAME/KEY: modified_base
<222> LOCATION: (300)
<223> OTHER INFORMATION: Where n is a, c, g or t
<220> FEATURE:
<221> NAME/KEY: modified_base
<222> LOCATION: (303)
<223> OTHER INFORMATION: Where n is a, c, g or t
<220> FEATURE:
<221> NAME/KEY: modified_base
<222> LOCATION: (308)
<223> OTHER INFORMATION: Where n is a, c, g or t
<220> FEATURE:
<221> NAME/KEY: modified_base
<222> LOCATION: (318)
```

<223> OTHER INFORMATION: Where n is a, c, g or t
<220> FEATURE:
<221> NAME/KEY: modified_base
<222> LOCATION: (325)
<223> OTHER INFORMATION: Where n is a, c, g or t
<220> FEATURE:
<221> NAME/KEY: modified_base
<222> LOCATION: (329)
<223> OTHER INFORMATION: Where n is a, c, g or t
<220> FEATURE:
<221> NAME/KEY: modified_base
<222> LOCATION: (354)
<223> OTHER INFORMATION: Where n is a, c, g or t
<220> FEATURE:
<221> NAME/KEY: modified_base
<222> LOCATION: (390)
<223> OTHER INFORMATION: Where n is a, c, g or t
<220> FEATURE:
<221> NAME/KEY: modified_base
<222> LOCATION: (428)
<223> OTHER INFORMATION: Where n is a, c, g or t

<400> SEQUENCE: 97

| | | | | | |
|---|---|---|---|---|---|
| tcgancggcc | gcccgggcag | gtttnttttn | tttnttttt | nnnngntagt | atttaaagan | 60 |
| atttattaaa | tcatcttatc | accaaaatgg | aaacatnttc | caactagaaa | catgcnacca | 120 |
| tcatcttccc | cagtccagtc | ncaangtcca | atattttnct | tgcctctgca | gataaaaagt | 180 |
| tcnnattttt | atacccactc | ttactccccc | ccaaaatttt | aattcngtcc | tncctaaaa | 240 |
| ttncnccggg | taacaantta | ccaaaatggc | naaccaatta | ttttaaanaa | aagttgcncn | 300 |
| ttnaaaangg | aaactttntg | gcaanttanc | ctcttttccc | ttcccacccc | ccantttaag | 360 |
| gggaaaacaa | tggcactttg | ctcttgcttn | aacccaaaat | tgtcttccaa | aaactattaa | 420 |
| aaatgttnaa | | | | | | 430 |

<210> SEQ ID NO 98
<211> LENGTH: 307
<212> TYPE: DNA
<213> ORGANISM: Human
<220> FEATURE:
<221> NAME/KEY: modified_base
<222> LOCATION: (3)
<223> OTHER INFORMATION: Where n is a, c, g or t
<220> FEATURE:
<221> NAME/KEY: modified_base
<222> LOCATION: (15)
<223> OTHER INFORMATION: Where n is a, c, g or t
<220> FEATURE:
<221> NAME/KEY: modified_base
<222> LOCATION: (19)
<223> OTHER INFORMATION: Where n is a, c, g or t
<220> FEATURE:
<221> NAME/KEY: modified_base
<222> LOCATION: (20)
<223> OTHER INFORMATION: Where n is a, c, g or t
<220> FEATURE:
<221> NAME/KEY: modified_base
<222> LOCATION: (25)
<223> OTHER INFORMATION: Where n is a, c, g or t
<220> FEATURE:
<221> NAME/KEY: modified_base
<222> LOCATION: (28)
<223> OTHER INFORMATION: Where n is a, c, g or t
<220> FEATURE:
<221> NAME/KEY: modified_base
<222> LOCATION: (43)
<223> OTHER INFORMATION: Where n is a, c, g or t
<220> FEATURE:
<221> NAME/KEY: modified_base
<222> LOCATION: (70)
<223> OTHER INFORMATION: Where n is a, c, g or t
<220> FEATURE:
<221> NAME/KEY: modified_base
<222> LOCATION: (75)
<223> OTHER INFORMATION: Where n is a, c, g or t
<220> FEATURE:
<221> NAME/KEY: modified_base
<222> LOCATION: (81)
<223> OTHER INFORMATION: Where n is a, c, g or t
<220> FEATURE:
<221> NAME/KEY: modified_base
<222> LOCATION: (102)
<223> OTHER INFORMATION: Where n is a, c, g or t
<220> FEATURE:
<221> NAME/KEY: modified_base
<222> LOCATION: (139)
<223> OTHER INFORMATION: Where n is a, c, g or t
<220> FEATURE:
<221> NAME/KEY: modified_base
<222> LOCATION: (162)
<223> OTHER INFORMATION: Where n is a, c, g or t
<220> FEATURE:
<221> NAME/KEY: modified_base
<222> LOCATION: (203)
<223> OTHER INFORMATION: Where n is a, c, g or t
<220> FEATURE:
<221> NAME/KEY: modified_base
<222> LOCATION: (259)
<223> OTHER INFORMATION: Where n is a, c, g or t
<220> FEATURE:
<221> NAME/KEY: modified_base
<222> LOCATION: (260)
<223> OTHER INFORMATION: Where n is a, c, g or t
<220> FEATURE:
<221> NAME/KEY: modified_base
<222> LOCATION: (283)
<223> OTHER INFORMATION: Where n is a, c, g or t
<220> FEATURE:
<221> NAME/KEY: modified_base
<222> LOCATION: (295)
<223> OTHER INFORMATION: Where n is a, c, g or t

<400> SEQUENCE: 98

```
tcnaacggcc gcccnggcnn gtctngcngc acctgtgcct canccgtcga tacctggtcg      60
attgggacan ggaanacaat ntggttttca gggaggccac anatttggag aaacggatga     120
attctccttt attccgaant cagctccttg gtctccgtag anggtgatct tgaaattctc     180
ctgttttgaa aactttcttg aanaaacctt acctgctggt tgtatttggt ctcccactcg     240
gacaagtact cgttatccnn ggtactctta atgtgcccac gtnaactccc cgggntggca     300
actggaa                                                               307
```

<210> SEQ ID NO 99
<211> LENGTH: 207
<212> TYPE: DNA
<213> ORGANISM: Human
<220> FEATURE:
<221> NAME/KEY: modified_base
<222> LOCATION: (5)
<223> OTHER INFORMATION: Where n is a, c, g or t
<220> FEATURE:
<221> NAME/KEY: modified_base
<222> LOCATION: (19)
<223> OTHER INFORMATION: Where n is a, c, g or t
<220> FEATURE:
<221> NAME/KEY: modified_base
<222> LOCATION: (24)
<223> OTHER INFORMATION: Where n is a, c, g or t
<220> FEATURE:
<221> NAME/KEY: modified_base
<222> LOCATION: (25)
<223> OTHER INFORMATION: Where n is a, c, g or t
<220> FEATURE:
<221> NAME/KEY: modified_base
<222> LOCATION: (38)
<223> OTHER INFORMATION: Where n is a, c, g or t
<220> FEATURE:

```
<221> NAME/KEY: modified_base
<222> LOCATION: (46)
<223> OTHER INFORMATION: Where n is a, c, g or t
<220> FEATURE:
<221> NAME/KEY: modified_base
<222> LOCATION: (59)
<223> OTHER INFORMATION: Where n is a, c, g or t
<220> FEATURE:
<221> NAME/KEY: modified_base
<222> LOCATION: (61)
<223> OTHER INFORMATION: Where n is a, c, g or t
<220> FEATURE:
<221> NAME/KEY: modified_base
<222> LOCATION: (66)
<223> OTHER INFORMATION: Where n is a, c, g or t
<220> FEATURE:
<221> NAME/KEY: modified_base
<222> LOCATION: (69)
<223> OTHER INFORMATION: Where n is a, c, g or t
<220> FEATURE:
<221> NAME/KEY: modified_base
<222> LOCATION: (81)
<223> OTHER INFORMATION: Where n is a, c, g or t
<220> FEATURE:
<221> NAME/KEY: modified_base
<222> LOCATION: (83)
<223> OTHER INFORMATION: Where n is a, c, g or t
<220> FEATURE:
<221> NAME/KEY: modified_base
<222> LOCATION: (88)
<223> OTHER INFORMATION: Where n is a, c, g or t
<220> FEATURE:
<221> NAME/KEY: modified_base
<222> LOCATION: (96)
<223> OTHER INFORMATION: Where n is a, c, g or t
<220> FEATURE:
<221> NAME/KEY: modified_base
<222> LOCATION: (98)
<223> OTHER INFORMATION: Where n is a, c, g or t
<220> FEATURE:
<221> NAME/KEY: modified_base
<222> LOCATION: (104)
<223> OTHER INFORMATION: Where n is a, c, g or t
<220> FEATURE:
<221> NAME/KEY: modified_base
<222> LOCATION: (106)
<223> OTHER INFORMATION: Where n is a, c, g or t
<220> FEATURE:
<221> NAME/KEY: modified_base
<222> LOCATION: (115)
<223> OTHER INFORMATION: Where n is a, c, g or t
<220> FEATURE:
<221> NAME/KEY: modified_base
<222> LOCATION: (126)
<223> OTHER INFORMATION: Where n is a, c, g or t
<220> FEATURE:
<221> NAME/KEY: modified_base
<222> LOCATION: (132)
<223> OTHER INFORMATION: Where n is a, c, g or t
<220> FEATURE:
<221> NAME/KEY: modified_base
<222> LOCATION: (135)
<223> OTHER INFORMATION: Where n is a, c, g or t
<220> FEATURE:
<221> NAME/KEY: modified_base
<222> LOCATION: (146)
<223> OTHER INFORMATION: Where n is a, c, g or t
<220> FEATURE:
<221> NAME/KEY: modified_base
<222> LOCATION: (152)
<223> OTHER INFORMATION: Where n is a, c, g or t
<220> FEATURE:
<221> NAME/KEY: modified_base
<222> LOCATION: (160)
<223> OTHER INFORMATION: Where n is a, c, g or t
<220> FEATURE:
<221> NAME/KEY: modified_base
<222> LOCATION: (165)
<223> OTHER INFORMATION: Where n is a, c, g or t
```

<220> FEATURE:
<221> NAME/KEY: modified_base
<222> LOCATION: (172)
<223> OTHER INFORMATION: Where n is a, c, g or t
<220> FEATURE:
<221> NAME/KEY: modified_base
<222> LOCATION: (173)
<223> OTHER INFORMATION: Where n is a, c, g or t
<220> FEATURE:
<221> NAME/KEY: modified_base
<222> LOCATION: (187)
<223> OTHER INFORMATION: Where n is a, c, g or t
<220> FEATURE:
<221> NAME/KEY: modified_base
<222> LOCATION: (188)
<223> OTHER INFORMATION: Where n is a, c, g or t
<220> FEATURE:
<221> NAME/KEY: modified_base
<222> LOCATION: (189)
<223> OTHER INFORMATION: Where n is a, c, g or t
<220> FEATURE:
<221> NAME/KEY: modified_base
<222> LOCATION: (192)
<223> OTHER INFORMATION: Where n is a, c, g or t
<220> FEATURE:
<221> NAME/KEY: modified_base
<222> LOCATION: (202)
<223> OTHER INFORMATION: Where n is a, c, g or t
<220> FEATURE:
<221> NAME/KEY: modified_base
<222> LOCATION: (203)
<223> OTHER INFORMATION: Where n is a, c, g or t

<400> SEQUENCE: 99
gtccnggacc gatgttgcna agannntttct tggtccanta ggttcnaaaa aatgataanc     60
naggtntanc acgtgaagat ntntatanag tcttantnaa aacncntaga tctgnatgac    120
gataantcga anacngggggg aggggntgag gngaggtggn gtganggaag anntgttgat    180
aaaagannna gntgataaga anngagc                                         207

<210> SEQ ID NO 100
<211> LENGTH: 200
<212> TYPE: DNA
<213> ORGANISM: Human
<220> FEATURE:
<221> NAME/KEY: modified_base
<222> LOCATION: (3)
<223> OTHER INFORMATION: Where n is a, c, g or t
<220> FEATURE:
<221> NAME/KEY: modified_base
<222> LOCATION: (5)
<223> OTHER INFORMATION: Where n is a, c, g or t
<220> FEATURE:
<221> NAME/KEY: modified_base
<222> LOCATION: (6)
<223> OTHER INFORMATION: Where n is a, c, g or t
<220> FEATURE:
<221> NAME/KEY: modified_base
<222> LOCATION: (14)
<223> OTHER INFORMATION: Where n is a, c, g or t
<220> FEATURE:
<221> NAME/KEY: modified_base
<222> LOCATION: (21)
<223> OTHER INFORMATION: Where n is a, c, g or t
<220> FEATURE:
<221> NAME/KEY: modified_base
<222> LOCATION: (23)
<223> OTHER INFORMATION: Where n is a, c, g or t
<220> FEATURE:
<221> NAME/KEY: modified_base
<222> LOCATION: (29)
<223> OTHER INFORMATION: Where n is a, c, g or t
<220> FEATURE:
<221> NAME/KEY: modified_base
<222> LOCATION: (46)

```
<223> OTHER INFORMATION: Where n is a, c, g or t
<220> FEATURE:
<221> NAME/KEY: modified_base
<222> LOCATION: (71)
<223> OTHER INFORMATION: Where n is a, c, g or t
<220> FEATURE:
<221> NAME/KEY: modified_base
<222> LOCATION: (150)
<223> OTHER INFORMATION: Where n is a, c, g or t
<220> FEATURE:
<221> NAME/KEY: modified_base
<222> LOCATION: (151)
<223> OTHER INFORMATION: Where n is a, c, g or t
<220> FEATURE:
<221> NAME/KEY: modified_base
<222> LOCATION: (166)
<223> OTHER INFORMATION: Where n is a, c, g or t
<220> FEATURE:
<221> NAME/KEY: modified_base
<222> LOCATION: (176)
<223> OTHER INFORMATION: Where n is a, c, g or t
<220> FEATURE:
<221> NAME/KEY: modified_base
<222> LOCATION: (185)
<223> OTHER INFORMATION: Where n is a, c, g or t
<220> FEATURE:
<221> NAME/KEY: modified_base
<222> LOCATION: (186)
<223> OTHER INFORMATION: Where n is a, c, g or t
<220> FEATURE:
<221> NAME/KEY: modified_base
<222> LOCATION: (195)
<223> OTHER INFORMATION: Where n is a, c, g or t

<400> SEQUENCE: 100
acntnnacta gaantaacag ncnttctang aacactacca tctgtnttca catgaaatgc      60
cacacacata naaactccaa catcaatttc attgcacaga ctgactgtaa ttaattttgt     120
cacaggaatc tatggactga atctaatgcn nccccaaatg ttgttngttt gcaatntcaa     180
acatnnttat tccancagat                                                 200

<210> SEQ ID NO 101
<211> LENGTH: 51
<212> TYPE: DNA
<213> ORGANISM: Human
<220> FEATURE:
<221> NAME/KEY: modified_base
<222> LOCATION: (35)
<223> OTHER INFORMATION: Where n is a, c, g or t

<400> SEQUENCE: 101
tcgagcggcc gcccgggcag gtctgaccag tgganaaatg cccagttatt g              51

<210> SEQ ID NO 102
<211> LENGTH: 385
<212> TYPE: DNA
<213> ORGANISM: Human
<220> FEATURE:
<221> NAME/KEY: modified_base
<222> LOCATION: (50)
<223> OTHER INFORMATION: Where n is a, c, g or t
<220> FEATURE:
<221> NAME/KEY: modified_base
<222> LOCATION: (145)
<223> OTHER INFORMATION: Where n is a, c, g or t
<220> FEATURE:
<221> NAME/KEY: modified_base
<222> LOCATION: (202)
<223> OTHER INFORMATION: Where n is a, c, g or t
<220> FEATURE:
<221> NAME/KEY: modified_base
<222> LOCATION: (214)
<223> OTHER INFORMATION: Where n is a, c, g or t
```

```
<220> FEATURE:
<221> NAME/KEY: modified_base
<222> LOCATION: (306)
<223> OTHER INFORMATION: Where n is a, c, g or t
<220> FEATURE:
<221> NAME/KEY: modified_base
<222> LOCATION: (362)
<223> OTHER INFORMATION: Where n is a, c, g or t

<400> SEQUENCE: 102
aacgtggtcg cggccgaagt ccatggtgct gggattaatc cactgtgacn gtgactctga      60
gttgagttgt ttttcaatct tctccaagcc tgtggactca tcctccacat ccttgggtag     120
taggatgaac atgctgaaga tgctnatttt gaaaaggaac tctatgaatc ttacaattga     180
atactgtcaa tgtttcccca tnacagaacg tggnccccca aggttccatc atctgcactg     240
ggtttgggtg ttctgtcttg gttgactctt gaaaagggac atttcttttt gttttcttga     300
attcanggaa attttcttca tccactttgc ccacaaaagt taggcagcat ttaaccccca     360
anggattttg ggtctgggtc cttcc                                           385

<210> SEQ ID NO 103
<211> LENGTH: 189
<212> TYPE: DNA
<213> ORGANISM: Human
<220> FEATURE:
<221> NAME/KEY: modified_base
<222> LOCATION: (72)
<223> OTHER INFORMATION: Where n is a, c, g or t
<220> FEATURE:
<221> NAME/KEY: modified_base
<222> LOCATION: (138)
<223> OTHER INFORMATION: Where n is a, c, g or t
<220> FEATURE:
<221> NAME/KEY: modified_base
<222> LOCATION: (156)
<223> OTHER INFORMATION: Where n is a, c, g or t

<400> SEQUENCE: 103
agcgtggtcg cggccgaagt ctgcagcctg ggactgaccg ggaagctctg attatttacc      60
caccacaggt angttgtgtt ctgaatctca agttcacagg ttaaggctac agcatcctca     120
tcctccacgg ggttggantt gttgctggtg atgaanggtt tggggtggct ctgcataact     180
gttgatctc                                                             189

<210> SEQ ID NO 104
<211> LENGTH: 181
<212> TYPE: DNA
<213> ORGANISM: Human
<220> FEATURE:
<221> NAME/KEY: modified_base
<222> LOCATION: (38)
<223> OTHER INFORMATION: Where n is a, c, g or t
<220> FEATURE:
<221> NAME/KEY: modified_base
<222> LOCATION: (82)
<223> OTHER INFORMATION: Where n is a, c, g or t
<220> FEATURE:
<221> NAME/KEY: modified_base
<222> LOCATION: (83)
<223> OTHER INFORMATION: Where n is a, c, g or t
<220> FEATURE:
<221> NAME/KEY: modified_base
<222> LOCATION: (97)
<223> OTHER INFORMATION: Where n is a, c, g or t

<400> SEQUENCE: 104
tcgagcggcc gcccgggcag gtccaggtct ccaccaangc accaccgtgg gaagctggta      60
```

| | |
|---|---|
| attgatgccc accttgaagc cnntgggca ccatccncca actggatgct gcgcttggtt | 120 |
| ttgatggtgg caatggcaca ttgactcttt tgggaaccac ttcaccacgg tacaacaggc | 180 |
| a | 181 |

<210> SEQ ID NO 105
<211> LENGTH: 327
<212> TYPE: DNA
<213> ORGANISM: Human
<220> FEATURE:
<221> NAME/KEY: modified_base
<222> LOCATION: (80)
<223> OTHER INFORMATION: Where n is a, c, g or t
<220> FEATURE:
<221> NAME/KEY: modified_base
<222> LOCATION: (116)
<223> OTHER INFORMATION: Where n is a, c, g or t
<220> FEATURE:
<221> NAME/KEY: modified_base
<222> LOCATION: (167)
<223> OTHER INFORMATION: Where n is a, c, g or t
<220> FEATURE:
<221> NAME/KEY: modified_base
<222> LOCATION: (175)
<223> OTHER INFORMATION: Where n is a, c, g or t
<220> FEATURE:
<221> NAME/KEY: modified_base
<222> LOCATION: (182)
<223> OTHER INFORMATION: Where n is a, c, g or t
<220> FEATURE:
<221> NAME/KEY: modified_base
<222> LOCATION: (194)
<223> OTHER INFORMATION: Where n is a, c, g or t
<220> FEATURE:
<221> NAME/KEY: modified_base
<222> LOCATION: (210)
<223> OTHER INFORMATION: Where n is a, c, g or t
<220> FEATURE:
<221> NAME/KEY: modified_base
<222> LOCATION: (277)
<223> OTHER INFORMATION: Where n is a, c, g or t

<400> SEQUENCE: 105

| | |
|---|---|
| tcgagcggcc gcccgggcag gtcttctgtg gagtctgcgt gggcatcgtg ggcagtgggg | 60 |
| ctgccctggc cgatgctcan aaccccagcc tctttgtaaa gattctcatc gtgganatct | 120 |
| ttggcagcgc cattggcctc tttgggtca tcgtcgcaat tcttcanacc tccanaatga | 180 |
| anatgggtga ctanataata tgtgtgggtn gggccgtgcc tcacttttat ttattgctgg | 240 |
| ttttcctggg acagaactcg ggcgcgaaca cgcttanccg aattccaaca cactggcggg | 300 |
| cgttactagt ggatccgagc tcggtac | 327 |

<210> SEQ ID NO 106
<211> LENGTH: 268
<212> TYPE: DNA
<213> ORGANISM: Human
<220> FEATURE:
<221> NAME/KEY: modified_base
<222> LOCATION: (18)
<223> OTHER INFORMATION: Where n is a, c, g or t
<220> FEATURE:
<221> NAME/KEY: modified_base
<222> LOCATION: (73)
<223> OTHER INFORMATION: Where n is a, c, g or t
<220> FEATURE:
<221> NAME/KEY: modified_base
<222> LOCATION: (96)
<223> OTHER INFORMATION: Where n is a, c, g or t
<220> FEATURE:
<221> NAME/KEY: modified_base
<222> LOCATION: (113)
<223> OTHER INFORMATION: Where n is a, c, g or t

```
<220> FEATURE:
<221> NAME/KEY: modified_base
<222> LOCATION: (129)
<223> OTHER INFORMATION: Where n is a, c, g or t
<220> FEATURE:
<221> NAME/KEY: modified_base
<222> LOCATION: (161)
<223> OTHER INFORMATION: Where n is a, c, g or t
<220> FEATURE:
<221> NAME/KEY: modified_base
<222> LOCATION: (195)
<223> OTHER INFORMATION: Where n is a, c, g or t
<220> FEATURE:
<221> NAME/KEY: modified_base
<222> LOCATION: (219)
<223> OTHER INFORMATION: Where n is a, c, g or t
<220> FEATURE:
<221> NAME/KEY: modified_base
<222> LOCATION: (247)
<223> OTHER INFORMATION: Where n is a, c, g or t
<220> FEATURE:
<221> NAME/KEY: modified_base
<222> LOCATION: (250)
<223> OTHER INFORMATION: Where n is a, c, g or t
<220> FEATURE:
<221> NAME/KEY: modified_base
<222> LOCATION: (255)
<223> OTHER INFORMATION: Where n is a, c, g or t
<220> FEATURE:
<221> NAME/KEY: modified_base
<222> LOCATION: (257)
<223> OTHER INFORMATION: Where n is a, c, g or t

<400> SEQUENCE: 106
agcgtggtcg cggccgangt ctggcgtgtg ccacatcggt cccacctcgc tttacaaaac      60
agtcctgaac ttnatctaat aaaattattg tacacnacat ttacattaga aaaaganagc     120
tgggtgtang aaaccgggcc tggtgttccc tttaagcgaa ngtggctcca cagttggggc     180
atcgtcgctt cctcnaagca aaaacgccaa tgaaccccna aggggaaaaa aggaatgaag     240
gaactgnccn gggangnccg ctccgaaa                                        268

<210> SEQ ID NO 107
<211> LENGTH: 353
<212> TYPE: DNA
<213> ORGANISM: Human
<220> FEATURE:
<221> NAME/KEY: modified_base
<222> LOCATION: (70)
<223> OTHER INFORMATION: Where n is a, c, g or t
<220> FEATURE:
<221> NAME/KEY: modified_base
<222> LOCATION: (167)
<223> OTHER INFORMATION: Where n is a, c, g or t
<220> FEATURE:
<221> NAME/KEY: modified_base
<222> LOCATION: (179)
<223> OTHER INFORMATION: Where n is a, c, g or t
<220> FEATURE:
<221> NAME/KEY: modified_base
<222> LOCATION: (184)
<223> OTHER INFORMATION: Where n is a, c, g or t
<220> FEATURE:
<221> NAME/KEY: modified_base
<222> LOCATION: (185)
<223> OTHER INFORMATION: Where n is a, c, g or t
<220> FEATURE:
<221> NAME/KEY: modified_base
<222> LOCATION: (196)
<223> OTHER INFORMATION: Where n is a, c, g or t
<220> FEATURE:
<221> NAME/KEY: modified_base
<222> LOCATION: (198)
<223> OTHER INFORMATION: Where n is a, c, g or t
<220> FEATURE:
```

```
<221> NAME/KEY: modified_base
<222> LOCATION: (215)
<223> OTHER INFORMATION: Where n is a, c, g or t
<220> FEATURE:
<221> NAME/KEY: modified_base
<222> LOCATION: (216)
<223> OTHER INFORMATION: Where n is a, c, g or t
<220> FEATURE:
<221> NAME/KEY: modified_base
<222> LOCATION: (221)
<223> OTHER INFORMATION: Where n is a, c, g or t
<220> FEATURE:
<221> NAME/KEY: modified_base
<222> LOCATION: (235)
<223> OTHER INFORMATION: Where n is a, c, g or t
<220> FEATURE:
<221> NAME/KEY: modified_base
<222> LOCATION: (286)
<223> OTHER INFORMATION: Where n is a, c, g or t
<220> FEATURE:
<221> NAME/KEY: modified_base
<222> LOCATION: (288)
<223> OTHER INFORMATION: Where n is a, c, g or t
<220> FEATURE:
<221> NAME/KEY: modified_base
<222> LOCATION: (299)
<223> OTHER INFORMATION: Where n is a, c, g or t
<220> FEATURE:
<221> NAME/KEY: modified_base
<222> LOCATION: (312)
<223> OTHER INFORMATION: Where n is a, c, g or t
<220> FEATURE:
<221> NAME/KEY: modified_base
<222> LOCATION: (321)
<223> OTHER INFORMATION: Where n is a, c, g or t
<220> FEATURE:
<221> NAME/KEY: modified_base
<222> LOCATION: (335)
<223> OTHER INFORMATION: Where n is a, c, g or t
<220> FEATURE:
<221> NAME/KEY: modified_base
<222> LOCATION: (344)
<223> OTHER INFORMATION: Where n is a, c, g or t

<400> SEQUENCE: 107
tcgagcggcc gcccgggcag gtggccaggc catgttatgg gatctcaacg aaggcaaaca     60
cctttacacn ctagatggtg gggacatcat caacgccctg tgcttcagcc ctaaccgcta    120
ctggctgtgt gctgccgcag gccccagcat caagatctgg gatttanagg gaaagatcnt    180
tgtnnatgaa ctgaancnta aattatcagt tccannacca ngcaaaaacc acccngtgca    240
ctccctggcc tggtctgctg atgggacctc gggcgcgaac acgctnancc caattccanc    300
acactgggcg gncgttacta ntggatccga actcnggtac caancttggc gtt           353

<210> SEQ ID NO 108
<211> LENGTH: 360
<212> TYPE: DNA
<213> ORGANISM: Human
<220> FEATURE:
<221> NAME/KEY: modified_base
<222> LOCATION: (61)
<223> OTHER INFORMATION: Where n is a, c, g or t
<220> FEATURE:
<221> NAME/KEY: modified_base
<222> LOCATION: (121)
<223> OTHER INFORMATION: Where n is a, c, g or t
<220> FEATURE:
<221> NAME/KEY: modified_base
<222> LOCATION: (145)
<223> OTHER INFORMATION: Where n is a, c, g or t
<220> FEATURE:
<221> NAME/KEY: modified_base
<222> LOCATION: (194)
<223> OTHER INFORMATION: Where n is a, c, g or t
```

<220> FEATURE:
<221> NAME/KEY: modified_base
<222> LOCATION: (202)
<223> OTHER INFORMATION: Where n is a, c, g or t
<220> FEATURE:
<221> NAME/KEY: modified_base
<222> LOCATION: (217)
<223> OTHER INFORMATION: Where n is a, c, g or t
<220> FEATURE:
<221> NAME/KEY: modified_base
<222> LOCATION: (237)
<223> OTHER INFORMATION: Where n is a, c, g or t
<220> FEATURE:
<221> NAME/KEY: modified_base
<222> LOCATION: (252)
<223> OTHER INFORMATION: Where n is a, c, g or t
<220> FEATURE:
<221> NAME/KEY: modified_base
<222> LOCATION: (254)
<223> OTHER INFORMATION: Where n is a, c, g or t
<220> FEATURE:
<221> NAME/KEY: modified_base
<222> LOCATION: (275)
<223> OTHER INFORMATION: Where n is a, c, g or t
<220> FEATURE:
<221> NAME/KEY: modified_base
<222> LOCATION: (279)
<223> OTHER INFORMATION: Where n is a, c, g or t
<220> FEATURE:
<221> NAME/KEY: modified_base
<222> LOCATION: (318)
<223> OTHER INFORMATION: Where n is a, c, g or t
<220> FEATURE:
<221> NAME/KEY: modified_base
<222> LOCATION: (330)
<223> OTHER INFORMATION: Where n is a, c, g or t
<220> FEATURE:
<221> NAME/KEY: modified_base
<222> LOCATION: (343)
<223> OTHER INFORMATION: Where n is a, c, g or t
<220> FEATURE:
<221> NAME/KEY: modified_base
<222> LOCATION: (346)
<223> OTHER INFORMATION: Where n is a, c, g or t
<220> FEATURE:
<221> NAME/KEY: modified_base
<222> LOCATION: (352)
<223> OTHER INFORMATION: Where n is a, c, g or t

<400> SEQUENCE: 108
agcgtggtcg cggccgaagt cctggcctca catgaccctg ctccagcaac ttgaacagga      60
naagcagcag ctacatcctt aaggtccgga aagttagatg aagatttgga tcctgcattg     120
ncctgcctcc cacctatctc tcccnaatta taaacagcct ccttgggaag cagcagaatt     180
taaaaactct cccnctgccc tnttgaacta cacaccnacc gggaaaacct ttttcanaat     240
ggcacaaaaa tncnagggaa tgcatttcca tgaangaana aactgggtta cccaaaatta     300
ttgggttggg gaaatccngg gggggttttn aaaaagggc aanccnccaa anaaaaaaac      360

<210> SEQ ID NO 109
<211> LENGTH: 101
<212> TYPE: DNA
<213> ORGANISM: Human
<220> FEATURE:
<221> NAME/KEY: modified_base
<222> LOCATION: (10)
<223> OTHER INFORMATION: Where n is a, c, g or t
<220> FEATURE:
<221> NAME/KEY: modified_base
<222> LOCATION: (47)
<223> OTHER INFORMATION: Where n is a, c, g or t
<220> FEATURE:
<221> NAME/KEY: modified_base
<222> LOCATION: (77)

```
<223> OTHER INFORMATION: Where n is a, c, g or t
<220> FEATURE:
<221> NAME/KEY: modified_base
<222> LOCATION: (82)
<223> OTHER INFORMATION: Where n is a, c, g or t

<400> SEQUENCE: 109
atcgtggtcn cggccgaagt cctgtgtcct ggatgggccg tgtgcancga atccgttggc    60
gactcctaac taccaanaaa angactctcg gaagaaattt c                      101

<210> SEQ ID NO 110
<211> LENGTH: 300
<212> TYPE: DNA
<213> ORGANISM: Human
<220> FEATURE:
<221> NAME/KEY: modified_base
<222> LOCATION: (4)
<223> OTHER INFORMATION: Where n is a, c, g or t
<220> FEATURE:
<221> NAME/KEY: modified_base
<222> LOCATION: (56)
<223> OTHER INFORMATION: Where n is a, c, g or t
<220> FEATURE:
<221> NAME/KEY: modified_base
<222> LOCATION: (116)
<223> OTHER INFORMATION: Where n is a, c, g or t
<220> FEATURE:
<221> NAME/KEY: modified_base
<222> LOCATION: (130)
<223> OTHER INFORMATION: Where n is a, c, g or t
<220> FEATURE:
<221> NAME/KEY: modified_base
<222> LOCATION: (236)
<223> OTHER INFORMATION: Where n is a, c, g or t
<220> FEATURE:
<221> NAME/KEY: modified_base
<222> LOCATION: (243)
<223> OTHER INFORMATION: Where n is a, c, g or t
<220> FEATURE:
<221> NAME/KEY: modified_base
<222> LOCATION: (246)
<223> OTHER INFORMATION: Where n is a, c, g or t
<220> FEATURE:
<221> NAME/KEY: modified_base
<222> LOCATION: (248)
<223> OTHER INFORMATION: Where n is a, c, g or t
<220> FEATURE:
<221> NAME/KEY: modified_base
<222> LOCATION: (271)
<223> OTHER INFORMATION: Where n is a, c, g or t
<220> FEATURE:
<221> NAME/KEY: modified_base
<222> LOCATION: (276)
<223> OTHER INFORMATION: Where n is a, c, g or t
<220> FEATURE:
<221> NAME/KEY: modified_base
<222> LOCATION: (280)
<223> OTHER INFORMATION: Where n is a, c, g or t

<400> SEQUENCE: 110
ccanggaaac ccagagtcac atgagatagg gtggctttcg ggacaggggg tcagangaat    60
ggtacatgga tctcagcccc tgatggacac ggaacaggtg tggtcagaac tcccangatt   120
ctgcatccan gatccagtct ctatagaagt tatggatcat tccttcattt cattcccccc   180
ttcatgaaaa aacttctgaa caagcctttt ttctcacttt ggggccctgt ttggcncaag   240
gtnttnantt ggggaaaaaa aaacaaatcc nttccnttan ccctccgtgg ggaatgacct   300

<210> SEQ ID NO 111
<211> LENGTH: 366
<212> TYPE: DNA
<213> ORGANISM: Human
```

```
<220> FEATURE:
<221> NAME/KEY: modified_base
<222> LOCATION: (42)
<223> OTHER INFORMATION: Where n is a, c, g or t
<220> FEATURE:
<221> NAME/KEY: modified_base
<222> LOCATION: (65)
<223> OTHER INFORMATION: Where n is a, c, g or t
<220> FEATURE:
<221> NAME/KEY: modified_base
<222> LOCATION: (90)
<223> OTHER INFORMATION: Where n is a, c, g or t
<220> FEATURE:
<221> NAME/KEY: modified_base
<222> LOCATION: (180)
<223> OTHER INFORMATION: Where n is a, c, g or t
<220> FEATURE:
<221> NAME/KEY: modified_base
<222> LOCATION: (250)
<223> OTHER INFORMATION: Where n is a, c, g or t
<220> FEATURE:
<221> NAME/KEY: modified_base
<222> LOCATION: (257)
<223> OTHER INFORMATION: Where n is a, c, g or t
<220> FEATURE:
<221> NAME/KEY: modified_base
<222> LOCATION: (264)
<223> OTHER INFORMATION: Where n is a, c, g or t
<220> FEATURE:
<221> NAME/KEY: modified_base
<222> LOCATION: (296)
<223> OTHER INFORMATION: Where n is a, c, g or t
<220> FEATURE:
<221> NAME/KEY: modified_base
<222> LOCATION: (333)
<223> OTHER INFORMATION: Where n is a, c, g or t
<220> FEATURE:
<221> NAME/KEY: modified_base
<222> LOCATION: (337)
<223> OTHER INFORMATION: Where n is a, c, g or t

<400> SEQUENCE: 111
cgagcggccg cccgggcagg tccttgtgtt gccatctgtt ancattgatt tctggaatgg      60
aacanctttc tcaaagtttg gtcttgctan tcatgaagtc atgtcagtgt cttaagtcac     120
tgctgctcac ttccttaccc agggaatata ctgcataagt ttctgaacac ctgtttttcan   180 tattcactgt tcctctcctg cccaaaattg gaagggacct catttaaaaa tcaaatttga    240
atcctgaaan aaaaacngga aatntttctc ttggaatttg gaatagaatt attcanttga    300
ataacatgtt ttttcccctt gccttgctct tcncaanaac atctggacct cggccgcgac    360
acctta                                                                366

<210> SEQ ID NO 112
<211> LENGTH: 405
<212> TYPE: DNA
<213> ORGANISM: Human
<220> FEATURE:
<221> NAME/KEY: modified_base
<222> LOCATION: (7)
<223> OTHER INFORMATION: Where n is a, c, g or t
<220> FEATURE:
<221> NAME/KEY: modified_base
<222> LOCATION: (23)
<223> OTHER INFORMATION: Where n is a, c, g or t
<220> FEATURE:
<221> NAME/KEY: modified_base
<222> LOCATION: (29)
<223> OTHER INFORMATION: Where n is a, c, g or t
<220> FEATURE:
<221> NAME/KEY: modified_base
<222> LOCATION: (52)
<223> OTHER INFORMATION: Where n is a, c, g or t
<220> FEATURE:
```

-continued

```
<221> NAME/KEY: modified_base
<222> LOCATION: (119)
<223> OTHER INFORMATION: Where n is a, c, g or t
<220> FEATURE:
<221> NAME/KEY: modified_base
<222> LOCATION: (136)
<223> OTHER INFORMATION: Where n is a, c, g or t
<220> FEATURE:
<221> NAME/KEY: modified_base
<222> LOCATION: (139)
<223> OTHER INFORMATION: Where n is a, c, g or t
<220> FEATURE:
<221> NAME/KEY: modified_base
<222> LOCATION: (147)
<223> OTHER INFORMATION: Where n is a, c, g or t
<220> FEATURE:
<221> NAME/KEY: modified_base
<222> LOCATION: (172)
<223> OTHER INFORMATION: Where n is a, c, g or t
<220> FEATURE:
<221> NAME/KEY: modified_base
<222> LOCATION: (204)
<223> OTHER INFORMATION: Where n is a, c, g or t
<220> FEATURE:
<221> NAME/KEY: modified_base
<222> LOCATION: (232)
<223> OTHER INFORMATION: Where n is a, c, g or t
<220> FEATURE:
<221> NAME/KEY: modified_base
<222> LOCATION: (247)
<223> OTHER INFORMATION: Where n is a, c, g or t
<220> FEATURE:
<221> NAME/KEY: modified_base
<222> LOCATION: (320)
<223> OTHER INFORMATION: Where n is a, c, g or t
<220> FEATURE:
<221> NAME/KEY: modified_base
<222> LOCATION: (323)
<223> OTHER INFORMATION: Where n is a, c, g or t
<220> FEATURE:
<221> NAME/KEY: modified_base
<222> LOCATION: (324)
<223> OTHER INFORMATION: Where n is a, c, g or t
<220> FEATURE:
<221> NAME/KEY: modified_base
<222> LOCATION: (362)
<223> OTHER INFORMATION: Where n is a, c, g or t
<220> FEATURE:
<221> NAME/KEY: modified_base
<222> LOCATION: (386)
<223> OTHER INFORMATION: Where n is a, c, g or t

<400> SEQUENCE: 112
ctgactncta aacttctaat tcnatcaana taactactct ccttccgtct tncagagtgt      60
tcacaataaa tctgtgaatc tggcatacac agttgctgga aaattgttct tcctccacna    120
aaaggtcaat tgttcnccnc atgaaanaag ataaattgtt catccatcac tnctgaacca    180
tccaaaacgc cggcggaatt attncccgt tattatgggg aacggaattt tnaataaatt     240
tgggaangaa tggggctttt attgttttgt tttccccctt tcttggcatt gattgggccg    300
caatgggccc cctcgctcan aanntgcccc ggggccggcc gctccaaaac cgaaattccc    360
anccacactt ggcgggccgt tactanttgg atccgaactc ggtta                    405
```

COMPOUNDS FOR IMMUNOTHERAPY AND DIAGNOSIS OF COLON CANCER AND METHODS FOR THEIR USE

TECHNICAL FIELD

The present invention relates generally to compositions and methods for the treatment and diagnosis of colon cancer. The invention is more specifically related to nucleotide sequences that are preferentially expressed in colon tumor tissue, together with polypeptides encoded by such nucleotide sequences. The inventive nucleotide sequences and polypeptides may be used in vaccines and pharmaceutical compositions for the treatment and diagnosis of colon cancer.

BACKGROUND OF THE INVENTION

Colon cancer is the second most frequently diagnosed malignancy in the United States as well as the second most common cause of cancer death. An estimated 95,600 new cases of colon cancer will be diagnosed in 1998, with an estimated 47,700 deaths. The five-year survival rate for patients with colorectal cancer detected in an early localized stage is 92%; unfortunately, only 37% of colorectal cancer is diagnosed at this stage. The survival rate drops to 64% if the cancer is allowed to spread to adjacent organs or lymph nodes, and to 7% in patients with distant metastases.

The prognosis of colon cancer is directly related to the degree of penetration of the tumor through the bowel wall and the presence or absence of nodal involvement, consequently, early detection and treatment are especially important. Currently, diagnosis is aided by the use of screening assays for fecal occult blood, sigmoidoscopy, colonoscopy and double contrast barium enemas. Treatment regimens are determined by the type and stage of the cancer, and include surgery, radiation therapy and/or chemotherapy. Recurrence following surgery (the most common form of therapy) is a major problem and is often the ultimate cause of death. In spite of considerable research into therapies for the disease, colon cancer remains difficult to diagnose and treat.

Accordingly, there remains a need in the art for improved vaccines, treatment methods and diagnostic techniques for colon cancer.

SUMMARY OF THE INVENTION

Briefly stated, the present invention provides compounds and methods for the therapy and diagnosis of colon cancer. In a first aspect, isolated polynucleotide molecules encoding colon tumor polypeptides are provided, such polynucleotide molecules comprising one of the following nucleotide sequences: (a) sequences provided in SEQ ID NO: 2, 8, 15, 16, 22, 24, 30, 32–34, 36, 38, 40, 41, 46–49, 52, 54, 59, 60, 65–69, 79, 89, 90, 93, 99–101 and 109–111; (b) sequences complementary to a sequence provided in SEQ ID NO: 2, 8, 15, 16, 22, 24, 30, 32–34, 36, 38, 40, 41, 46–49, 52, 54, 59, 60, 65–69, 79, 89, 90, 93, 99–101 and 109–111; and (c) sequences that hybridize to a sequence of (a) or (b) under moderately stringent conditions.

In a second aspect, isolated polypeptides are provided that comprise at least an immunogenic portion of a colon tumor protein or a variant thereof. In specific embodiments, such polypeptides comprise an amino acid sequence encoded by a polynucleotide molecule comprising one of the following nucleotide sequences: (a) sequences recited in SEQ ID NO: 2, 8, 15, 16, 22, 24, 30, 32–34, 36, 38, 40, 41, 46–49, 52, 54, 59, 60, 65–69, 79, 89, 90, 93, 99–101 and 109–111; (b) sequences complementary to a sequence provided in SEQ ID NO: 2, 8, 15, 16, 22, 24, 30, 32–34, 36, 38, 40, 41, 46–49, 52, 54, 59, 60, 65–69, 79, 89, 90, 93, 99–101 and 109–111; and (c) sequences that hybridize to a sequence of (a) or (b) under moderately stringent conditions.

In related aspects, expression vectors comprising the inventive polynucleotide molecules, together with host cells transformed or transfected with such expression vectors are provided. In preferred embodiments, the host cells may be *E. coli*, yeast and mammalian cells.

In another aspect, fusion proteins comprising a first and a second inventive polypeptide or, alternatively, an inventive polypeptide and a known colon tumor antigen, are provided.

The present invention further provides pharmaceutical compositions comprising one or more of the above polypeptides, fusion proteins or polynucleotide molecules and a physiologically acceptable carrier, together with vaccines comprising one or more such polypeptides, fusion proteins or polynucleotide molecules in combination with an immune response enhancer.

In related aspects, the present invention provides methods for inhibiting the development of colon cancer in a patient, comprising administering to a patient an effective amount of at least one of the above pharmaceutical compositions and/or vaccines.

Additionally, the present invention provides methods for immunodiagnosis of colon cancer, together with kits for use in such methods. Polypeptides are disclosed which comprise at least an immunogenic portion of a colon tumor protein or a variant of said protein that differs only in conservative substitutions and/or modifications, wherein the colon tumor protein comprises an amino acid sequence encoded by a polynucleotide molecule having one of the following nucleotide sequences recited in SEQ ID NO: 1–112, and variants thereof Such polypeptides may be usefully employed in the diagnosis and monitoring of colon cancer.

In one specific aspect of the present invention, methods are provided for detecting colon cancer in a patient, comprising: (a) contacting a biological sample obtained from a patient with a binding agent that is capable of binding to one of the above polypeptides; and (b) detecting in the sample a protein or polypeptide that binds to the binding agent. In preferred embodiments, the binding agent is an antibody, most preferably a monoclonal antibody.

In related aspects, methods are provided for monitoring the progression of colon cancer in a patient, comprising: (a) contacting a biological sample obtained from a patient with a binding agent that is capable of binding to one of the above polypeptides; (b) determining in the sample an amount of a protein or polypeptide that binds to the binding agent; (c) repeating steps (a) and (b); and comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of colon cancer.

The present invention further provides methods for detecting colon cancer comprising: (a) obtaining a biological sample from a patient; (b) contacting the sample with a first and a second oligonucleotide primer in a polymerase chain reaction, at least one of the oligonucleotide primers being specific for a polynucleotide molecule that encodes one of the above polypeptides; and (c) detecting in the sample a polynucleotide sequence that amplifies in the presence of the first and second oligonucleotide primers. In a preferred embodiment, at least one of the oligonucleotide primers comprises at least about 10 contiguous nucleotides of a polynucleotide molecule, such as those sequences from SEQ ID NO: 1–112.

In a further aspect, the present invention provides a method for detecting colon cancer in a patient comprising: (a) obtaining a biological sample from the patient; (b) contacting the sample with an oligonucleotide probe specific for a polynucleotide molecule that encodes one of the above polypeptides; and (c) detecting in the sample a polynucleotide sequence that hybridizes to the oligonucleotide probe. Preferably, the oligonucleotide probe comprises at least about 15 contiguous nucleotides of a polynucleotide molecule comprising a partial sequence from any of the following: SEQ ID NO: 1–112.

In related aspects, diagnostic kits comprising the above oligonucleotide probes or primers are provided.

In yet a further aspect, methods for the treatment of colon cancer in a patient are provided, the methods comprising obtaining PBMC from the patient, incubating the PBMC with a polypeptide of the present invention (or a polynucleotide that encodes such a polypeptide) to provide incubated T cells and administering the incubated T cells to the patient. The present invention additionally provides methods for the treatment of colon cancer that comprise incubating antigen presenting cells with a polypeptide of the present invention (or a polynucleotide that encodes such a polypeptide) to provide incubated antigen presenting cells and administering the incubated antigen presenting cells to the patient. In certain embodiments, the antigen presenting cells are selected from the group consisting of dendritic cells and macrophages. Compositions for the treatment of colon cancer comprising T cells or antigen presenting cells that have been incubated with a polypeptide or polynucleotide of the present invention are also provided.

These and other aspects of the present invention will become apparent upon reference to the following detailed description. All references disclosed herein are hereby incorporated by reference in their entirety as if each was incorporated individually.

DETAILED DESCRIPTION OF THE INVENTION

As noted above, the present invention is generally directed to compositions and methods for the therapy and diagnosis of colon cancer. The compositions described herein include polypeptides, fusion proteins and polynucleotide molecules. Also included within the present invention are molecules (such as an antibody or fragment thereof) that bind to the inventive polypeptides. Such molecules are referred to herein as "binding agents."

In one aspect, the subject invention discloses polypeptides comprising an immunogenic portion of a human colon tumor protein, wherein the colon tumor protein includes an amino acid sequence encoded by a polynucleotide molecule. For example, such a sequence can be (a) nucleotide sequences recited in SEQ ID NO: 1–112, (b) the complements of said nucleotide sequences, and (c) variants of such sequences. As used herein, the term "polypeptide" encompasses amino acid chains of any length, including full length proteins, wherein the amino acid residues are linked by covalent peptide bonds. Thus, a polypeptide comprising a portion of one of the above colon tumor proteins may consist entirely of the portion, or the portion may be present within a larger polypeptide that contains additional sequences. The additional sequences may be derived from the native protein or may be heterologous, and such sequences may (but need not) be immunoreactive and/or antigenic. As detailed below, such polypeptides may be isolated from colon tumor tissue or prepared by synthetic or recombinant means.

As used herein, an "immunogenic portion" of a colon tumor protein is a portion that is capable of eliciting an immune response in a patient inflicted with colon cancer and as such binds to antibodies present within sera from a colon cancer patient. Such immunogenic portions generally comprise at least about 5 amino acid residues, more preferably at least about 10, and most preferably at least about 20 amino acid residues. Immunogenic portions of the proteins described herein may be identified in antibody binding assays. Such assays may generally be performed using any of a variety of means known to those of ordinary skill in the art, as described, for example, in Harlow and Lane, *Antibodies: A Laboratory Manual*, Cold Spring Harbor Laboratory, Cold Spring Harbor, N.Y., 1988. For example, a polypeptide may be immobilized on a solid support (as described below) and contacted with patient sera to allow binding of antibodies within the sera to the immobilized polypeptide. Unbound sera may then be removed and bound antibodies detected using, for example, $^{125}$I-labeled Protein A. Alternatively, a polypeptide may be used to generate monoclonal and polyclonal antibodies for use in detection of the polypeptide in blood or other fluids of colon cancer patients. Methods for preparing and identifying immunogenic portions of antigens of known sequence are well known in the art and include those summarized in Paul, *Fundamental Immunology*, $3^{rd}$ ed., Raven Press, 1993, pp. 243–247.

The term "polynucleotide(s)," as used herein, means a single or double-stranded polymer of deoxyribonucleotide or ribonucleotide bases and includes DNA and corresponding RNA molecules, including HnRNA and mRNA molecules, both sense and anti-sense strands, and comprehends cDNA, genomic DNA and recombinant DNA, as well as wholly or partially synthesized polynucleotides. An HnRNA molecule contains introns and corresponds to a DNA molecule in a generally one-to-one manner. An mRNA molecule corresponds to an HnRNA and DNA molecule from which the introns have been excised. A polynucleotide may consist of an entire gene, or any portion thereof. Operable anti-sense polynucleotides may comprise a fragment of the corresponding polynucleotide, and the definition of "polynucleotide" therefore includes all such operable anti-sense fragments.

The compositions and methods of the present invention also encompass variants of the above polypeptides and polynucleotides. A polypeptide "variant," as used herein, is a polypeptide that differs from the recited polypeptide only in conservative substitutions and/or modifications, such that the therapeutic, antigenic and/or immunogenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. Polypeptide variants preferably exhibit at least about 70%, more preferably at least about 90% and most preferably at least about 95% identity (determined as describe below) to the identified polypeptides.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A nucleotide "variant" is a sequence that differs from the recited nucleotide sequence in having one or more nucleotide deletions, substitutions or additions. Such modifications may be readily introduced using standard mutagenesis techniques, such as oligonucleotide-directed site-specific mutagenesis as taught, for example, by Adelman et al. (*DNA*, 2:183, 1983). Nucleotide variants may be naturally occurring allelic variants, or non-naturally occurring variants. Variant nucleotide sequences preferably exhibit at least about 70%, more preferably at least about 80% and most preferably at least about 90% identity (determined as described below) to the recited sequence.

The antigens provided by the present invention include variants that are encoded by polynucleotide sequences which are substantially homologous to one or more of the polynucleotide sequences specifically recited herein. "Substantial homology," as used herein, refers to polynucleotide sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.–65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing polynucleotide sequences are also within the scope of this invention, as are nucleotide sequences that, due to code degeneracy, encode an immunogenic polypeptide that is encoded by a hybridizing polynucleotide sequence.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundaiton, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) Rapid similarity searches of nucleic acid and protein data banks *Proc. Natl. Acad, Sci. USA* 80:726–730.

Preferably, the "percentage of sequence identity" is determined by comparing two optimally aligned sequences over a window of comparison of at least 20 positions, wherein the portion of the polynucleotide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Also included in the scope of the present invention are alleles of the genes encoding the nucleotide sequences recited herein. As used herein, an "allele" or "allellic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone or in combination with the others, one or more times in a given sequence.

For colon tumor polypeptides with immunoreactive properties, variants may, alternatively, be identified by modifying the amino acid sequence of one of the above polypeptides, and evaluating the immunoreactivity of the modified polypeptide. For colon tumor polypeptides useful for the generation of diagnostic binding agents, a variant may be identified by evaluating a modified polypeptide for the ability to generate antibodies that detect the presence or absence of colon cancer. Such modified sequences may be prepared and tested using, for example, the representative procedures described herein.

The colon tumor polypeptides of the present invention, and polynucleotides encoding such polypeptides, may be isolated from colon tumor tissue using any of a variety of methods well known in the art. Polynucleotide sequences corresponding to a gene (or a portion thereof) encoding one of the inventive colon tumor proteins may be isolated from a colon tumor cDNA library using a subtraction technique as described in detail below. Examples of such polynucleotide sequences are provided in SEQ ID NO: 1–112. Partial polynucleotide sequences thus obtained may be used to design oligonucleotide primers for the amplification of full-length polynucleotide sequences from a human genomic polynucleotide library or from a colon tumor cDNA library in a polymerase chain reaction (PCR), using techniques well known in the art (see, for example, Mullis et al., *Cold Spring Harbor Symp. Quant. Biol.* 51:263, 1987; Erlich ed., *PCR Technology*, Stockton Press, NY, 1989). For this approach, sequence-specific primers may be designed based on the nucleotide sequences provided herein and may be purchased or synthesized.

Once a polynucleotide sequence encoding a polypeptide is obtained, the polypeptide may be produced recombinantly by inserting the polynucleotide sequence into an expression vector and expressing the polypeptide in an appropriate host. Any of a variety of expression vectors known to those of ordinary skill in the art may be employed to express recombinant polypeptides of this invention. Expression may be achieved in any appropriate host cell that has been transformed or transfected with an expression vector containing a polynucleotide molecule that encodes the recombinant polypeptide. Suitable host cells include prokaryotes, yeast, insect and higher eukaryotic cells. Preferably, the host cells employed are *E. coli*, yeast or a mammalian cell line, such as COS or CHO cells. The polynucleotide sequences expressed in this manner may encode naturally occurring polypeptides, portions of naturally occurring polypeptides, or other variants thereof. Supernatants from suitable host/vector systems which secrete the recombinant polypeptide may first be concentrated using a commercially available filter. The concentrate may then be applied to a suitable purification matrix, such as an affinity matrix or ion exchange resin. Finally, one or more reverse phase HPLC steps can be employed to further purify the recombinant polypeptide.

The colon tumor polypeptides disclosed herein may also be generated by synthetic means. In particular, synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, *J. Am. Chem. Soc.* 85:2149–2146, 1963). Equipment for automated synthesis of polypeptides is commercially available from suppliers such as Perkin Elmer/Applied BioSystems Division (Foster City, Calif.), and may be operated according to the manufacturer's instructions.

In general, regardless of the method of preparation, the polypeptides disclosed herein are prepared in an isolated, substantially pure form (i.e., the polypeptides are homogenous as determined by amino acid composition and primary sequence analysis). Preferably, the polypeptides are at least about 90% pure, more preferably at least about 95% pure and most preferably at least about 99% pure. In certain preferred embodiments, described in more detail below, the substantially pure polypeptides are incorporated into pharmaceutical compositions or vaccines for use in one or more of the methods disclosed herein.

In a related aspect, the present invention provides fusion proteins comprising a first and a second inventive polypeptide or, alternatively, a polypeptide of the present invention and a known colon tumor antigen, together with variants of such fusion proteins. The fusion proteins of the present invention may (but need not) include a linker peptide between the first and second polypeptides.

A polynucleotide sequence encoding a fusion protein of the present invention is constructed using known recombinant DNA techniques to assemble separate polynucleotide sequences encoding the first and second polypeptides into an appropriate expression vector. The 3' end of a polynucleotide sequence encoding the first polypeptide is ligated, with or without a peptide linker, to the 5' end of a polynucleotide sequence encoding the second polypeptide so that the reading frames of the sequences are in phase to permit mRNA translation of the two polynucleotide sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The ligated polynucleotide sequences are operably linked to suitable transcriptional or translational regulatory elements. The regulatory elements responsible for expression of polynucleotide are located only 5' to the polynucleotide sequence encoding the first polypeptides. Similarly, stop codons require to end translation and transcription termination signals are only present 3' to the polynucleotide sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.*, 336:86–91 (1997)).

Polypeptides of the present invention that comprise an immunogenic portion of a colon tumor protein may generally be used for therapy of colon cancer, wherein the polypeptide stimulates the patient's own immune response to colon tumor cells. The present invention thus provides methods for using one or more of the compounds described herein (which may be polypeptides, polynucleotide molecules or fusion proteins) for immunotherapy of colon cancer in a patient. As used herein, a "patient" refers to any warm-blooded animal, preferably a human. A patient may be afflicted with disease, or may be free of detectable disease. Accordingly, the compounds disclosed herein may be used to treat colon cancer or to inhibit the development of colon cancer. The compounds are preferably administered either prior to or following surgical removal of primary tumors and/or treatment by administration of radiotherapy and conventional chemotherapeutic drugs.

In these aspects, the inventive polypeptide is generally present within a pharmaceutical composition or a vaccine. Pharmaceutical compositions may comprise one or more polypeptides, each of which may contain one or more of the above sequences (or variants thereof), and a physiologically acceptable carrier. The vaccines may comprise one or more such polypeptides and a non-specific immune-response enhancer, wherein the non-specific immune response enhancer is capable of eliciting or enhancing an immune response to an exogenous antigen. Examples of non-specific-immune response enhancers include adjuvants, biodegradable microspheres (e.g., polylactic galactide) and liposomes (into which the polypeptide is incorporated). Pharmaceutical compositions and vaccines may also contain other epitopes of colon tumor antigens, either incorporated into a fusion protein as described above (i.e., a single polypeptide that contains multiple epitopes) or present within a separate polypeptide.

Alternatively, a pharmaceutical composition or vaccine may contain polynucleotides encoding one or more of the above polypeptides and/or fusion proteins, such that the polypeptide is generated in situ. In such pharmaceutical compositions and vaccines, the polynucleotides may be present within any of a variety of delivery systems known to those of ordinary skill in the art, including nucleic acid expression systems, bacteria and viral expression systems. Appropriate nucleic acid expression systems contain the necessary polynucleotide sequences for expression in the patient (such as a suitable promoter). Bacterial delivery systems involve the administration of a bacterium (such as Bacillus-Calmette-Guerrin) that expresses an epitope of a colon cell antigen on its cell surface. In a preferred embodiment, the polynucleotide may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating polynucleotides into such expression systems are well known to those of ordinary skill in the art. The polynucleotide may also be "naked," as described, for example, in published PCT application WO 90/11092, and Ulmer et al., *Science* 259:1745–1749, 1993, reviewed by Cohen, *Science* 259:1691–1692, 1993. The uptake of naked polynucleotide may be increased by coating the polynucleotide onto biodegradable beads, which are efficiently transported into the cells.

Routes and frequency of administration, as well as dosage, will vary from individual to individual and may parallel those currently being used in immunotherapy of other diseases. In general, the pharmaceutical compositions and vaccines may be administered by injection (e.g., intracutaneous, intramuscular, intravenous or subcutaneous), intranasally (e.g., by aspiration) or orally. Between 1 and 10 doses may be administered over a 3–24 week period. Preferably, 4 doses are administered, at an interval of 3 months, and booster administrations may be given periodically thereafter. Alternate protocols may be appropriate for individual patients. A suitable dose is an amount of polypeptide or polynucleotide that is effective to raise an immune response (cellular and/or humoral) against colon tumor cells in a treated patient. A suitable immune response is at least 10–50% above the basal (i.e., untreated) level. In general, the amount of polypeptide present in a dose (or produced in situ by the polynucleotide in a dose) ranges from about 1 pg to about 100 mg per kg of host, typically from about 10 pg to about 1 mg, and preferably from about 100 pg to about 1 $\mu$g. Suitable dose sizes will vary with the size of the patient, but will typically range from about 0.01 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

Any of a variety of immune-response enhancers may be employed in the vaccines of this invention. For example, an adjuvant may be included. Most adjuvants contain a substance designed to protect the antigen from rapid catabolism, such as aluminum hydroxide or mineral oil, and a nonspecific stimulator of immune response, such as lipid A, *Bordella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage or B-cells, may be pulsed with immunoreactive polypeptides or transfected with a polynucleotide sequence(s), using standard techniques well known in the art. For example, antigen presenting cells may be transfected with a polynucleotide sequence, wherein said sequence contains a promoter region appropriate for increasing expression, and can be expressed as part of a recombinant virus or other expression system. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," *Immunological Reviews*, 157:177, 1997).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides may be employed to generate tumor reactive T cell subsets by selective in vitro stimulation and expansion of autologous T cells to provide antigen-specific T cells which may be subsequently transferred to the patient as described, for example, by Chang et al. (*Crit. Rev. Oncol. Hematol.*, 22(3), 213, 1996). Cells of the immune system, such as T cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T cells. The population of tumor antigen-specific T cells is then expanded using standard techniques and the cells are administered back to the patient.

In another embodiment, T-cell and/or antibody receptors specific for the polypeptides can be cloned, expanded, and transferred into other vectors or effector cells for use in adoptive immunotherapy.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate tumors in a murine model has been demonstrated by Cheever et al, *Immunological Reviews*, 157:177, 1997).

Additionally, vectors expressing the disclosed polynucleotides may be introduced into stem cells taken from the patient and clonally propagated in vitro for autologous transplant back into the same patient.

Polypeptides and fusion proteins of the present invention may also, or alternatively, be used to generate binding agents, such as antibodies or fragments thereof, that are capable of detecting metastatic human colon tumors. Binding agents of the present invention may generally be prepared using methods known to those of ordinary skill in the art, including the representative procedures described herein. Binding agents are capable of differentiating between patients with and without colon cancer, using the representative assays described herein. In other words, antibodies or other binding agents raised against a colon tumor protein, or a suitable portion thereof, will generate a signal indicating the presence of primary or metastatic colon cancer in at least about 20% of patients afflicted with the disease, and will generate a negative signal indicating the absence of the disease in at least about 90% of individuals without primary or metastatic colon cancer. Suitable portions of such colon tumor proteins are portions that are able to generate a binding agent that indicates the presence of primary or metastatic colon cancer in substantially all (i.e., at least about 80%, and preferably at least about 90%) of the patients for which colon cancer would be indicated using the full length protein, and that indicate the absence of colon cancer in substantially all of those samples that would be negative when tested with full length protein. The representative assays described below, such as the two-antibody sandwich assay, may generally be employed for evaluating the ability of a binding agent to detect metastatic human colon tumors.

The ability of a polypeptide prepared as described herein to generate antibodies capable of detecting primary or metastatic human colon tumors may generally be evaluated by raising one or more antibodies against the polypeptide (using, for example, a representative method described herein) and determining the ability of such antibodies to detect such tumors in patients. This determination may be made by assaying biological samples from patients with and without primary or metastatic colon cancer for the presence of a polypeptide that binds to the generated antibodies. Such test assays may be performed, for example, using a representative procedure described below. Polypeptides that generate antibodies capable of detecting at least 20% of primary or metastatic colon tumors by such procedures are considered to be useful in assays for detecting primary or metastatic human colon tumors. Polypeptide specific antibodies may be used alone or in combination to improve sensitivity.

Polypeptides capable of detecting primary or metastatic human colon tumors may be used as markers for diagnosing colon cancer or for monitoring disease progression in patients. In one embodiment, colon cancer in a patient may be diagnosed by evaluating a biological sample obtained from the patient for the level of one or more of the above polypeptides, relative to a predetermined cut-off value. As used herein, suitable "biological samples" include blood, sera, urine and/or colon secretions.

The level of one or more of the above polypeptides may be evaluated using any binding agent specific for the polypeptide(s). A "binding agent," in the context of this invention, is any agent (such as a compound or a cell) that binds to a polypeptide as described above. As used herein, "binding" refers to a noncovalent association between two separate molecules (each of which may be free (i.e., in solution) or present on the surface of a cell or a solid support), such that a "complex" is formed. Such a complex may be free or immobilized (either covalently or noncovalently) on a support material. The ability to bind may generally be evaluated by determining a binding constant for the formation of the complex. The binding constant is the value obtained when the concentration of the complex is divided by the product of the component concentrations. In general, two compounds are said to "bind" in the context of the present invention when the binding constant for complex formation exceeds about $10^3$ L/mol. The binding constant may be determined using methods well known to those of ordinary skill in the art.

Any agent that satisfies the above requirements may be a binding agent. For example, a binding agent may be a ribosome with or without a peptide component, an RNA molecule or a peptide. In a preferred embodiment, the binding partner is an antibody, or a fragment thereof Such antibodies may be polyclonal, or monoclonal. In addition, the antibodies may be single chain, chimeric, CDR-grafted or humanized. Antibodies may be prepared by the methods described herein and by other methods well known to those of skill in the art.

There are a variety of assay formats known to those of ordinary skill in the art for using a binding partner to detect polypeptide markers in a sample. See, e.g., Harlow and Lane, *Antibodies: A Laboratory Manual*, Cold Spring Harbor Laboratory, 1988. In a preferred embodiment, the assay involves the use of binding partner immobilized on a solid support to bind to and remove the polypeptide from the remainder of the sample. The bound polypeptide may then be detected using a second binding partner that contains a reporter group. Suitable second binding partners include antibodies that bind to the binding partner/polypeptide complex. Alternatively, a competitive assay may be utilized, in which a polypeptide is labeled with a reporter group and allowed to bind to the immobilized binding partner after incubation of the binding partner with the sample. The extent to which components of the sample inhibit the binding of the labeled polypeptide to the binding partner is indicative of the reactivity of the sample with the immobilized binding partner.

The solid support may be any material known to those of ordinary skill in the art to which the antigen may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the antigen and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 µg, and preferably about 100 ng to about 1 µg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a second antibody (containing a reporter group) capable of binding to a different site on the polypeptide is added. The amount of second antibody that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is that period of time that is sufficient to detect the presence of polypeptide within a sample obtained from an individual with colon cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include enzymes (such as horseradish peroxidase), substrates, cofactors, inhibitors, dyes, radionuclides, luminescent groups, fluorescent groups and biotin. The conjugation of antibody to reporter group may be achieved using standard methods known to those of ordinary skill in the art.

The second antibody is then incubated with the immobilized antibody-polypeptide complex for an amount of time sufficient to detect the bound polypeptide. An appropriate amount of time may generally be determined by assaying the level of binding that occurs over a period of time. Unbound second antibody is then removed and bound second antibody is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of colon cancer, the signal detected from the reporter group that remains bound to the solid support is generally compared to a signal that corresponds to a predetermined cut-off value. In one preferred embodiment, the cut-off value is the average mean signal obtained when the immobilized antibody is incubated with samples from patients without colon cancer. In general, a sample generating a signal that is three standard deviations above the predetermined cut-off value is considered positive for colon cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for colon cancer.

In a related embodiment, the assay is performed in a flow-through or strip test format, wherein the antibody is immobilized on a membrane, such as nitrocellulose. In the flow-through test, polypeptides within the sample bind to the immobilized antibody as the sample passes through the membrane. A second, labeled antibody then binds to the antibody-polypeptide complex as a solution containing the second antibody flows through the membrane. The detection of bound second antibody may then be performed as described above. In the strip test format, one end of the membrane to which antibody is bound is immersed in a solution containing the sample. The sample migrates along the membrane through a region containing second antibody and to the area of immobilized antibody. Concentration of second antibody at the area of immobilized antibody indicates the presence of colon cancer. Typically, the concentration of second antibody at that site generates a pattern, such as a line, that can be read visually. The absence of such a pattern indicates a negative result. In general, the amount of antibody immobilized on the membrane is selected to generate a visually discernible pattern when the biological sample contains a level of polypeptide that would be sufficient to generate a positive signal in the two-antibody sandwich assay, in the format discussed above. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the antigens or antibodies of the present invention. The above descriptions are intended to be exemplary only.

In another embodiment, the above polypeptides may be used as markers for the progression of colon cancer. In this embodiment, assays as described above for the diagnosis of colon cancer may be performed over time, and the change in the level of reactive polypeptide(s) evaluated. For example, the assays may be performed every 24–72 hours for a period of 6 months to 1 year, and thereafter performed as needed. In general, colon cancer is progressing in those patients in whom the level of polypeptide detected by the binding agent increases over time. In contrast, colon cancer is not progressing when the level of reactive polypeptide either remains constant or decreases with time.

Antibodies for use in the above methods may be prepared by any of a variety of techniques known to those of ordinary skill in the art. See, e.g., Harlow and Lane, *Antibodies: A Laboratory Manual*, Cold Spring Harbor Laboratory, 1988. In one such technique, an immunogen comprising the antigenic polypeptide is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Monoclonal antibodies of the present invention may also be used as therapeutic reagents, to diminish or eliminate colon tumors. The antibodies may be used on their own (for instance, to inhibit metastases) or coupled to one or more therapeutic agents. Suitable agents in this regard include radionuclides, differentiation inducers, drugs, toxins, and derivatives thereof. Preferred radionuclides include $^{90}$Y, $^{123}$I, $^{125}$I, $^{131}$I, $^{186}$Re, $^{188}$Re, $^{211}$At, and $^{212}$Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Diagnostic reagents of the present invention may also comprise polynucleotide sequences encoding one or more of the above polypeptides, or one or more portions thereof. For example, at least two oligonucleotide primers may be employed in a polymerase chain reaction (PCR) based assay to amplify colon tumor-specific cDNA derived from a biological sample, wherein at least one of the oligonucleotide primers is specific for a polynucleotide molecule encoding a colon tumor protein of the present invention. The presence of the amplified cDNA is then detected using techniques well known in the art, such as gel electrophoresis. Similarly, oligonucleotide probes specific for a polynucleotide molecule encoding a colon tumor protein of the present invention may be used in a hybridization assay to detect the presence of an inventive polypeptide in a biological sample.

As used herein, the term "oligonucleotide primer/probe specific for a polynucleotide molecule" means an oligonucleotide sequence that has at least about 60%, preferably at least about 75% and more preferably at least about 90%, identity to the polynucleotide molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a polynucleotide molecule comprising sequence selected from SEQ ID NO: 1–112. Preferably, oligonucleotide probes for use in the inventive diagnostic methods comprise at least about 15 contiguous oligonucleotides of a polynucleotide molecule comprising a sequence provided in SEQ ID NO: 1–112. Techniques for both PCR based assays and hybridization assays are well known in the art (see, for example, Mullis et al. Ibid; Ehrlich, Ibid). Primers or probes may thus be used to detect colon tumor-specific sequences in biological samples, including blood, semen, colon tissue and/or colon tumor tissue.

The following Examples are offered by way of illustration and not by way of limitation.

EXAMPLES

Example 1

ISOLATION AND CHARACTERIZATION OF COLON TUMOR POLYPEPTIDES BY PCR-BASED SUBTRACTION AND MICROARRAY ANALYSIS

A cDNA library was constructed in the PCR2.1 vector (Invitrogen, Carlsbad, Calif.) by subtracting a pool of three colon tumors with a pool of normal colon, spleen, brain, liver, kidney, lung, stomach and small intestine using PCR subtraction methodologies (Clontech, Palo Alto, Calif.). The subtraction was performed using a PCR-based protocol, which was modified to generate larger fragments. Within this protocol, tester and driver double stranded cDNA were separately digested with five restriction enzymes that recognize six-nucleotide restriction sites (MluI, MscI, PvuII, SalI and StuI). This digestion resulted in an average cDNA size of 600 bp, rather than the average size of 300 bp that results from digestion with RsaI according to the Clontech protocol. This modification did not affect the subtraction efficiency. Two tester populations were then created with different adapters, and the driver library remained without adapters.

The tester and driver libraries were then hybridized using excess driver cDNA. In the first hybridization step, driver was separately hybridized with each of the two tester cDNA populations. This resulted in populations of (a) unhybridized tester cDNAs, (b) tester cDNAs hybridized to other tester cDNAs, (c) tester cDNAs hybridized to driver cDNAs and (d) unhybridized driver cDNAs. The two separate hybridization reactions were then combined, and rehybridized in the presence of additional denatured driver cDNA. Following this second hybridization, in addition to populations (a) through (d), a fifth population (e) was generated in which tester cDNA with one adapter hybridized to tester cDNA with the second adapter. Accordingly, the second hybridization step resulted in enrichment of differentially expressed sequences which could be used as templates for PCR amplification with adaptor-specific primers.

The ends were then filled in, and PCR amplification was performed using adaptor-specific primers. Only population (e), which contained tester cDNA that did not hybridize to driver cDNA, was amplified exponentially. A second PCR amplification step was then performed, to reduce background and further enrich differentially expressed sequences.

This PCR-based subtraction technique normalizes differentially expressed cDNAs so that rare transcripts that are overexpressed in prostate tumor tissue may be recoverable. Such transcripts would be difficult to recover by traditional subtraction methods.

To characterize the complexity and redundancy of the subtracted library, ninety six clones were randomly picked and sixty five were sequenced, as previously described. These sequences were further characterized by comparison with the most recent Genbank database (April, 1998) to determine their degree of novelty. No significant homologies were found to twenty one of these clones, hereinafter referred to as 11092, 11093, 11096, 11098, 11103, 11174, 11108, 11112, 11115, 11117, 11118, 11134, 11151, 11154, 11158, 11168, 11172, 11175, 11184, 11185 and 11187. The determined cDNA sequences for these clones are provided in SEQ ID NO: 48, 49, 52, 54, 59, 60, 65–69, 79, 89, 90, 93, 99–101 and 109–111, respectively.

Two thousand clones from the above mentioned cDNA subtraction library were randomly picked and submitted to a round of PCR amplification. Briefly, 0.5 vl of glycerol stock solution was added to 99.5 vl of pcr MIX (80 vl H$_2$O, 10 vl 10×PCR Buffer, 6 vl 25 mM MgCl$_2$, 1 vl 10 mM dNTPs, 1 vl 100 mM M13 forward primer (CACGACGTTGTAAAACGACGG), 1 vl 100 mM M13 reverse primer (CACAGGAAACAGCTATGACC), and 0.5 vl 5 u/ml Taq polymerase (primers provided by (Operon Technologies, Alameda, Calif.). The PCR amplification was run for thirty cycles under the following conditions: 95° C. for 5 min., 92° C. for 30 sec., 57° C. for 40 sec., 75° C. for 2 min. and 75° C. for 5 minutes.

mRNA expression levels for representative clones were determined using microarray technology (Synteni, Palo Alto, Calif.) in colon tumor tissues (n=25), normal colon tissues (n=6), kidney, lung, liver, brain, heart, esophagus, small intestine, stomach, pancreas, adrenal gland, salivary gland, resting PBMC, activated PBMC, bone marrow, dendritic cells, spinal cord, blood vessels, skeletal muscle, skin, breast and fetal tissues. The number of tissue samples tested in each case was one (n=1), except where specifically noted above; additionally, all the above-mentioned tissues were derived from human). The PCR amplification products were dotted onto slides in an array format, with each product occupying a unique location in the array. mRNA was extracted from the tissue sample to be tested, reverse transcribed, and fluorescent-labeled cDNA probes were generated according to the protocol provided by Synteni. The microarrays were probed with the labeled cDNA probes, the slides scanned, and fluorescence intensity was measured. This intensity correlates with the hybridization intensity.

One hundred and forty nine clones showed two or more fold overexpression in the colon tumor probe group as compared to the normal tissue probe group. These cDNA clones were further characterized by DNA sequencing with a Perkin Elmer/Applied Biosystems Division Automated Sequencer Model 373A and/or Model 377 (Foster City, Calif.). These sequences were compared to known sequences in the most recent GenBank database. No significant homologies to human gene sequences were found in forty nine of these clones, represented by the following sixteen cDNA consensus sequences: SEQ ID NO: 2, 8, 15, 16, 22, 24, 30, 32–34, 36, 38, 40, 41, 46 and 47, hereinafter referred to as Contig 2, 8, 13, 14, 20, 23, 29, 31, 35, 32, 36, 38, 41, 42, 50 and 51, respectively). Contig 29 (SEQ ID NO: 30) was found to be a Rat GSK-3-β-interacting protein Axil homolog. Also, Contigs 31 and 35 (SEQ ID NO: 32 and 33, respectively) were found to be a Mus musculus GOB-4 homolog. The determined cDNA sequences of SEQ ID NO: 1, 3–7, 9–14, 17–21, 23, 25–29, 31, 35, 37, 39, 42–45, 50, 51, 53, 55–58, 61–64, 70–78, 80–88, 91, 92, 94–98, 102–108 and 112 were found to show some homology to previously identified genes sequences.

Microarray analysis demonstrated Contig 2 (SEQ ID NO: 2) showed overexpression in 34% of colon tumors tested, as well as increased expression in normal pancreatic tissue, with no overexpression in normal colon tissues. Contig 8 (SEQ ID NO: 8) was overexpressed in 62% of colon tumors, together with half of all normal colon tissues tested; overexpression was also seen in liver and pancreas. Contig 13 (SEQ ID NO: 15) was shown to be overexpressed in 73% of colon tumors as well as in pancreas, esophagus and bone marrow. Contig 14 (SEQ ID NO: 16) was overexpressed in 40% of colon tumors and showed overexpression in 3 normal colon tissues as well as in pancreas. Contig 20 (SEQ ID NO: 22) showed overexpression in 30% of colon tumors, as well as increased expression in pancreas and bone marrow, with no overexpression in normal colon tissues. Contig 23 (SEQ ID NO: 24) showed overexpression in 30% of colon tumors, and overexpression in pancreas and 3 normal colon tissues. Contig 24, also referred to as C751p (SEQ ID NO: 19) showed overexpression in greater than 50% of colon tumors, with little or no expression in normal colon and other tissues. Contig 29 (SEQ ID NO: 30) showed overexpression in 53% of colon tumor tissues tested and no overexpression in normal tissues. Contig 32 (SEQ ID NO:

34) showed overexpression in 50% of colon tumors, along with overexpression in spinal cord and resting PBMC. Contig 36, also referred to as C755p (SEQ ID NO: 36) showed overexpression in 96% of colon tumor tissues tested, as well as in 50% of normal colon tissue; overexpression was also shown in normal lung tissue. Contig 38 (SEQ ID NO: 38) was shown to be overexpressed in 38% of colon tumors and no increased expression in any normal tissues. Contig 41 (SEQ ID NO: 40) was overexpressed in 60% of colon tumors, as well as in normal pancreas, esophagus, lung, and 2 normal colon tissues. Contig 42, also referred to as C760p (SEQ ID NO: 41) showed overexpression in all colon tumor tissues tested (n=25) and in 50% of normal colon tissues. Contig 50 (SEQ ID NO: 46) was shown to be overexpressed in 62% of colon tumors, as well as in spinal cord, skin, and dendritic cells, but not overexpressed in normal colon tissues. Contig 51 (SEQ ID NO: 47) showed overexpression in 96% of all colon tumor and fetal tissues tested, along with overexpression in skin, spinal cord, liver, heart, and resting PBMC. To the best of the inventors' knowledge, none of these sequences have been previously shown to be present in colon.

Example 2

SYNTHESIS OF POLYPEPTIDES

Polypeptides may be synthesized on a Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An isolated polynucleotide molecule consisting of a nucleotide sequence selected from the group consisting of:

(a) sequences provided in SEQ ID NO: 30, 32, 33, 38, 40, and 41; and
   (b) the complements of sequences provided in SEQ ID NO: 30, 32, 33 38, 40, and 41.

2. An expression vector comprising an isolated polynucleotide molecule of claim 1.

3. The term "isolated" has been added after the article "A".

4. The host cell of claim 3 wherein the host cell is selected from the group consisting of E. coli, yeast and mammalian cell lines.

* * * * *